(12) United States Patent
Tajima et al.

(10) Patent No.: US 8,497,104 B2
(45) Date of Patent: Jul. 30, 2013

(54) METHOD FOR PRODUCING AN ORGANIC ACID

(75) Inventors: Yoshinori Tajima, Kawasaki (JP); Yoko Yamamoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/301,096

(22) Filed: Nov. 21, 2011

(65) Prior Publication Data
US 2012/0129233 A1    May 24, 2012

Related U.S. Application Data

(63) Continuation of application No. PCT/JP2009/059679, filed on May 27, 2009.

(51) Int. Cl.
*C12P 7/46* (2006.01)

(52) U.S. Cl.
USPC .......................................... 435/145; 435/6.18

(58) Field of Classification Search
None
See application file for complete search history.

(56) References Cited

U.S. PATENT DOCUMENTS

| | | | |
|---|---|---|---|
| 5,143,833 | A | 9/1992 | Datta |
| 5,504,004 | A | 4/1996 | Guettler et al. |
| 7,335,496 | B2 | 2/2008 | Yamamoto et al. |
| 2005/0032195 | A1 | 2/2005 | Zeikus et al. |
| 2005/0079617 | A1* | 4/2005 | Cervin et al. ............... 435/471 |
| 2005/0170482 | A1 | 8/2005 | San et al. |
| 2009/0239269 | A1 | 9/2009 | Tajima et al. |
| 2010/0081180 | A1 | 4/2010 | Fukui et al. |
| 2010/0112647 | A1 | 5/2010 | Hara et al. |
| 2010/0297716 | A1 | 11/2010 | Tajima et al. |

FOREIGN PATENT DOCUMENTS

| | | |
|---|---|---|
| JP | 11-113588 | 4/1999 |
| JP | 11-196887 | 7/1999 |
| JP | 11-196888 | 7/1999 |
| JP | 2007-535926 | 12/2007 |
| WO | WO2005/116227 | 12/2005 |
| WO | WO2008/133131 | 11/2008 |
| WO | WO2008/133161 | 11/2008 |

OTHER PUBLICATIONS

Chica et al, Semi-rational approaches to engineering enzyme activity: combining the benefits of direted evolution and rational design. Current Opinion Biotechnol. 2005, 16: 378-384.*
Sen et al. Developments in directed evolution for inproving enzyme functions. Appl. Biochem. Biotechnol. 2007, 143: 212-23.*
Bechthold et al., Succinic Acid: A new platform chemical for biobased polymers from renewable resources. Chem. Eng. Technol. 31(5), 647-654, 2008.*
Burgess et al., Possible dissociation of the heparin-binding and mitogenic activities of heparin-binding (acidic fibroblast) growth factor-1 from its receptor-binding activities by site directed mutagenesis of a single lysine residue. Jnl. Cell. Biol. 111: 2129-2138, 1990.*
Lazar et al. Transforming growth factor alpha: mutation of aspartic acid 47 and leucine 48 results in different biological activities. Mol. Cell. Biol. 8 (3): 1247-1252. 1988.*
Schwartz et al. A superactive insulin: {B10-aspartic acid} insulin (human). PNAS. 84: 6408-6411. 1987.*
Lin et al., Structure-function relationship in glucagon: Properties of highly purified Des-His- Monoiodo-, and {Des-Asn28, Thr29} (homoserine lactone27)-glucagon. Biochemistry. 14: 1559-1563, 1975.*
Acland et al. Subcellular fate of the Int-2 oncoprotein is detrmined by achoice of initiation codon. Nature. 343: 662-665. 1990.*
Asanuma, N., et al., "Molecular characterization, enzyme properties and transcriptional regulation of phosphoenolpyruvate carboxykinase and pyruvate kinase in a ruminal bacterium, *Selenomonas ruminantium*," Microbiol. 2001;147:681-690.
Chao, Y.-P., et al., "Alteration of Growth Yield by Overexpression of Phosphoenolpyruvate Carboxylase and Phosphoenolpyruvate Carboxykinase in *Escherichia coli*," Appl. Environ. Microbiol. 1993;59(12):4261-4265.
Guettler, M. V., et al., "*Actinobacillus succinogenes* sp. nov., a novel succinic-acid-producing strain from the bovine rumen," Int. J. Systematic Bacteriol. 1999;49:207-216.
Laivenieks, M., et al., "Cloning, Sequencing, and Overexpression of the *Anaerobiospirillum succiniciproducens* Phosphoenolpyruvate Carboxykinase (*pckA*) Gene," Appl. Environ. Microbiol. 1997;63(6):2273-2280.
Millard, C. S., et al., "Enhanced Production of Succinic Acid by Overexpression of Phosphoenolpyruvate Carboxylase in *Escherichia coli*," Appl. Environ. Microbiol. 1996;62(5):1808-1810.
Vemuri, G. N., et al., "Succinate production in dual-phase *Escherichia coli* fermentations depends on the time of transition from aerobic to anaerobic conditions," J. Ind. Microbiol. Biotechnol. 2002;28:325-332.
International Preliminary Report on Patentability for PCT Patent App. No. PCT/JP2009/059679 (Dec. 22, 2011).
Chatterjee, R., et al., "Mutation of the *ptsG* Gene Results in Increased Production of Succinate in Fermentation of Glucose by *Escherichia coli*," Appl. Environmen. Microbiol. 2001;67(1):148-154.
Kim, P., et al., "Effect of Overexpression of *Actinobacillus succinogenes* Phosphoenolpyruvate Carboxykinase on Succinate Production in *Escherichia coli*," Appl. Environmen. Microbiol. 2004;70(2):1238-1241.
Lee, S. J., et al., "Genome-Based Metabolic Engineering of *Mannheimia succiniciproducens* for Succinic Acid Production," Appl. Environmen. Microbiol. 2006;72(3):1939-1948.
Wang, Q., et al., "Expression of galactose permease and pyruvate carboxylase in *Escherichia coli ptsG* mutant increases the growth rate and succinate yield under anaerobic conditions," Biotechnol. Lett. 2006;28:89-93.
International Search Report for PCT Patent App. No. PCT/JP2009/059679 (Jun. 23, 2009).

* cited by examiner

*Primary Examiner* — Tekchand Saidha
*Assistant Examiner* — Rama P Ramanujam
(74) *Attorney, Agent, or Firm* — Shelly Guest Cermak; Cermak Nakajima LLP

(57) ABSTRACT

An organic acid is produced by allowing a bacterium belonging to the family Enterobacteriaceae, which has an ability to produce an organic acid and has been modified so that the phosphoenolpyruvate carboxykinase activity is enhanced, and the glucose phosphotransferase activity is decreased, which is selected from *Escherichia, Enterobacter, Pantoea, Erwinia, Klebsiella* and *Raoultella* bacteria, or a product obtained by processing the bacterium, to act on an organic raw material in a reaction mixture containing carbonate ions, bicarbonate ions, or carbon dioxide gas to produce the organic acid.

7 Claims, 6 Drawing Sheets

Fig. 3A

```
A. succinogenes ATCC55618           1:----MTRLNKLVKELNLGLTDVKEIVYNPSYEQLFEEETKPGLEGPEKGTLTTLGAVAVD 57
  (SEQ ID NO:7)
H. influenzae 86-028NP              1:----MTDLNKVVKELEALGIYDVKEVVYNPSYEQLFEEETKPGLEGFEKGTLTTTGAVAVD 57
  (SEQ ID NO:9)
M. succiniciproducens MBEL55E       1:----MTDLNQLTQELGALGIHDVQEVVYNPSYELLPAEETKPGLEGYEKGTVTSQGAVAVN 57
  (SEQ ID NO:15)
P. multocida subsp. multocida str. Pm70  1:----MTDLNKVINELQALGIHDVKEIVYNPSYEQLFEEETKPGLEGYEKGIVTQQGAVAVD 57
  (SEQ ID NO:11)
S. ruminantium subsp. lactilytica   1:--------MANIDLSQYGIIGTIGILRNPSYKTLFEEETKEQLTGVEQGRVSELGAVNVK 52
  (SEQ ID NO:18)
V. cholerae 623-39                  1:MTYMEHTKAAQIDLAQYGIIGVTRLVRNPSYEMLPAEETKSIILEGYERGVVTELGAVAVD 60
  (SEQ ID NO:17)
Y. pseudotuberculosis IP32953       1:----MSVKGITPQELAAYGIHDVSEIVYNPSYELLPEEETKPTLEGYERGTLTTTGAIAVD 57
  (SEQ ID NO:19)
consensus                           1:   XXXXXXXXXXXXXXXXXXXXXXXNPSYXXLEEETXXXLXGXXXGXXXXGAXXVX 57
  (SEQ ID NO:24)

A. succinogenes ATCC55618           58:TGIFTGRSPKDKYIVCDETTKDTVWWNSE-AAKNDKPMTQETWKSLRELYAKQLSGKEL 116
H. influenzae 86-028NP              58:TGIFTGRSPKDKYIVLDEKTKDTVWWTSE-YAKNDKPNKQATWKSLKDLVTNQLSRERL 116
M. succiniciproducens MBEL55E       58:TGIFTGRSPKDKYIVLDDKTKDTVWWTSE-KVKNDKPNSQDTWNSLKGLVADQLSGKEL 116
P. multocida subsp. multocida str. Pm70  58:TGIFTGRSPKDKYIVLDDKTKDTVWWTSD-AAKNDKPMTQDTWKSLKGLVTEQLSGKEL 116
S. ruminantium subsp. lactilytica   53:TGIFTGRSPKDRFIVEDETSHDTVWWDSE-DYNNDNHRAITETWRALKKEIAKKEISNKEL 111
Y. cholerae 623-39                  61:TGIFTGRSPKDRFIVKDDTTRDTLWWTSD-KAKNDKPINQEVWNIRKALVTKQLSGKEV 119
Y. pseudotuberculosis IP32953       58:TGIFTGRSPKDAITQDTVWWADQGKSKNDKPLSQEIBSRLKGLVTEQLSGKEL 117
consensus                           58:TGIFTGRSPKDKYIVXXXXXDTVWWXXXXXXXNDXXXXXXXXXXWXLXXXXXXXLSGKXX 117
```

Fig. 3B

```
A. succinogenes ATCC55618           117:FVVRCYCGASEKHRIGVRVTEVASQAHFYKNFTRPTDEELKNFKADFTVLNGAKCTNP 176
H. influenzae 86-028NP              117:FVVLRCCGASEHURIAVRIVTEVASQAHFYKNFTRPTEEQLKNFEPDFVVSNGSKYTNP 176
M. succiniciproducens MBEL55E       117:FVVDAFCGANRDTRLAVRVVIEVASQAHFYINSFIRPSAEELRGFKPDFVVSNGAKCTNP 176
P. multocida subsp.multocida str. Pm70 117:FVIDAFCGANADTRLSVRIVTEVASQAHFYKNSFIRTEAELYGFKPDFVVSNGSKYTNP 176
S. ruminantium subsp. lactilytica   112:YYVDAFCGANKDTRMAVRFIVEVASQAHFYTNSFIQFTEELANFKPUFVVYNASRAKVE 171
V. cholerae 623-39                  120:FVLRCYCGANADTRLSVRFTTEVASQAHFYKNSFTRPSEEELAHFKPDFVVSNGAKCTNA 179
Y. pseudotuberculosis IP32953       118:FVVDTFCGANADTRLQVRFTTEVASQAHFYKNSFTRPSDEELABFEPDFTVSNGAKCTNP 177
consensus                           118:XVXXXXCGAXX XXRXXVRXXXEVASQAHFYKNSFTXPXXXXLXXFXXDFXVXNXXKXXXX 177

A. succinogenes ATCC55618           177:NWKERGLNSENFVAFNLTEGIQLIGGTWYGGERKKGFSRRNYPLPLKGVASMKCSANVG 236
H. influenzae 86-028NP              177:NWKEEGLNSENFVAFNLTERIGLIGGTWYGGERKKGFSRRNYPLPLKGVGAMKCSANVG 236
M. succiniciproducens MBEL55E       177:NFKERQGLNSENFVAFNLTEVQLIGGTWYGGERKKGFSNRNYFLPLRGIASMRCSANVS 236
P. multocida subsp.multocida str. Pm70 177:NWKERQLNSERFVAFNLTEGVQLIGGTWYGGERKKGFSNRNYFLPLKGIASMKCSANVS 236
S. ruminantium subsp. lactilytica   172:NYKELGLNSETAVVFNLTSKEQVIINTWYGGERKKGFSNNRNYFLPLKGIAASMKSANTD 231
V. cholerae 623-39                  180:KWKEDKLNSERFTVFNLTERRQLIGGTWYGGERKKGFAKNNYFLPLQGIASMKCSANAG 239
Y. pseudotuberculosis IP32953       178:QWKERGLNSENFVAFNLTERSRLIGGTWYGGERKKGFSRRNYLLPLKGIASMKCSANVG 237
consensus                           178:XXRERGLXSEXXXXXFNXTXXXQXIXXTWYGGERKKGFXMRNYXLPLXCXXXMKCSANXX 237

A. succinogenes ATCC55618           237:KKG-DVAIFPGLSGTGKTTLSTDPKRQLIGDDEHRWDESGVFNFEGGCYAKTINLSRENE 295
H. influenzae 86-028NP              237:KKG-DVAIFPGLSGTGKTTLSTDPKRELIGDDEHRWDGVIFNFEGGCYAKTINLSEENE 295
M. succiniciproducens MBEL55E       237:KKG-DVAIFPGLSGTGKTTLSTDPKRQLIGDDEHRWDKGVFNFEGGCYAKTINLSAENE 295
P. multocida subsp.multocida str. Pm70 237:KKG-DVAVFPGLSGTGKTTLSTDPKRQLIGDDEHRWDKGYFNFEGGCYAKTIKLSPENE 296
S. ruminantium subsp. lactilytica   232:KKRNTAIFPGLSGTGKTTLSTDPKRLLIGDDEHRWDKGYFNFEGGCYAKTINLSESE 291
V. cholerae 623-39                  240:KAG-DVAIFPGLSGTGKTTLSTDPKRALIGDDEHRWDKGYFNFEGGCYAKTIKLSKEAE 298
Y. pseudotuberculosis IP32953       238:FKG-DVAIFPGLSGTGKTTLSTDPKRKLIGDDEHRWDKGYFNFEGGCYAKTIKLSEEAE 296
consensus                           238:XXGXXXAXFPGLSGTGKTTLSTDPKRXLIGDDEHRWDXXGXFNFEGGCYAKXIXLXXEXE 297
```

Fig. 3C

```
A. succinogenes ATCC55618              298:PDIYGAIRRDALLENYVRAKSYDFDKGSKTENTRVSYPIYHDKIVR------PVSKAGH 351
H. influenzae 86-028NP                 298:PDIYRAIRRDALLENYVRSKSYDFDKGSKTENTRVSYPIYHDKIVK------PVSKAGH 351
M. succiniciproducens MBEL55E          298:PDIYKAIRRDALLENYVVLDNGDVDYADGSKTENTRVSYPIYHDKIVK------PVSKAGP 351
P. multocida subsp.multocida str. Pm70 298:PDIYKAIRRDALLENYVVRADGSVDYDKGSKTENTRVSYPIYHDKIYT------PVSKAGH 351
S. ruminantium subsp. lactilytica      292:PDIYGAIKRNALLENYTLDRKNIDFADKTITENTRVSYPIDRHKGTVKGPYNDKSAAPA 351
V. cholerae 623-39                     299:PDIYRAIRRDALLENYVRSKSUDFDKGSKTENTRVSYPIYHDKIVK------PVSKGGH 354
Y. pseudotuberculosis IP32953          297:PDIYRAIRRDALLENYVVLADGTYDFNDGSKTENTRVSYPIYHDKIVK------PVSKAGH 352
consensus                              298:PDIYRAIRRDALLENYXXRXKSYDXDXGSKTENTRVSYPIYHDKIVK XXXXXXXXXXXX 357

A. succinogenes ATCC55618              352:ATKVIPLTADAPGVLPPVSKLIPEGTEYYFLSGPTARLAGTERGITEPTPTPSACPGAAP 411
H. influenzae 86-028NP                 352:ATKVIPLTADAPGVLPPVSKLIPEGTKYYFLSGPTARLAGTERGITEPTPTPSACPGAAF 411
M. succiniciproducens MBEL55E          352:ATKVIPLSADAPGVLPPVSKLTPEQTKYYFLSGPTARLAGTERGITEPTPTPSACPGAAF 411
P. multocida subsp.multocida str. Pm70 352:AKKVIPLTADAPGVLPPVSKLTPEQTKYYFLSGPTARLAGTERGITEPTPTPSACPGAAF 411
S. ruminantium subsp. lactilytica      352:AKSVIPLSADAPGVLPPVSILTPEQTKYYFLSGPTARLAGTERGITEPTPTPSACPGAAF 411
V. cholerae 623-39                     355:ATKVIPLSADAPGVLPPVSKLIPEQTKYRFLSGPTARLAGTERGITEPTPTPSACPGAAF 414
Y. pseudotuberculosis IP32953          353:ATKVIPLTADAPGVLPPVSKLTAKGTQYRFLSGPTARLAGTERGVTEPTPTPSACPGAAF 412
consensus                              358:AXKVIPLXADAPGVLPPVSKLTXXGTXYXFLSGPTARLAGTERGITEPTPTPSACPGAAF 417

A. succinogenes ATCC55618              412:LSLHPIQYADVLVERMKASGAEAYLVNTGWNGTGKRISIKDTRGIIDAILDSSIEKAEMG 471
H. influenzae 86-028NP                 412:LTLHPTQYAEVLVKRMQAAGAEAYLVNTGWNGTGKRISIKDTRGIIDAILDKSIEKAEMG 471
M. succiniciproducens MBEL55E          412:LSLHPTQYAEVLVKRMQESGAEAYLVNTGWNGTGKRISIKDTRGIIDAILDKSIDKAEMG 471
P. multocida subsp.multocida str. Pm70 412:LSLHPTQYAEVLVKRMEANGAEAYLVNTGWNGTGKRISIKDTRGIIDAILDKSIEKAEMG 471
S. ruminantium subsp. lactilytica      412:LELHPTKYAEELVKKMEANGTKAYLVNTGWNGSGKRISIKDTRGIIHSGAIKKAEPTK 471
V. cholerae 623-39                     415:LTLHPTQYAEVLVKRMEANGAEAYLVNTGWNGSGKRISIKDTRGIIDAILDSSIEKAEFK 474
Y. pseudotuberculosis IP32953          413:LSLHPTQYAEVLVKRMQAVGAQAYLVNTGWNGTGKRISIKDTRAIIDAILNGEIDKAEFF 472
consensus                              418:LXLHPXXYAXXLVXRMXXXGXXAYLVNTGWNGXGKRISIKDTRXIIDAIXXGXIXKAXXX 477
```

Fig. 3D

```
A. succinogenes ATCC55618              472:KLPIFNLAIPKALPGVDPATLDPRDTYADKAQRQVKAEDLANEFYKNFVKYIANPE-AAK 530
H. influenzae 86-028NP                 472:KLPIFNLAIPKALPGVDSATLDPRDTYADKAQRQVKAEDLAGRFYKNFYKYATNEE-GKA 530
M. succiniciproducens MBEL55E          472:SLPIFNFNIPKALPGVNPAILDPRDIYADKAQEFKAQDLAGRFYKNFEKYTGTAE-GKA 530
P. multocida subsp. multocida str. Pm70 472:KLPIFNLAIPTALPGVDPAILDPRDTYADKAQTQKAKDLAGRFYKNFEKYTTNBE-GKA 530
S. ruminantium subsp. lactilytica      472:KIPVVNLEVPTELGVDTNLDPRDIYANPAPEEAKKDLAGRFTKNFDKYTKNNEAGKA 531
V. cholerae 623-39                     475:QIPIFNLQNPTALPGVDPMILDPRDTVDPLGRESKAKDLATKFTNNFDKYTDNAE-GKA 533
Y. pseudotuberculosis IP32953          473:TLPIFDLAVPMALPGVNPDILDPRDTYADKAQREKAKDLAKRFATNFDKYTDIPA-GAA 531
consensus                              478:XXPXFXXXXPXXLGVXXXILDPXDTYXXXXXXKAXDLAXRFXXNFXKYXXXXXXXX 537

A. succinogenes ATCC55618              531:LVGAGFKA-                                                        538
H. influenzae 86-028NP                 531:LIAAGFKA-                                                        538
M. succiniciproducens MBEL55E          531:LVAAGPKA-                                                        538
P. multocida subsp. multocida str. Pm70 531:LVAAGPKA-                                                        538
S. ruminantium subsp. lactilytica      532:LVAAGPKL-                                                        539
V. cholerae 623-39                     534:LVAASPRLD                                                        542
Y. pseudotuberculosis IP32953          532:LVSAGFKI-                                                        539
consensus                              538:LXXAGFXX                                                         545
```

US 8,497,104 B2

METHOD FOR PRODUCING AN ORGANIC ACID

This application is a Continuation of, and claims priority under 35 U.S.C. §120 to, International Application No. PCT/JP2009/059679, filed May 27, 2009, the entirety of which is incorporated by reference herein. Also, the Sequence Listing filed electronically herewith is hereby incorporated by reference (File name: 2011-11-21T_US-470_Seq_List; File size: 118 KB; Date recorded: Nov. 21, 2011).

BACKGROUND OF THE INVENTION

1. Field of the Invention

The present invention relates to a method for producing an organic acid such as succinic acid using a bacterium.

2. Brief Description of the Related Art

For the production of non-amino organic acids, including succinic acid, by fermentation, anaerobic bacteria are typically used, including bacteria belonging to the genus *Anaerobiospirillum* or *Actinobacillus* (U.S. Pat. Nos. 5,142,833, 5,504,004, International Journal of Systematic Bacteriology (1999), 49, 207-216). Although such anaerobic bacteria provide high product yields, many nutrients are required for their growth, and therefore it is necessary to add large amounts of organic nitrogen sources, such as corn steep liquor (CSL), into the culture medium. The addition of large amounts of sources of organic nitrogen results in not only an increase in cost for the culture medium, but also an increase in the purification cost for isolating the product, and therefore it is not economical.

In addition, methods are known in which aerobic bacteria such as coryneform bacteria are cultured once under aerobic conditions to proliferate the bacterial cells, then the bacteria are harvested and washed. As a result, a non-amino organic acid is produced without having to supply oxygen (Japanese Patent Laid-open (KOKAI) Nos. 11-113588 and 11-196888). These methods are economical, since smaller amounts of organic nitrogen can be added, and sufficient growth of the bacteria can be obtained in a simple culture medium. However, there is still room for improvement in terms of production amounts, concentration, and production rate per cell of the target organic acids, and the like. Furthermore, the production process could be simplified.

*Escherichia coli* is a facultative anaerobic gram negative bacterium, and similar to when using coryneform bacteria, methods are known for producing a non-amino organic acid by culturing the bacteria once under aerobic conditions to allow for bacterial growth, and then culturing again in the absence of oxygen to anaerobically produce the non-amino organic acid (Journal of Industrial Microbiology and Biotechnology (2002), 28 (6), 325-332). Alternatively, the bacteria can be aerobically cultured to aerobically produce the non-amino organic acid (U.S. Patent Published Application No. 20050170482). However, since *Escherichia coli* is a gram-negative bacterium, it is vulnerable to osmotic pressure, and there remains room for improvement in productivity per cell, etc. Moreover, there is also attempted production of succinic acid using *Enterobacter* bacteria (WO2008/133131, WO2008/133161).

As for the breeding of such bacteria as described above and in regards to the anaplerotic pathway, the production of non-amino organic acids by fermentation utilizing strains of *Escherichia coli*, coryneform bacterium, etc., and the like have been reported. Specifically, in these bacteria, phosphoenolpyruvate carboxylase (PEPC) activity or pyruvate carboxylase (PYC) activity is enhanced (Japanese Patent Laid-open Nos. 11-196888 and 11-196887, Applied and Environmental Microbiology (1996), 62, 1808-1810).

As for phosphoenolpyruvate carboxykinase (PEPCK), it is thought that this enzyme generates phosphoenolpyruvic acid from oxalacetic acid by decarboxylation, and it mainly advances the metabolic reactions toward glyconeogenesis (Applied and Environmental Microbiology (1996), 62, 1808-1810, Applied and Environmental Microbiology (1993), 59, 4261-4265). Another type of PEPCK enzyme has been reported that is in equilibrium with the reverse reaction of the reaction described above, that is, the reaction that generates oxalacetic acid from phosphoenolpyruvic acid by carbon dioxide fixation. The presence of this type of PEPCK has been confirmed in some bacteria which produce succinic acid in the presence of high concentrations of carbon dioxide, that is, *Mannheimia succiniciproducens, Actinobacillus succinogenes, Anaerobiospirillum succiniciproducens,* and *Selenomonas ruminantium* (Applied and Environmental Microbiology (2006), 72, 1939-1948, Applied and Environmental Microbiology (1997), 63, 2273-2280, Applied and Environmental Microbiology (2004), 70, 1238-1241, Microbiology (2001), 147, 681-690). It has also been reported that increasing the activity of PEPCK derived from *Actinobacillus succinogenes* in *Escherichia coli* is effective for increasing production of succinic acid (Applied and Environmental Microbiology (2004), 70, 1238-1241). However, this improvement was confirmed only in a PEPC-deficient strain, and the converse has also been reported, in that the increase in the production of succinic acid is NOT observed in a non-deficient strain (Applied and Environmental Microbiology (2004), 70, 1238-1241).

Further, there are also reported production of a non-amino organic acid by fermentation using a strain in which a mutation is introduced into the ptsG gene coding for the membrane binding subunit IICB (Glc) of the glucose phosphotransferase system (PTS) or the ptsG gene is deleted, and the like (for example, Japanese Patent Laid-open Based on PCT Application (KOHYO) No. 2007-535926, Applied and Environmental Microbiology (2001), 67, 148-154, Biotechnology Letters (2006), 28, 89-93). However, it is not reported that a marked effect is attainable on succinic acid fermentation by inactivating the ptsG gene, and further enhancing the activity of PEPCK.

SUMMARY OF THE INVENTION

An aspect of the present invention is to provide a method for producing an organic acid using a bacterium that shows higher production efficiency.

It has been found that the production amount or yield of an organic acid can be markedly increased by using a bacterium which belongs to the family Enterobacteriaceae, such as *Escherichia, Enterobacter, Pantoea, Erwinia, Klebsiella,* and *Raoultella* bacteria, and has been modified so that the phosphoenolpyruvate carboxykinase activity is enhanced, and the glucose phosphotransferase activity is decreased. A product obtained by processing such a bacterium can also be used.

It is an aspect of the present invention to provide a method for producing an organic acid comprising:

A) allowing a substance to act on an organic raw material in a reaction mixture containing carbonate ions, bicarbonate ions, or carbon dioxide gas, wherein the substance is selected from the group consisting of:

i) a bacterium belonging to the family Enterobacteriaceae which has an ability to produce an organic acid and has been modified so that the phosphoenolpyruvate carboxykinase activity is enhanced, and the glucose phosphotransferase activity is decreased, ii) a product obtained by processing the bacterium of i), and iii) combinations thereof; and B) collecting the organic acid, wherein the bacterium belongs to a genus selected from the group consisting of *Escherichia, Enterobacter, Pantoea, Erwinia, Klebsiella*, and *Raoultella*.

It is a further aspect of the present invention to provide the method as described above, wherein the bacterium has been modified by a method selected from the group consisting of:

i) increasing the copy number of the pckA gene, ii) modifying an expression control sequence of the pckA gene, and iii) combinations thereof.

It is a further aspect of the present invention to provide the method as described above, wherein the pckA gene is selected from the group consisting of:

(a) a DNA comprising a nucleotide sequence selected from the group consisting of SEQ ID NO: 6, 8, 10, 12, 14, 16 and 18, and (b) a DNA which hybridizes with a nucleotide sequence complementary to a nucleotide sequence selected from the group consisting of SEQ ID NO: 6, 8, 10, 12, 14, 16 and 18 under stringent conditions, and said DNA codes for a protein having phosphoenolpyruvate carboxykinase activity.

It is a further aspect of the present invention to provide the method as described above, wherein the pckA gene codes for a protein selected from the group consisting of:

A) a protein comprising an amino acid sequence selected from the group consisting of SEQ ID NO: 7, 9, 11, 13, 15, 17, 19 and 24; and B) a protein comprising an amino acid sequence selected from the group consisting of SEQ ID NO: 7, 9, 11, 13, 15, 17, 19 and 24, but which includes one or more substitutions, deletions, insertions, or additions of one or several amino acid residues.

It is a further aspect of the present invention to provide the method as described above, wherein the glucose phosphotransferase activity is decreased by a method selected from the group consisting of modifying the sequence of a gene coding for a protein of the glucose phosphotransferase system, and modifying a gene expression control region of the gene, wherein the gene is selected from the group consisting of ptsG, crr, ptsH and ptsI.

It is a further aspect of the present invention to provide the method as described above, wherein the glucose phosphotransferase activity is decreased by a method selected from the group consisting of modifying the sequence of the ptsG gene, and modifying a gene expression control region of the gene, wherein the ptsG gene codes for a protein of the glucose phosphotransferase system.

It is a further aspect of the present invention to provide the method as described above, wherein the bacterium is *Enterobacter aerogenes*.

It is a further aspect of the present invention to provide the method as described above, wherein the organic acid is succinic acid.

It is a further aspect of the present invention to provide a method for producing a succinic acid-containing polymer comprising:

A) producing succinic acid by the method as described above, and

B) polymerizing the succinic acid.

BRIEF DESCRIPTION OF THE DRAWINGS

FIGS. 3A-3D shows the alignment and consensus sequence of the amino acid sequences of various types of PEPCK.

DETAILED DESCRIPTION OF THE PREFERRED EMBODIMENTS

Figure 1:
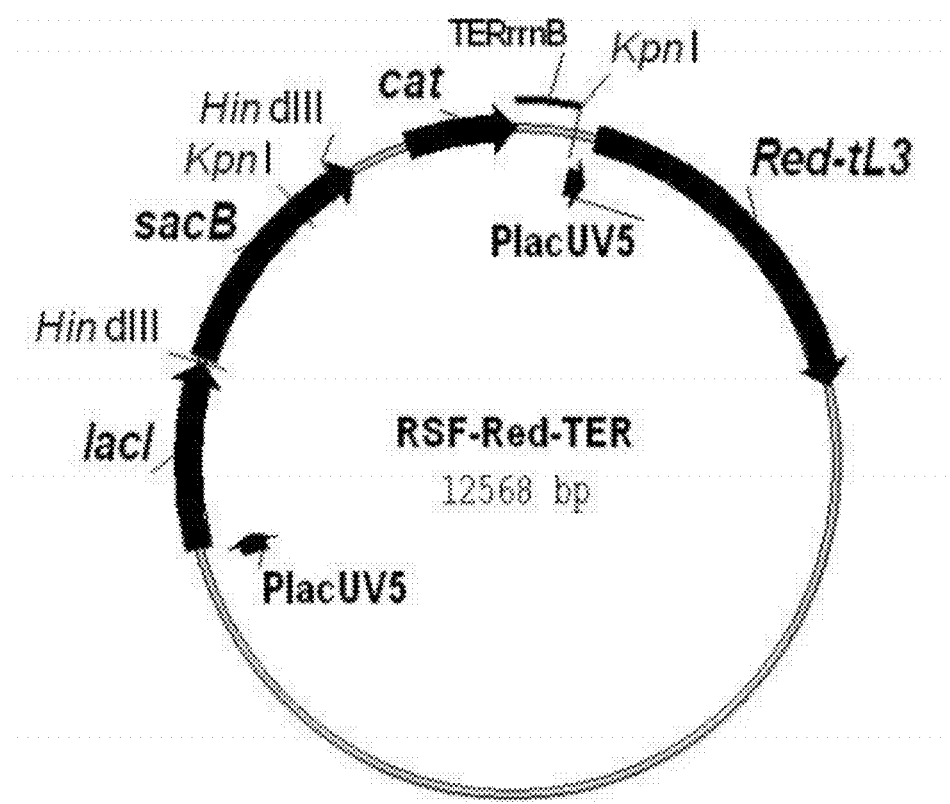
FIG. 1 shows the structure of the helper plasmid RSF-Red-TER.

Hereinafter, aspects of the presently disclosed subject matter will be explained in detail.

<1> Bacterium

The bacterium used in accordance with the presently disclosed subject matter can be a bacterium which has an ability to produce an organic acid and has been modified so that the phosphoenolpyruvate carboxykinase (henceforth abbreviated as "PEPCK") activity is enhanced, and the glucose phosphotransferase activity is decreased. The term "ability to produce an organic acid" can mean that the bacterium is able to produce and accumulate an organic acid in a medium to such a degree that the organic acid can be collected from the medium when the bacterium is cultured in the medium. The bacterium can produce a target organic acid in a medium in an amount of, for example, 0.5 g/L or more, or 1.0 g/L or more in another example. Such a bacterium can be obtained by modifying a parent bacterial strain which already is able to produce an organic acid so that the PEPCK activity is enhanced, and the glucose phosphotransferase activity is decreased. When the parent strain does not naturally produce an organic acid, the ability to produce an organic acid can be imparted to the parent strain, and then the bacterium can be modified so that the PEPCK activity is enhanced, and the glucose phosphotransferase activity is decreased. Furthermore, the ability to produce an organic acid can be imparted to a strain which has already been modified to enhance the PEPCK activity, and decrease the glucose phosphotransferase activity. The ability to produce an organic acid can be native to the chosen bacterium, or can be obtained by modifying the bacterium using mutational techniques or recombinant DNA techniques.

The organic acid can be a metabolic intermediate of the TCA cycle, and examples include succinic acid, malic acid, fumaric acid, citric acid, isocitric acid, cis-aconitic acid, and the like in an example, and succinic acid, malic acid , and fumaric acid in another example, and succinic acid in another example.

The organic acid includes an organic acid in free form and/or a salt thereof such as sulfate, hydrochloride, carbonate, ammonium salt, sodium salt and potassium salt.

The parent strain that can be used to derive the bacterium as described in the presently disclosed subject matter can be a bacterium belonging to the family Enterobacteriaceae, such as *Escherichia, Enterobacter, Pantoea, Erwinia, Klebsiella*, and *Raoultella* bacteria.

*Escherichia* bacteria, *Pantoea* bacteria, *Erwinia* bacteria, *Enterobacter* bacteria, *Klebsiella* bacteria and *Raoultella* bacteria are classified as γ-proteobacteria, and they are taxonomically very close to one another (J. Gen. Appl. Microbiol., 1997, 43, 355-361; Int. J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (Int. J. Syst. Bacteriol., 1989, 39:337-345). Furthermore, some bacteria belonging to the genus *Erwinia* were reclassified as *Pantoea ananas* or *Pantoea stewartii* (Int. J. Syst. Bacteriol., 1993, 43:162-173).

The bacterium belonging to the genus *Escherichia* is not particularly limited. Examples include, for example, the bacteria of the phyletic groups described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples include the *Escherichia coli* W3110 (ATCC 27325), *Escherichia coli* MG1655 (ATCC 47076) and the like derived from the prototype wild-type strain, K12 strain.

These strains are available from, for example, the American Type Culture Collection (Address: 10801 University Boulevard, Manassas, Va. 20110, United States of America). That is, registration numbers are given to each of the strains, and the strains can be ordered using these numbers. The registration numbers of the strains are listed in the catalogue of the American Type Culture Collection. The same shall apply to the strains described below with registration numbers of ATCC.

Examples of the *Enterobacter* bacteria include *Enterobacter agglomerans*, *Enterobacter aerogenes*, and the like. Specifically, the strains exemplified in European Patent Application Laid-open No. 952221 can be used. Typical strains of the genus *Enterobacter* include *Enterobacter agglomerans* ATCC 12287, *Enterobacter aerogenes* ATCC 13048, *Enterobacter aerogenes* NBRC 12010 strain (Biotechnol Bioeng., 2007, Mar. 27; 98(2):340-348), *Enterobacter aerogenes* AJ110637 (FERM ABP-10955), and the like.

The *Enterobacter aerogenes* AJ110637 strain was deposited at the International Patent Organism Depositary, Agency of Industrial Science and Technology (Central 6, 1-1, Higashi 1-Chome, Tsukuba-shi, Ibaraki-ken, 305-8566, Japan) on Aug. 22, 2007, and assigned an accession number of FERM P-21348. Then, the deposit was converted to an international deposit based on the Budapest Treaty on Mar. 13, 2008, and assigned an accession number of FERM BP-10955.

Typical strains of the *Pantoea* bacteria include *Pantoea ananatis, Pantoea stewartii, Pantoea agglomerans*, and *Pantoea citrea*. Specific examples include the following strains:

*Pantoea ananatis* AJ13355 (FERM BP-6614, European Patent Laid-open No. 0952221)

*Pantoea ananatis* AJ13356 (FERM BP-6615, European Patent Laid-open No. 0952221)

Although these strains are described as Enterobacter agglomerans in European Patent Laid-open No. 0952221, they are currently classified as *Pantoea ananatis* on the basis of nucleotide sequence analysis of the 16S rRNA etc., as described above.

Examples of the *Erwinia* bacteria include *Erwinia amylovora* and *Erwinia carotovora*, examples of the *Klebsiella* bacteria include *Klebsiella oxytoca* and *Klebsiella planticola*, and examples of the *Raoultella* bacteria include *Raoultella terrigena* and *Raoultella planticola*.

Specific examples include the following strains:
*Erwinia amylovora* ATCC 15580 strain
*Erwinia carotovora* ATCC 15713 strain
*Klebsiella planticola* AJ13399 strain (FERM BP-6600, European Patent Laid-open No. 955368)
*Klebsiella planticola* AJ13410 strain (FERM BP-6617, European Patent Laid-open No. 955368).
*Raoultella planticola* ATCC 33531 strain Although the AJ13399 strain and the AJ13410 strain were classified as *Klebsiella planticola* at the time of the deposit, *Klebsiella planticola* is currently classified as *Raoultella planticola* (Int. J. Syst. Evol. Microbiol., 2001 May, 51(Pt 3):925-32).

<1-1> Impartation of the Ability to Produce an Organic Acid

Hereinafter, methods for imparting to bacteria the ability to produce an organic acid, or methods to enhance the ability of bacteria to produce an organic acid are described.

To impart the ability to produce an organic acid, methods conventionally used to breed bacteria for producing substances by fermentation can be used (see "Amino Acid Fermentation", Japan Scientific Societies Press, 1st Edition, published May 30, 1986, pp. 77-100). Such methods include by acquiring an auxotrophic mutant, an analogue-resistant strain, or a metabolic regulation mutant, or by constructing a recombinant strain having enhanced expression of an enzyme involved in the biosynthesis of an organic acid. When breeding bacteria to produce an organic acid, one or more properties, such as an auxotrophic mutation, analogue resistance, or metabolic regulation mutation, can be imparted. The expression of one or more enzymes involved in biosynthesis of an organic acid can be enhanced. Furthermore, imparting properties such as auxotrophy, analogue resistance, or metabolic regulation can be combined with enhancing biosynthetic enzymes.

An auxotrophic mutant strain, a strain resistant to an organic acid analogue, or a metabolic regulation mutant strain which is able to produce an organic acid can be obtained by subjecting a parent or wild-type strain to a conventional mutagenesis, such as exposure to X-rays or UV irradiation, or a treatment with a mutagen such as N-methyl-N'-nitro-N-nitrosoguanidine, and then selecting the bacteria which exhibit an auxotrophy, analogue resistance, or metabolic regulation mutation and which also are able to produce an organic acid.

Methods for imparting to bacteria an ability to produce an organic acid, and organic acid-producing bacteria will be specifically exemplified below.

Succinic Acid-Producing Bacteria

Bacteria which can be used to produce succinic acid include strains that are unable to produce acetic acid, lactic acid, ethanol, 2,3-butanediol and formic acid.

Strains that are unable to produce acetic acid, lactic acid, ethanol, 2,3-butanediol and formic acid can be obtained by selecting strains that cannot assimilate acetic acid and lactic acid in a minimal medium, or decreasing the activities of the lactic acid biosynthesis enzymes and acetic acid biosynthesis enzymes described below (International Patent Publication WO2005/052135).

Moreover, such strains as described above can also be obtained by imparting resistance to monofluoroacetic acid (U.S. Pat. No. 5,521,075).

Production of succinic acid can be improved by imparting the ability to assimilate glucose under anaerobic conditions to a strain that is unable to produce both formic acid and lactic acid (International Patent Publication WO97/16528).

The ability to produce succinic acid can also be imparted by amplifying a gene which encodes an enzyme which is involved in the succinic acid biosynthesis system, or by deleting a gene which encodes an enzyme which catalyzes a reaction which branches off from the succinic acid biosynthesis system to produce another compound.

The ability to produce succinic acid can also be imparted by modifying a bacterium to decrease the enzymatic activity of lactate dehydrogenase (LDH), which is a lactic acid biosynthesis system enzyme (International Patent Publications WO2005/052135, WO2005/116227, U.S. Pat. No.

5,770,435, U.S. Patent Published Application No. 20070054387, International Patent Publication WO99/53035, Alam, K. Y. and Clark, D. P., 1989, J. Bacteriol., 171:6213-6217). Some bacteria can have L-lactate dehydrogenase and D-lactate dehydrogenase, and such bacteria can be modified to decrease the activity of either one, or both, of these enzymes.

The ability to produce succinic acid can also be imparted by modifying a bacterium to decrease the enzymatic activity of the formic acid biosynthesis system enzyme, pyruvate-formate lyase (PFL) (U.S. Patent Published Application No. 20070054387, International Patent Publications WO2005/116227, WO2005/52135, Donnelly, M. I., Millard, C. S., Clark, D. P., Chen, M. J., Rathke, J. W., 1998, Appl. Biochem. Biotechnol., 70-72, 187-198.).

The ability to produce succinic acid can also be imparted by modifying a bacterium to decrease the enzymatic activities of phosphate acetyltransferase (PTA), acetate kinase (ACK), pyruvate oxidase (PDXB), acetyl-CoA synthetase (ACS) and acetyl-CoA hydrolase (ACH), which are all acetic acid biosynthesis system enzymes (U.S. Patent Published Application No. 20070054387, International Patent Publications WO2005/052135, WO99/53035, WO2006/031424, WO2005/113745, and WO2005/113744).

The ability to produce succinic acid can also be enhanced by modifying a bacterium to decrease the enzymatic activity of alcohol dehydrogenase (ADH), which is an ethanol biosynthesis system enzyme (refer to International Patent Publication WO2006/031424).

A strain with an enhanced ability to produce succinic acid can also be obtained by decreasing the activity of a-acetolactate decarboxylase, which is a 2,3-butanediol biosynthesis system enzyme (J. Biosci. Bioeng., 2004, 97(4):227-32).

The ability to produce succinic acid can also be enhanced by decreasing the activities of pyruvate kinase, ArcA protein, IclR protein (iclR), glutamate dehydrogenase (gdh) and/or glutamine synthetase (glnA), and glutamate synthase (gltBD) (International Patent Publication WO2007/007933, Japanese Patent Laid-open No. 2005-168401). The gene abbreviations are in the parentheses following the enzyme names.

The ability to produce succinic acid can also be imparted by enhancing a biosynthesis system enzyme involved in succinic acid production.

The ability to produce succinic acid can also be enhanced by enhancing enzymatic activities of pyruvate carboxylase, malic enzyme, phosphoenolpyruvate carboxylase, fumarase, fumarate reductase, and malate dehydrogenase (Japanese Patent Laid-open No. 11-196888, International Patent Publication WO99/53035, 2001. Biotechnol. Bioeng., 74:89-95, Millard, C. S., Chao, Y. P., Liao, J. C., Donnelly, M. I., 1996, Appl. Environ. Microbiol., 62:1808-1810, International Patent Publication WO2005/021770, Japanese Patent Laid-open No. 2006-320208, Pil Kim, Maris Laivenieks, Claire Vieille, and J. Gregory Zeikus, 2004, Appl. Environ. Microbiol., 70:1238-1241). The enzymatic activities of these target enzymes can be enhanced by referring to the methods for enhancing expression of the pckA gene described later.

Specific examples of succinic acid-producing bacteria belonging to the family Enterobacteriaceae include the following strains:

*Enterobacter aerogenes* AJ110637 strain (FERM ABP-10955)

*Enterobacter aerogenes* VP-1 strain (J. Biosci. Bioeng., 2004, 97(4):227-32)

<1-2> Enhancing the Phosphoenolpyruvate Carboxykinase Activity

The bacterium in accordance with the presently disclosed subject matter can be obtained by modifying a bacterium having an ability to produce an organic acid such as those described above so that the phosphoenolpyruvate carboxykinase (PEPCK) activity is enhanced, and the glucose phosphotransferase activity is decreased. However, the modification to enhance the PEPCK activity and decrease the glucose phosphotransferase activity can be performed first, and then the ability to produce an organic acid can be imparted.

Phosphoenolpyruvate carboxykinase (PEPCK) reversibly catalyzes the reaction which produces oxalacetic acid (OAA) from phosphoenolpyruvic acid (PEP) by carbon dioxide fixation. "PEPCK activity" can mean the activity of catalyzing the reaction to produce OAA from PEP. PEPCK enzymes which are able to achieve reaction equilibrium and advance the reaction which results in the production of OAA from PEP can be used. The enzyme activity can be determined, for example, by measuring the amount of ATP produced at 37° C. according to the method of Pil Kim et al. using Sigma Diagnostics ATP Kit (Pil, Kim, Maris, Laivenieks, Claire, Vieille, Gregory, Zeikus, Applied And Environmental Microbiology, February 2004, pp. 1238-1241).

The increase of the PEPCK activity as compared to that of, for example, a wild-type or unmodified strain can be confirmed by measuring the enzyme activity according to the aforementioned method, or by comparing the amount of mRNA of a gene coding for PEPCK with that of the wild-type or unmodified strain. To confirm expression, exemplary methods include Northern hybridization and reverse transcriptase PCR (RT-PCR, Sambrook, J., and Russell, D. W., Molecular Cloning A Laboratory Manual/Third Edition, New York: Cold Spring Harbor Laboratory Press (2001)). The enzyme activity can be increased to any level so long as the activity is increased as compared to that of a wild-type or unmodified strain, and for example, is increased not less than 1.5 times, not less than 2 times in another example, or not less than 3 times in another example, as compared to that of, for example, a wild-type or an unmodified strain. Moreover, the increase in the enzyme activity can also be confirmed on the basis of detection of an increase in the amount of the PEPCK protein as compared to that in an unmodified or a wild-type strain, and it can be detected by, for example, Western blotting using an antibody (Sambrook, J., and Russell, D. W., Molecular Cloning A Laboratory Manual/Third Edition, New York: Cold Spring Harbor Laboratory Press (2001)).

Examples of the gene coding for PEPCK can include the pckA gene derived from *Actinobacillus succinogenes* (GenBank Accession No. YP_001343536.1, SEQ ID NO: 6), and homologues of this pckA gene. A pckA gene homologue is a gene that can be derived from another microorganism, shows high homology to the aforementioned pckA gene of *Actinobacillus succinogenes*, and codes for a protein having the PEPCK activity. Examples include, for example, the pckA gene of *Haemophilus influenzae* (GenBank Accession No. YP_248516.1, SEQ ID NO: 8), the pckA gene of *Pasteurella multocida* (GenBank Accession No. NP_246481.1, SEQ ID NO: 10), the pckA gene of *Mannheimia succiniciproducens* (GenBank Accession No. YP_089485.1, SEQ ID NO: 12), the pckA gene of *Yersinia pseudotuberculosis* (GenBank Accession No. YP_072243, SEQ ID NO: 14), the pckA gene of *Vibrio cholerae* (GenBank Accession No. ZP_01981004.1, SEQ ID NO: 16), the pckA gene of *Selenomonas ruminantium* (GenBank Accession No. AB016600, SEQ ID NO: 18), and so forth.

Examples of pckA gene homologues include genes coding for a protein having a homology of, for example, 90% or more, 95% or more, 98% or more, or 99% or more in another example, to the amino acid sequence of SEQ ID NO: 7, 9, 11, 13, 15, 17 or 19, and coding for phosphoenolpyruvate carboxykinase. Homology of amino acid sequences and nucleotide sequences can be determined by using, for example, the algorithm BLAST of Karlin and Altschul (Pro. Natl. Acad. Sci. USA, 90, 5873 (1993)) or FASTA (Methods Enzymol., 183, 63 (1990)). The BLASTN and BLASTX programs were developed on the basis of this algorithm BLAST (refer to www.ncbi.nlm.nih.govbi.nlm.nih.gov).

Alignment of the amino acid sequences of SEQ ID NOS: 7, 9, 11, 13, 15, 17 and 19 is shown in FIGS. 3A-3D. A consensus of these sequences is shown as SEQ ID NO: 24. The aforementioned pckA gene homologues can include a gene coding for the amino acid sequence of SEQ ID NO: 24, and genes coding for a protein having a homology of, for example, 90% or more, 95% or more, 98% or more, or 99% or more in another example, to the amino acid sequence of SEQ ID NO: 24, and coding for phosphoenolpyruvate carboxykinase.

Since sequences of the pckA gene from several different sources have already been reported as described above, the gene can be obtained by PCR using primers prepared on the basis of those nucleotide sequences. For example, the coding region of the pckA gene of *Actinobacillus succinogenes* and a flanking region which includes a control region, can be obtained by PCR (polymerase chain reaction, see White, T. J. et al., Trends Genet., 5, 185 (1989)) using the primers shown in SEQ ID NOS: 4 and 5 and chromosomal DNA of *Actinobacillus succinogenes* as the template. Specific examples of *Actinobacillus succinogenes* include the 130Z strain (ATCC 55618). This strain can be obtained from American Type Culture Collection (Address: 10801 University Boulevard, Manassas, Va. 20110, United States of America). Homologues of pckA from other microorganisms can also be obtained in a similar manner.

Since the nucleotide sequence of the pckA gene can differ depending on the species or strain of bacteria belonging to the family Enterobacteriaceae, the pckA gene is not limited to a gene coding for the amino acid sequence of SEQ ID NO: 7, 9, 11, 13, 15, 17, 19 or 24, and it can be a mutant or artificially modified gene that codes for a protein having a sequence of SEQ ID NO: 7, 9, 11, 13, 15, 17, 19 or 24, but which includes substitutions, deletions, insertions, additions, etc. of one or several amino acid residues at one or more positions so long as the ability is maintained to improve production of an organic acid by the bacterium with enhanced expression of the gene. Although the number meant by the term "several" can differ depending on positions in the three-dimensional structure of the protein or types of amino acid residues, it can be 1 to 20, 1 to 10 in another example, or 1 to 5 in another example. The substitutions, deletions, insertions, additions, inversions or the like of amino acid residues described above can also include those caused by a naturally occurring mutation based on individual differences, differences in species of microorganisms that contain the pckA gene (mutant or variant), or the like.

The aforementioned substitution can be a conservative substitution that is a neutral substitution, that is, one that does not result in a functional change. The conservative mutation is, for example, a conservative substitution. The conservative substitution is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of substitutions considered to be conservative substitutions can include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val.

Furthermore, the pckA gene can include a nucleotide sequence encoding a protein having a homology not less than 80% in one example, not less than 90% in another example, not less than 95% in another example, or not less than 97% in another example, to the entire amino acid sequence of SEQ ID NO: 7, 9, 11, 13, 15, 17, 19 or 24, and wherein the encoded protein improves the ability of the bacterium to produce an organic acid when expression of the gene is enhanced. Furthermore, the degree of degeneracy of the gene can vary depending on the host into which the pckA gene is introduced, and therefore codons can be replaced with those which are favorable for the chosen host. Moreover, the pckA gene can code for a protein with an elongated or deleted N- or C-terminal sequence, so long as the gene improves the ability of the bacterium to produce an organic acid when expression of the gene is enhanced in the bacterium. The length of the amino acid sequence to be elongated or deleted can be 50 amino acid residues or less, 20 or less in another example, 10 or less in another example, or 5 or less in another example. More specifically, the pckA gene can encode a protein having the amino acid sequence of SEQ ID NO: 7, 9, 11, 13, 15, 17, 19 or 24, but wherein the original amino acid sequence is elongated by 5 to 50 amino acid residues on the N-terminal or C-terminal side, or 5 to 50 residues are deleted on either side.

Genes homologous to the pckA gene as described above can be obtained by modifying a gene coding for the amino acid sequence of SEQ ID NO: 7, 9, 11, 13, 15, 17, 19 or 24 so that the protein encoded by the gene includes substitutions, deletions, insertions, or additions of amino acid residues at a specific site(s), for example, by site-specific mutagenesis. Furthermore, homologous genes can also be obtained by conventionally known mutation treatments, such as those described below. For example, the pckA gene can be treated with hydroxylamine or the like in vitro, or the microorganism, for example, *Actinobacillus succinogenes*, containing the gene can be treated with ultraviolet ray irradiation or a mutagen typically used for mutation, such as N-methyl-N'-nitro-N-nitrosoguanidine (NTG) or ethyl methanesulfonate (EMS). Another method for introducing mutations is error-prone PCR (Cadwell, R. C., PCR Meth. Appl., 2, 28 (1992)), DNA shuffling (Stemmer, W. P., Nature, 370, 389 (1994)), or StEP-PCR (Zhao, H., Nature Biotechnol., 16, 258 (1998)). Regardless of the method used, a mutation can be artificially introduced into the pckA gene by gene recombination to obtain a gene coding for highly active PEPCK.

Whether such homologous pckA genes code for a protein which improves the ability of the bacterium to produce an organic acid when expression is enhanced can be confirmed, for example, by introducing these genes into the *Enterobacter aerogenes* AJ110637 strain (FERM BP-10955) or the like, and determining whether the organic acid-producing ability of the bacterium is improved or not.

Examples of the pckA gene also include a DNA that hybridizes with a nucleotide sequence complementary to the sequence of SEQ ID NO: 6, 8, 10, 12, 14, 16 or 18, or a probe that can be prepared from these sequences under stringent conditions and codes for a protein which has the PEPCK activity. The "stringent conditions" can be conditions under which a so-called specific hybrid is formed, and non-specific hybrid is not formed. Examples include, for example, conditions under which DNAs having high homology to each other, for example, DNAs having a homology of, for example, not less than 80%, not less than 90%, not less than 95%, or not less than 97% in another example, hybridize with each other, and DNAs having homology lower than the above levels do not hybridize with each other. "Stringent conditions" can also include washing conditions which are typical in Southern hybridization, for example, washing once, or twice or three times, at salt concentrations and a temperature of 1×SSC, 0.1% SDS at 60° C., 0.1×SSC, 0.1% SDS at 60° C. in another example, or 0.1×SSC, 0.1% SDS at 68° C. in another example.

A partial sequence of a nucleotide sequence complementary to the sequence of SEQ ID NO: 6, 8, 10, 12, 14, 16 or 18 can also be used as the probe. Such a probe can be prepared by PCR using oligonucleotides prepared on the basis of any one of these nucleotide sequences as primers and a DNA fragment containing any one of the sequences as the template. When a DNA fragment having a length of about 300 bp is used as the probe, the washing conditions after hybridization under the aforementioned conditions can be exemplified by 2×SSC, 0.1% SDS at 50° C.

The aforementioned descriptions concerning gene homologues and conservative mutations can be similarly applied to the other enzyme genes described in this specification, such as the genes coding for the glucose phosphotransferase system described later.

By modifying a bacterium so that expression of a pckA gene as described above is enhanced, the PEPCK enzyme activity can be enhanced.

The expression "modified so that expression of the pckA gene is enhanced" or "modified to enhance expression of the pckA gene" can mean that the number of PEPCK molecules per cell is increased, or that the activity per PEPCK molecule is increased, etc., as compared to an unmodified strain such as a parent strain or a wild-type strain. Examples of the wild-type strain that can be used for comparison include the Enterobacter aerogenes ATCC 13048 strain and so forth.

Expression of the pckA gene can be enhanced by increasing the copy number of the pckA gene. For example, the copy number of the gene can be increased by ligating a fragment containing the pckA gene to a vector that functions in the chosen bacterium, for example, a multi copy vector, to prepare a recombinant DNA, and transforming the bacterium which is able to produce an organic acid as described above with the DNA. Alternatively, after the transformation of a wild-type strain of a bacterium, the ability to produce an organic acid can be imparted to the transformed bacterium. The copy number of the gene can also be increased by transferring a single copy or multiple copies of the pckA gene to the bacterial chromosome. Transfer of the pckA gene to the chromosome can be confirmed by Southern hybridization using a portion of the pckA gene as a probe.

Expression of the pckA gene can also be enhanced by modifying an expression control sequence of the pckA gene. For example, the promoter sequence of the pckA gene can be replaced with a stronger promoter, or by making a promoter sequence closer to a consensus sequence (WO00/18935).

Methods for constructing a bacterium which has an ability to produce an organic acid and has been modified so that the expression level of the pckA gene is increased are explained below. These methods can be performed as described in a manual such as Molecular Cloning (Cold Spring Harbor Laboratory Press, Cold Spring Harbor (USA), 2001).

Expression of the pckA gene can be enhanced by increasing the copy number by amplifying the pckA gene using a plasmid such as those described below. First, the pckA gene is cloned from the chromosome of *Actinobacillus succinogenes* or the like. Chromosomal DNA can be prepared from a bacterium, for example, by the method of Saito and Miura (see H. Saito and K. Miura, Biochem. Biophys. Acta, 72, 619 (1963); Text for Bioengineering Experiments, Edited by the Society for Bioscience and Bioengineering, Japan, p 97-98, Baifukan Co., Ltd., 1992), or the like. Oligonucleotides for use in PCR can be synthesized on the basis of the aforementioned known information, for example, the synthetic oligonucleotides shown in SEQ ID NOS: 4 and 5 can be used to amplify the pckA gene.

A gene fragment including the pckA gene amplified by PCR can itself be amplified by inserting the fragment into a vector having a replication origin that enables autonomous replication in the chosen bacterium, then transforming the bacterium with the vector. Examples of vectors which can be used to transform Enterobacteriaceae bacteria include pUC19, pUC18, pHSG299, pHSG399, pHSG398, RSF1010, pBR322, pACYC184, pMW219, and the like.

To prepare a recombinant DNA by ligating the pckA gene to a vector that functions in the chosen bacterium, the vector is digested with a restriction enzyme suitable for the ends of the pckA gene. Such a restriction enzyme site can be introduced in advance into the synthetic oligonucleotide which is used to amplify the pckA gene. Ligation is usually performed by a ligase such as T4 DNA ligase.

In order to introduce a recombinant plasmid prepared as described above into a bacterium, any known transformation method reported to date can be employed. For example, recipient cells can be treated with calcium chloride so as to increase permeability for the DNA, which has been reported for *Escherichia coli* K-12 (Mandel, M. and Higa, A., J. Mol. Biol., 53, 159 (1970)). Also, competent cells can be prepared from growing cells and DNA can be introduced into these cells, which has been reported for *Bacillus subtilis* (Duncan, C. H., Wilson, G. A. and Young, F. E., Gene, 1, 153 (1977)). Another method is to make DNA recipient cells into protoplasts or spheroplasts which easily take up a recombinant DNA, and a recombinant DNA can be introduced into these cells, which are known for *Bacillus subtilis*, actinomycetes, and yeasts (Chang, S. and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)). In addition, bacteria can also be transformed by the electric pulse method (Japanese Patent Laid-open No. 2-207791) or by the conjugal transfer method (Biotechnology (NY). 1991 January; 9(1):84-7).

The copy number of the pckA gene can also be increased by integrating multiple copies of the pckA gene into the chromosomal DNA of the bacterium, which can be accomplished by homologous recombination. This technique is performed by targeting a sequence which is present in multiple copies on the chromosomal DNA. Such sequences can include a repetitive DNA or inverted repeat present at the end of a transposable element. Alternatively, as disclosed in Japanese Patent Laid-open No. 2-109985, multiple copies of the pckA gene can be introduced into a chromosomal DNA by incorporating them into a transposon, and transferring the transposon (Japanese Patent Laid-open Nos. 2-109985, 7-107976, Mol. Gen. Genet., 245, 397-405 (1994); Plasmid, 2000 November; 44(3): 285-91).

Expression of the pckA gene can also be enhanced by replacing a native expression control sequence, such as a promoter of the pckA gene, on the chromosomal DNA or a plasmid with a stronger promoter. Other methods include modifying a factor involved in expression control of the pckA gene, such as operator or repressor, or ligating a strong terminator (Hamilton et al., Journal of Bacteriology 171:4617-4622; WO98/004715). For example, the lac promoter, trp promoter, trc promoter, tac promoter, PR promoter derived from λ-phage, lacUV promoter, and the like are known as strong promoters. Methods for evaluating the strength of promoters and examples of strong promoters are described in the paper of Goldstein et al. (Prokaryotic promoters in biotechnology, Biotechnol. Annu. Rev., 1955, 1, 105-128), and the like. Furthermore, as disclosed in WO00/18935, the strength of a promoter can be increased by making several nucleotide substitutions in the promoter region of a target gene so as to make the sequence closer to a consensus sequence. For example, the -35 region can be replaced with TTGACA or TTGCCA, and the -10 region can be replaced with TATAAT or TATAAC. In addition, it is known that the translation efficiency of mRNA is significantly affected by substituting several nucleotides in the spacer region between the ribosome-binding site (RBS) and the translation initiation codon, in particular, the sequence immediately upstream of the initiation codon.

Expression of a gene can also be enhanced by extending the survival time of the mRNA or by preventing degradation of the encoded protein in the cells. An expression control sequence such as a promoter which is upstream of the pckA gene can also be identified by using a promoter search vector or gene analysis software such as GENETYX. Expression of the pckA gene can be enhanced by substituting or modifying the promoter.

Modifying an expression control sequence can be combined with increasing the copy number of the pckA gene.

<1-3> Attenuation of Glucose Phosphotransferase

In various bacteria, glucose is taken up into cells by the glucose phosphotransferase system (PTS, PEP-dependent phosphotransferase system) coupling with phosphorylation, and metabolized by the glycolysis system. As for glucose metabolism especially in enterobacteria, it is known that the glucose phosphotransferase system is constituted by IICBGlc (ptsG gene product), IIAGlc (crr gene product), HPr (ptsH gene product) and Enzyme I (ptsI gene product) (FEBS Letters, 504 (2001), 104-111).

In the presently disclosed subject matter, a bacterial strain modified so that expression of the pckA gene is enhanced, and in addition, the glucose phosphotransferase activity is decreased is used. The expression "modified so that the glucose phosphotransferase activity is decreased" means that the glucose phosphotransferase activity is decreased as compared to a glucose phosphotransferase-unmodified strain such as a parent or wild-type strain. The glucose phosphotransferase activity is preferably decreased to 10% or less per cell of that of a glucose phosphotransferase-unmodified strain. The glucose phosphotransferase activity may be completely deleted. Decrease of the glucose phosphotransferase activity can be confirmed by measuring the glucose phosphotransferase activity by a known method (Kornberg, H. L., and R. E. Reeves, Biochem. J., 128, pp. 1339-1344 (1972)). Specific examples of the method for producing a variant strain of an enterobacterium of which glucose phosphotransferase activity is decreased include the method described in Applied and Environmental Microbiology (2001), 67, pp. 148-154, and so forth. Examples of the wild-type strain as a control for the comparison include, as for Enterobacter aerogenes, for example, the Enterobacter aerogenes ATCC 13048 strain, and so forth.

In order to decrease or eliminate the glucose phosphotransferase activity, a mutation may be introduced into a gene coding for the glucose phosphotransferase system on a chromosome, such as ptsG, crr, ptsH and ptsI, or an expression control region thereof by a conventional mutagenesis method so that intracellular activity of glucose phosphotransferase is decreased or eliminated. Such introduction of a mutation can be achieved by, for example, using genetic recombination to eliminate any of the genes mentioned above on the chromosome or to modify an expression control sequence such as a promoter or the Shine-Dalgarno (SD) sequence. It can also be achieved by introducing a mutation for amino acid substitution (missense mutation), a stop codon (nonsense mutation), or a frame shift mutation for adding or deleting one or two nucleotides into a region coding for glucose phosphotransferase on the chromosome, or partially or totally deleting the gene (Journal of Biological Chemistry 272:8611-8617 (1997)). The glucose phosphotransferase activity can also be decreased or eliminated by gene disruption, for example, by constructing a gene coding for a mutant glucose phosphotransferase, of which coding region is totally or partially deleted (disrupted gene), and substituting it for a normal gene on a chromosome by homologous recombination or the like, or by introducing a transposon or IS factor into a normal gene on a chromosome.

For example, in order to introduce a mutation that decreases or eliminates the glucose phosphotransferase activity by genetic recombination, the following methods can be used. A mutant ptsG, crr, ptsH or ptsI gene is prepared by modifying a partial sequence of any one of the genes described above so that it does not produce an enzyme that can function normally, and then a bacterium can be transformed with a DNA containing the mutant gene to cause recombination of a corresponding gene on the chromosome with the mutant gene to substitute the mutant gene for the gene on the chromosome. Such site-specific mutagenesis based on gene substitution using homologous recombination has already been established, and examples include methods of using a linear DNA such as the method called Red-driven integration developed by Datsenko and Wanner (Proc. Natl. Acad. Sci. USA, 2000, 97, 12, pp. 6640-6645), and the method utilizing the Red driven integration in combination with an excisive system derived from λ phage (Cho, E. H., Gumport, R. I., Gardner, J. F., 2002, J. Bacteriol., 184:5200-5203) (refer to WO2005/010175), a method of using a plasmid containing a temperature sensitive replication origin (U.S. Pat. No. 6,303,383, Japanese Patent Laid-open No. 05-007491, WO2005/010175), and so forth. Further, such site-specific mutagenesis based on gene substitution using homologous recombination can also be performed by using a plasmid which is not able to replicate in a host.

As the ptsG gene of Enterobacter aerogenes, the nucleotide sequence of the ptsG gene of the Enterobacter aerogenes AJ110637 strain (FERM BP-10955) is shown as SEQ ID NO: 20, and the amino acid sequence encoded by this gene is shown as SEQ ID NO: 21.

<2> Method for Producing Organic Acid

An organic acid can be produced by using a bacterium that is able to produce an organic acid, and has been modified so that expression of the pckA gene is enhanced, and the glucose phosphotransferase activity is decreased as described above. Specifically, an organic acid can be produced by allowing the bacterium, or a product obtained by processing the bacterium, to act on an organic raw material in a reaction mixture containing carbonate ions, bicarbonate ions, or carbon dioxide gas to produce the organic acid, and collecting the organic acid.

In one example of the method, by culturing the bacterium in a medium containing carbonate ions, bicarbonate ions, or carbon dioxide gas, and an organic raw material, proliferation of the bacterium and production of the organic acid occur simultaneously. In this example, the medium can be the reaction mixture. Proliferation of the bacterium and production of the organic acid can be simultaneously attained, or there can be a period during the culture when proliferation of the bacterium mainly occurs, and a period in which production of the organic acid mainly occurs.

In another example, by allowing cells to proliferate in a medium, and then allowing the cells to act on organic raw material in the reaction mixture in the presence of carbonate ions, bicarbonate ions, or carbon dioxide gas, an organic acid can be produced. In this example, a product obtained by processing the cells of the bacterium can also be used. Examples of the product obtained by processing cells include, for example, immobilized cells which can be obtained with acrylamide, carragheenan, or the like, disrupted cells, centrifugation supernatant of the disrupted product, fraction obtained by partial purification of the supernatant by ammonium sulfate treatment or the like.

Although the bacteria can be cultured on a solid medium such as agar medium by slant culture, bacteria previously cultured in a liquid medium (seed culture) are other examples.

As the medium used for the culture, a typical microorganism culture medium can be used. For example, a typical medium obtained by adding natural nutrients such as meat extract, yeast extract and peptone, to a composition including inorganic salts such as ammonium sulfate, potassium phosphate and magnesium sulfate can be used.

In the aforementioned first example, the carbon source that is added to the medium also serves as the organic raw material for the production of the organic acid.

In the aforementioned second example, after the culture, the cells are collected by centrifugation, membrane separation, or the like, and used for the organic acid production reaction.

The organic raw material is not particularly limited so long as it includes a carbon source which the chosen bacterium can assimilate to produce succinic acid. However, fermentable carbohydrates including carbohydrates such as galactose, lactose, glucose, fructose, glycerol, sucrose, saccharose, starch and cellulose, polyalcohols such as glycerol, mannitol, xylitol and ribitol, and the like are usually used. Specific examples include glucose, fructose and glycerol are preferred, and glucose. When the organic acid is succinic acid, fumaric acid or the like can be added in order to efficiently produce succinic acid as described in Japanese Patent Laid-open No. 5-68576, and malic acid can be added instead of fumaric acid.

Furthermore, a saccharified starch solution, molasses, or the like containing the fermentable carbohydrates can also be used. The fermentable carbohydrates can be used independently or in combination. Although the concentration of the aforementioned organic raw material is not particularly limited, it is more advantageous when the concentration is as high as possible within such a range that the production of the organic acid is not inhibited. In the aforementioned first example, concentration of the organic raw material in the medium is generally in the range of 5 to 30% (w/v), or 10 to 20% (w/v) in another example. Furthermore, in the aforementioned second example, the concentration of the organic raw material in the reaction mixture is generally in the range of 5 to 30% (w/v), or 10 to 20% (w/v) in another example. Furthermore, additional organic raw material can be added as its concentration decreases as the reaction progresses.

The aforementioned reaction mixture containing carbonate ions, bicarbonate ions, or carbon dioxide gas and the organic raw material is not particularly limited, and it can be, for example, a medium for culturing bacteria, or it can be a buffer such as phosphate buffer. The reaction mixture can be an aqueous solution containing a nitrogen source, inorganic salts, and the like. The nitrogen source is not particularly limited so long as it is a nitrogen source which the chosen bacterium can assimilate to produce an organic acid, and specific examples include various organic or inorganic nitrogen compounds such as ammonium salts, nitrates, urea, soybean hydrolysate, casein degradation products, peptone, yeast extract, meat extract, and corn steep liquor. Examples of the inorganic salts include various phosphates, sulfates, and metallic salts such as those of magnesium, potassium, manganese, iron, and zinc. If necessary, growth-promoting factors including vitamins such as biotin, pantothenic acid, inositol, and nicotinic acid, nucleotides, amino acids and the like can be added. In order to suppress foaming at the time of the reaction, an appropriate amount of commercially available antifoam can be added to the medium.

The pH of the reaction mixture can be adjusted by adding sodium carbonate, sodium bicarbonate, potassium carbonate, potassium bicarbonate, magnesium carbonate, sodium hydroxide, calcium hydroxide, calcium carbonate, magnesium hydroxide, or the like. Since the pH for the reaction is usually 5 to 10, or 6 to 9.5, the pH of the reaction mixture is adjusted to be within the aforementioned range with an alkaline substance, carbonate, urea, or the like even during the reaction, if needed.

The reaction mixture can include water, a buffer, a medium, or the like, but medium is a particular example. The media can contain, for example, the aforementioned organic raw material, and carbonate ions, bicarbonate ions, or carbon dioxide gas, and the reaction can be performed under anaerobic conditions. The carbonate or bicarbonate ions can be supplied from magnesium carbonate, sodium carbonate, sodium bicarbonate, potassium carbonate, potassium bicarbonate, calcium carbonate, or calcium bicarbonate, which can also be used as a neutralizing agent. However, if necessary, carbonate or bicarbonate ions can also be supplied from carbonic acid or bicarbonic acid or salts thereof or carbon dioxide gas. Specific examples of the salts of carbonic acid or bicarbonic acid include, for example, magnesium carbonate, ammonium carbonate, sodium carbonate, potassium carbonate, ammonium bicarbonate, sodium bicarbonate, potassium bicarbonate, calcium carbonate, calcium bicarbonate, and the like. Carbonate ions or bicarbonate ions can be added at a concentration of 0.001 to 5 M, 0.1 to 3 M in another example, or 1 to 2 M in another example. When carbon dioxide gas is present, it can be present in an amount of 50 mg to 25 g, 100 mg to 15 g in another example, or 150 mg to 10 g in another example, per liter of the solution.

The optimal growth temperature of the bacterium is generally in the range of 25 to 40° C. The reaction temperature is generally in the range of 25 to 40° C., or in the range of 30 to 37° C. in another example. The amount of bacterial cells in the reaction mixture can be, although it is not particularly limited, 1 to 700 g/L, 10 to 500 g/L in another example, or 20 to 400 g/L in another example. The reaction time can be 1 to 168 hours, or 3 to 72 hours in another example. The reaction can be performed batchwise or on a column.

The bacterial culture can be performed under aerobic conditions. Alternatively, the organic acid production reaction can be performed under aerobic conditions, microaerobic conditions or anaerobic conditions. For the reaction under microaerobic conditions or anaerobic conditions, the reaction can be performed by using a sealed reaction vessel without aeration, by supplying an inert gas such as nitrogen gas to the reaction mixture, or by supplying an inert gas containing carbon dioxide gas to the reaction mixture, and the like.

The organic acid that accumulates in the reaction mixture (culture medium) can be separated and purified from the reaction mixture in a conventional manner. Specifically, solids such as bacterial cells can be removed by centrifugation, filtration, or the like, and then the resulting solution can be desalted with an ion exchange resin or the like. The organic acid can be separated and purified from the solution by crystallization or column chromatography.

The collected organic acid can contain microbial cells, medium components, moisture, and by-product metabolites of the microorganism in addition to the target organic acid. Purity of the collected organic acid is 50% or higher, 85% or higher in another example, or 95% or higher in another example.

Furthermore, when the target organic acid is succinic acid, after succinic acid is produced, a polymerization reaction can be carried out by using the succinic acid as a raw material to produce a polymer containing succinic acid. In recent years, with the increase of environmentally friendly industrial products, polymers prepared from raw materials of plant origin have been attracting attention. Succinic acid can be converted into polymers such as polyesters and polyamides and used (Japanese Patent Laid-open No. 4-189822). Specific examples of succinic acid-containing polymers include succinic acid polyesters obtainable by polymerizing a diol such as butanediol and ethylene glycol, and succinic acid, succinic acid polyamides obtainable by polymerizing a diamine such as hexamethylenediamine and succinic acid, and the like. In addition, succinic acid and succinic acid-containing polymers, and compositions containing these can be used as food additives, pharmaceutical agents, cosmetics, and the like.

EXAMPLES

Hereinafter, the present invention will be explained more specifically with reference to the following non-limiting examples.

Example 1

<1-1> Acquisition of the Threonine Operon Promoter Fragment from the *Escherichia coli* MG1655 Strain The entire genomic nucleotide sequence of *Escherichia coli* (*Escherichia coli* K-12 strain) has already been elucidated (Genbank Accession No. U00096, Science, 277, 1453-1474 (1997)). On the basis of this sequence, the promoter region of the threonine operon (thrLABC) was amplified by PCR using a synthetic oligonucleotide having a SacI site (SEQ ID NO: 1) as the 5' primer, a synthetic oligonucleotide (SEQ ID NO: 2) as the 3' primer, and genomic DNA from the *Escherichia coli* MG1655 strain (ATCC 47076, ATCC 700926) as the template. As a result, the threonine operon promoter fragment (A) (SEQ ID NO: 3) was obtained.

<1-2> Acquisition of a Phosphoenolpyruvate Carboxykinase Gene Fragment from the *Actinobacillus succinogenes* 130Z Strain (ATCC 55618)

The entire genomic nucleotide sequence of the *Actinobacillus succinogenes* 130Z strain has also already been elucidated (GenBank Accession No. CP000746). Primers were designed based on the nucleotide sequence of the gene coding for PEPCK (gene name: pckA), and used to perform PCR amplification. PCR was performed by using the synthetic oligonucleotide shown in SEQ ID NO: 4 as the 5' primer, the synthetic oligonucleotide having an SacI site shown in SEQ ID NO: 5 as the 3' primer, and the genomic DNA from the *Actinobacillus succinogenes* 130Z strain as the template, to obtain a pckA gene fragment (B) (SEQ ID NO: 6).

<1-3> Construction of the Plasmid for pckA Gene Amplification

PCR was performed by using the fragments (A) and (B) as templates, and the primers of SEQ ID NOS: 1 and 5 having the SalI site to obtain a gene fragment (C) consisting of the fragments (A) and (B) ligated to each other. This gene fragment (C) was treated with the restriction enzyme SacI, purified, and the product was ligated with the plasmid vector pSTV28 (Takara Bio), which had been digested with the restriction enzyme SacI to construct a plasmid pSTV28::Pthr::pckA for pckA amplification.

<1-4> Preparation of a pckA-Amplified Strain from the *Enterobacter aerogenes* AJ110637 Strain (FERM BP-10955)

The *Enterobacter aerogenes* AJ110637 strain (FERM BP-10955, see Reference Example 1) was transformed with pSTV28::Pthr::pckA obtained above, and pSTV28 by the electric pulse method, applied to an LB agar medium containing 40 μg/ml of chloramphenicol, and cultured at 37° C. for about 18 hours. The colonies that appeared were purified, and plasmids were extracted in a conventional manner to confirm that the target plasmids were present. The obtained strains were designated *Enterobacter aerogenes* AJ110637+pSTV28::Pthr::pckA and *Enterobacter aerogenes* AJ110637+pSTV28, respectively.

Example 2

<2-1> Construction of ptsG-Deficient Strain of *Enterobacter aerogenes* AJ110637

The ptsG gene coding for glucose phosphotransferase of the *Enterobacter aerogenes* AJ110637 was deleted.

A gene fragment to be used for the deletion of ptsG was prepared by PCR using the pMW118-(λattL-Km$^r$-λattR) plasmid (see Reference Example 3) as the template, and the oligonucleotides of SEQ ID NOS: 22 and 23 as the primers. pMW118-(λattL-Km$^r$-λattR) was obtained by inserting the attL and attR genes, which are the attachment sites of λ phage, and the Km gene, which is an antibiotic resistance gene, into pMW118 (Takara Bio), in the following order: attL-Km$^r$-attR (see Reference Example 3). By PCR described above, a gene fragment containing a kanamycin resistance gene, attL and attR sequences of λ phage at the both ends of kanamycin gene, and 60 bp of the upstream sequence and 59 bp of the downstream sequence of the ptsG gene added to the outer ends of the λ phage sequences was amplified. This fragment was purified by using Wizard PCR Prep DNA Purification System (Promega).

Then, the *Enterobacter aerogenes* AJ110637 strain was transformed with RSF-Red-TER (see FIG. 1, Reference Example 2) to obtain the *Enterobacter aerogenes* AJ110637/RSF-Red-TER strain. This strain was cultured overnight in LB medium containing 40 μg/mL of chloramphenicol. Then, the culture medium was inoculated in a 1/100 volume to 50 mL of L medium containing 40 μg/mL of chloramphenicol and 0.4 mM isopropyl-β-D-thiogalactopyranoside, and a second culture was performed at 31° C. for 4 hours. The cells were collected, washed three times with ice-cooled 10% glycerol, and finally suspended in 0.5 mL of 10% glycerol. The suspended cells were used as competent cells, and 500 ng of the PCR fragment prepared in the above section was introduced into the cells by using GENE PULSER II (BioRad) under the following conditions: a field strength of 20 kV/cm, capacitor capacity of 25 μF, and resistance of 200Ω. Ice-cooled SOC medium (20 g/L of Bacto tryptone, 5 g/L of yeast extract, 0.5 g/L of NaCl, 10 g/L of glucose) was added to the cell suspension, and culture was performed at 31° C. for 2 hours with shaking. Then, the culture was applied to an LB plate containing 50 μg/mL of kanamycin. The colonies that appeared were purified on the same plate, and then it was confirmed by PCR that the ptsG gene had been replaced with the kanamycin resistance gene.

Then, in order to eliminate the RSF-Red-TER plasmid from each recombinant strain obtained as described above, the strains were applied to an LB medium containing 10% sucrose and 1 mM IPTG, and cultured overnight at 37° C. A strain lacking chloramphenicol resistance was selected as AJ110637ΔptsG from the colonies that appeared.

<2-2> Construction of a ΔptsG+pckA-Amplified Strain of *Enterobacter aerogenes* AJ110637

The *Enterobacter aerogenes* AJ110637ΔptsG strain obtained above was transformed with the pSTV28::Pthr::pckA plasmid for amplification of pckA, and pSTV28, applied to an LB agar medium containing 40 μg/ml of chloramphenicol and 50 μg/ml of kanamycin, and cultured at 37° C. for about 18 hours. The colonies that appeared were purified, and plasmids were extracted in a conventional manner to confirm that the target plasmids were present. The obtained strains were designated *Enterobacter aerogenes* AJ110637ΔptsG+pSTV28::Pthr::pckA and *Enterobacter aerogenes* AJ110637ΔptsG+pSTV28, respectively.

Example 3

Effect of ΔptsG+pckA Amplification in a Succinic Acid-Producing Strain from *Enterobacter* bacterium The *Enterobacter aerogenes* AJ110637+pSTV28, the *Enterobacter aerogenes* AJ110637ΔptsG+pSTV28, *Enterobacter aerogenes* AJ110637+pSTV28::Pthr::pckA and the *Enterobacter aerogenes* AJ110637ΔptsG+pSTV28::Pthr::pckA were each uniformly applied to an LB plate containing 40 mg/L of chloramphenicol, and cultured at 37° C. for 16 hours. Then, each plate was put into Anaeropack (for compromised culture of anaerobes, Mitsubishi Gas Chemical, product number A-04), and incubated at 37° C. for 16 hours under anaerobic conditions. The cells which appeared on the plate were washed with 0.8% brine and suspended so that the resulting cell suspension has an OD=1.0 (600 nm) after 250-times dilution. This cell suspension in a volume of 100 μl, and a production medium in a volume of 1.3 ml in which dissolved gases in the medium were replaced with carbon dioxide beforehand, were put into a 1.5-ml volume microtube, and the cells were cultured at 31.5° C. for 72 hours with shaking on a microtube shaker. The composition of the production medium is shown below.

Composition of Organic Acid Production Medium for *Enterobacter* bacteria:

Mixture A:

| | |
|---|---|
| Glucose | 20 g/L (final concentration) |
| Magnesium sulfate heptahydrate | 0.5 g/L |

Mixture B:

| | |
|---|---|
| Ammonium sulfate | 0.5 g/L |
| Potassium dihydrogenphosphate | 0.5 g/L |
| Manganese sulfate pentahydrate | 5 mg/L |
| Iron sulfate heptahydrate | 5 mg/L |
| Yeast Extract | 2 g/L |
| Biotin | 0.5 mg/L |
| (adjusted to pH 5.5 with KOH) | |

C:

| | |
|---|---|
| Calcium carbonate (Japanese Pharmacopoeia) | 50 g/L |

The ingredients of the A and B mixtures were sterilized at 115° C. for 10 minutes by autoclaving, the calcium carbonate (C) was sterilized at 180° C. for 3 hours with dry heat, and then left to cool, and A, B, and C were mixed.

After the culture, the amount of the organic acid which had accumulated in the medium was analyzed by liquid chromatography. Two Shim-pack SCR-102H (Shimadzu) columns connected in series were used, and the sample was eluted at 50° C. with 5 mM p-toluenesulfonic acid. The eluate was neutralized with 20 mM Bis-Tris aqueous solution containing 5 mM p-toluenesulfonic acid and 100 μM EDTA, and the organic acid was quantified by measuring electric conductivity with CDD-10AD (Shimadzu). The accumulated succinic acid and yield based on the consumed glucose determined after 72 hours are shown in Table 1.

TABLE 1

| | Accumulated succinic acid (g/L) | Yield based on consumed glucose (%) |
|---|---|---|
| AJ110637 + pSTV28 | 1.99 ± 0.10 | 11.4 ± 0.56 |
| AJ110637ΔptsG + pSTV28 | 0.30 ± 0.02 | 13.2 ± 0.35 |
| AJ110637 + pSTV28::Pthr::pckA | 6.29 ± 0.01 | 62.9 ± 0.55 |
| AJ110637ΔptsG + pSTV28::Pthr::pckA | 9.46 ± 0.24 | 82.8 ± 1.63 |

With only the amplification of the pckA gene, accumulation of succinic acid and yield based on consumed glucose were improved as compared to the *Enterobacter aerogenes* AJ110637+pSTV28 as a control. On the other hand, only with deletion of the ptsG gene, yield based on consumed glucose improved, but succinic acid accumulation decreased. In contrast, with the *Enterobacter aerogenes* AJ110637ΔptsG+pSTV28::Pthr::pckA, in which the pckA gene was amplified, and the ptsG gene was deleted, marked improvement was obtained for both the accumulation of succinic acid and the yield based on consumed glucose.

Reference Example 1

Acquisition of Succinic Acid-Producing Bacterium Belonging to Genus *Enterobacter*

The *Enterobacter aerogenes* AJ110637 strain was obtained from soil at the seashore of Susuki Kaigan, Makinohara-shi, Shizuoka-ken on March, 2006 by cumulative liquid culture using glycerol as the carbon source. The full-length 16S rDNA sequence was then determined, and a homology of 99.9% to that of the *Enterobacter aerogenes* NCTC 10006 strain was found. Moreover, also in a physiological test using an API kit, the strain showed results similar to the prototype species of *Enterobacter aerogenes*, and therefore the obtained isolated strain was identified as *Enterobacter aerogenes*.

Reference Example 2

Construction of the Helper Plasmid RSF-Red-TER

Figure 2:
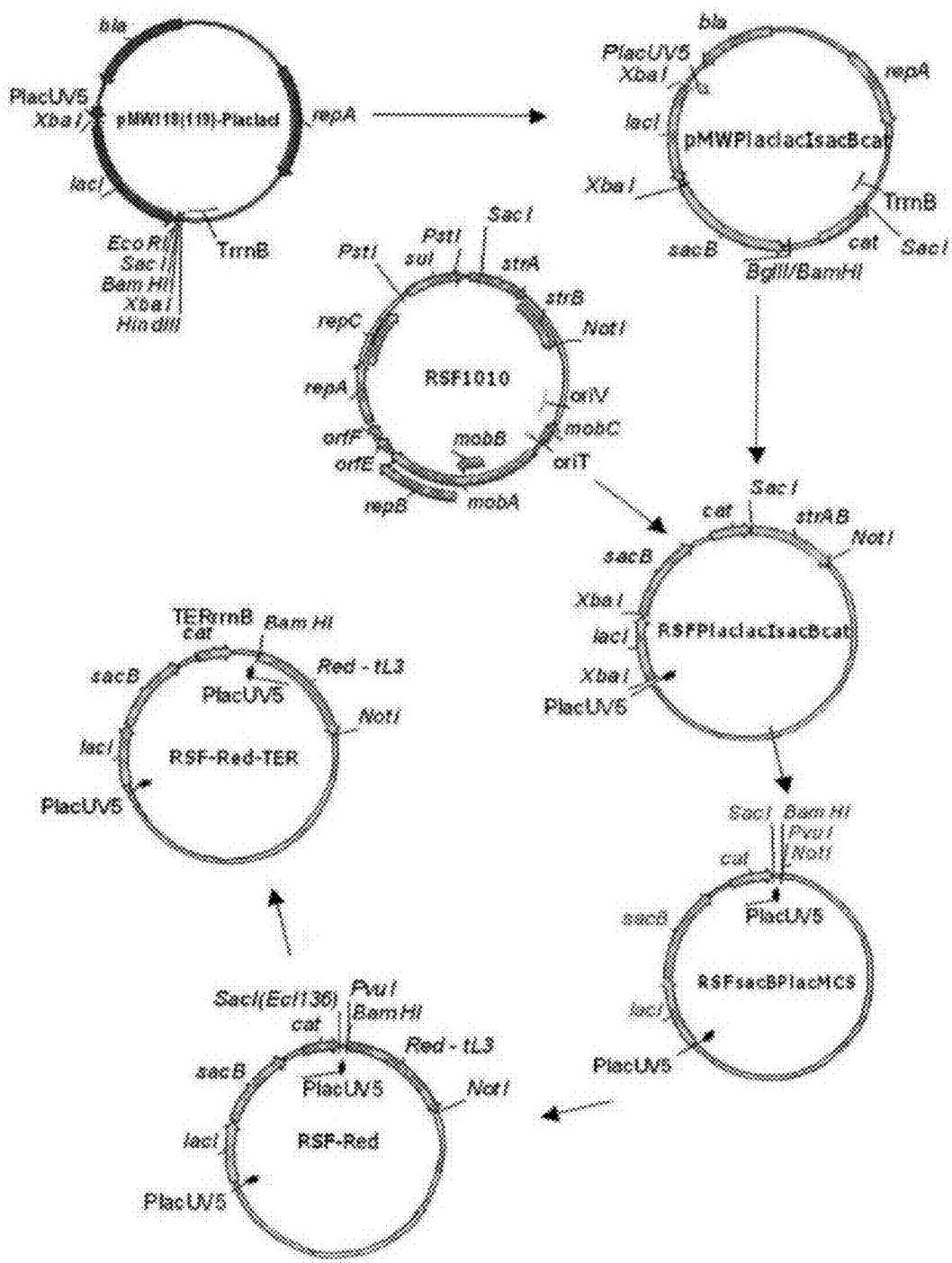
FIG. 2 shows the construction scheme of the helper plasmid RSF-Red-TER.

The scheme for constructing the helper plasmid RSF-Red-TER is shown in FIG. 2.

As the first step of the construction, an RSFsacBPlacMCS vector was designed. For this purpose, DNA fragments containing the cat gene of the pACYC184 plasmid and the structural region of the sacB gene of *Bacillus subtilis* were amplified by PCR using the oligonucleotides of SEQ ID NOS: 25 and 26, and 27 and 28, respectively. These oligonucleotides contain BglII, SacI, XbaI and BamHI restriction enzyme sites, which are required and convenient for further cloning, in the 5' end regions, respectively. The obtained sacB fragment of 1.5 kb was cloned into the previously obtained pMW119-$P_{lac}$lacI vector at the XbaI-BamHI site. This vector was constructed in the same manner as that described for the pMW118-$P_{lac}$lacI vector (Skorokhodova, A. Y. et al, 2004, Biotekhnologiya (Rus), 5:3-21). However, this vector contains a polylinker moiety derived from pMW219 instead of the pMW218 plasmid.

Then, the aforementioned cat fragment of 1.0 kb was treated with BglII and SacI, and cloned into the RSF-$P_{lac}$lacIsacB plasmid which had been obtained in the previous step at the BamHI-SacI site. The obtained plasmid pMW-$P_{lac}$lacIsacBcat contains the PlacUV5-lacI-sacB-cat fragment. In order to subclone this fragment into the RSF1010 vector, pMW-$P_{lac}$lacIsacBcat was digested with BglII, blunt-ended with DNA polymerase I Klenow fragment, and successively digested with SacI. A 3.8 kb BglII-SacI fragment of the pMWP$_{lac}$lacIsacBcat plasmid was eluted from a 1% agarose gel, and ligated with the RSF1010 vector which had been treated with PstI and SacI. *Escherichia coli* TG1 was transformed with the ligation mixture, and plated on LB medium containing chloramphenicol (50 mg/L). The plasmids isolated from the grown clones were analyzed with restriction enzymes to obtain an RSFsacB plasmid. In order to construct an RSFsacBP MCS vector, a DNA fragment containing the $P_{lacUV5}$ promoter was amplified by PCR using the oligonucleotides of SEQ ID NOS: 29 and 30 as primers and the pMW119-$P_{lac}$lacI plasmid as the template. The obtained fragment of 146 bp was digested with SacI and NocI, and ligated with the SacI-NotI large fragment of the RSFsacB plasmid. Then, by PCR using the oligonucleotides of SEQ ID NOS: 31 and 32 as primers, and the pKD46 plasmid (Datsenko, K. A., Wanner, B. L., 2000, Proc. Natl. Acad. Sci. USA, 97, 6640-6645) as the template, a DNA fragment of 2.3 kb containing the λRedαβγ genes and the transcription terminator tL3 was amplified. The obtained fragment was cloned into the RSFsacBP$_{lac}$MCS vector at the PvuI-NotI site. In this way, the RSFRed plasmid was designed.

In order to eliminate read-through transcription of the Red genes, a ρ-dependent transcription terminator from the rrnB operon of *Escherichia coli* was inserted at a position between the cat gene and the $P_{lacUV5}$ promoter. For this purpose, a DNA fragment containing the $P_{lacUV5}$ promoter and the TrrnB terminator was amplified by PCR using the oligonucleotides of SEQ ID NOS: 33 and 34 as primers and the chromosome of *Escherichia coli* BW3350 as the template. These obtained fragments were treated with KpnI and ligated. Then, the 0.5 kb fragment containing both $P_{lacUV5}$ and TrrnB was amplified by PCR using the oligonucleotides of SEQ ID NOS: 35 and 36 as primers. The obtained DNA fragment was digested with EcoRI, blunt-ended by a treatment with DNA polymerase I Klenow fragment, digested with BamHI, and ligated with the Ecl136II-BamHI large fragment of the RSFsacBPlacMCS vector. The obtained plasmid was designated RSF-Red-TER (FIG. 1).

Reference Example 3

Construction of pMW118-(λattL-Km$^r$-λattR) Plasmid

A pmW118-(λattL-Km$^r$-λattR) plasmid was constructed from the pMW118-attL-Tc-attR plasmid by substituting the kanamycin resistance gene of the pUC4K plasmid for the tetracycline resistance marker gene. For this purpose, the EcoRI-HindIII large fragment of the pMW118-attL-Tc-attR plasmid was ligated with two fragments of the pUC4K plasmid having the kanamycin resistance gene, HindIII-PstI (676 bp) and EcoRI-HindIII (585 bp) fragments. pMW118-attL-Tc-attR serving as the basic structure was obtained by ligating the following four fragments (refer to WO2005/010175).

Construction of the pMW118-attL-Tc-attR Plasmid

1) The BglII-EcoRI fragment (114 bp) which includes attL (SEQ ID NO: 37) was obtained by PCR amplification of the region corresponding to attL from the *Escherichia coli* W3350 (containing λ prophage) chromosome using the primers P1 and P2 (SEQ ID NOS: 35 and 36) (these primers contained the subsidiary recognition sites for BglII and EcoRI).

2) The PstI-HindIII fragment (182 bp) which includes attR (SEQ ID NO: 40) was obtained by PCR amplification of the region corresponding to attR from the *Escherichia coli* W3350 (containing λ pophage) chromosome using the primers P3 and P4 (SEQ ID NOS: 38 and 39) (these primers contained the subsidiary recognition sites for PstI and HindIII).

3) The BglII-HindIII large fragment (3916 bp) of pMW118-ter_rrnB. The plasmid pMW118-ter_rrnB was obtained by ligation of the following three DNA fragments:

The large DNA fragment (2359 bp) which includes the AatII-EcoRI fragment of pMW118 that was obtained by digesting pMW118 with EcoRI, treating with DNA polymerase I Klenow fragment, and then digesting with AatII;

The small AatII-BglII fragment (1194 bp) of pUC19 which includes the bla gene for ampicillin resistance (Ap$^R$) was obtained by PCR amplification of the corresponding region of the pUC19 plasmid using the primers P5 and P6 (SEQ ID NOS: 41 and 42) (these primers contained the subsidiary recognition sites for PstI, AatII and BglII);

The small BglII-PstI fragment (363 bp) of the transcription terminator ter_rrnB, which was obtained by PCR amplification of the corresponding region of the *Escherichia coli* MG1655 chromosome using the primers P7 and P8 (SEQ ID NOS: 43 and 44) (these primers contained the subsidiary recognition sites for PstI, BglII and PstI).

4) The small EcoRI-PstI fragment (1388 bp) (SEQ ID NO: 45) of pML-Tc-ter_thrL which includes the tetracycline resistance gene and the ter_thrL transcription terminator. The plasmid pML-Tc-ter_thrL was obtained by the following two steps:

the pML-ter_thrL plasmid was obtained by digesting the pML-MCS plasmid (Mashko, S. V. et al., 2001, Biotekhnologiya (in Russian), no. 5, 3-20) with XbaI and BamHI, followed by ligation of the large fragment (3342 bp) with the XbaI-BamHI fragment (68 bp) carrying ter_thrL terminator obtained by PCR amplification of the corresponding region of the *Escherichia coli* MG1655 chromosome using the primers P9 and P10 (SEQ ID NOS: 46 and 47) (these primers contained the subsidiary recognition sites for PstI, XbaI and BamHI);

the pML-Tc-ter_thrL plasmid was obtained by digesting the pML-ter_thrL plasmid with KpnI and XbaI, followed by treatment with Klenow fragment of DNA polymerase I and ligation with the small EcoRI-Van91I fragment (1317 bp) of pBR322 which includes the tetracycline resistance gene (pBR322 was digested with EcoRI and Van91I and then treated with DNA polymerase I Klenow fragment).

EXPLANATION OF SEQUENCE LISTING

SEQ ID NO: 1: Primer for amplification of threonine promoter
SEQ ID NO: 2: Primer for amplification of threonine promoter
SEQ ID NO: 3: Threonine promoter gene fragment
SEQ ID NO: 4: Primer for amplification of pckA gene of *Actinobacillus succinogenes*
SEQ ID NO: 5: Primer for amplification of pckA gene of *Actinobacillus succinogenes*
SEQ ID NO: 6: Gene sequence of pckA of *Actinobacillus succinogenes* ATCC55618 strain
SEQ ID NO: 7: Amino acid sequence of pckA of *Actinobacillus succinogenes* ATCC 55618 strain
SEQ ID NO: 8: Gene sequence of pckA of *Haemophilus influenzae* 86-028NP strain
SEQ ID NO: 9: Amino acid sequence of pckA of *Haemophilus influenzae* 86-028NP strain
SEQ ID NO: 10: Gene sequence of pckA of *Pasteurella multocida* subsp. *multocida* str. PM70 strain
SEQ ID NO: 11: Amino acid sequence of pckA of *Pasteurella multocida* subsp. *multocida* str. PM70 strain
SEQ ID NO: 12: Gene sequence of pckA of *Mannheimia succiniciproducens* MBEL55E strain
SEQ ID NO: 13: Amino acid sequence of pckA of *Mannheimia succiniciproducens* MBEL55E strain
SEQ ID NO: 14: Gene sequence of pckA of *Yersinia pseudotuberculosis* IP 32953 strain
SEQ ID NO: 15: Amino acid sequence of pckA of *Yersinia pseudotuberculosis* IP 32953 strain
SEQ ID NO: 16: Gene sequence of pckA of *Vibrio cholerae* 623-39
SEQ ID NO: 17: Amino acid sequence of pckA of *Vibrio cholerae* 623-39
SEQ ID NO: 18: Gene sequence of pckA of *Selenomonas ruminantium* subsp. *lactilytica* TH1
SEQ ID NO: 19: Amino acid sequence of pckA of *Selenomonas ruminantium* subsp. *lactilytica* TH1
SEQ ID NO: 20: Gene sequence of ptsG of *Enterobacter aerogenes* AJ110637
SEQ ID NO: 21: Amino acid sequence of ptsG of *Enterobacter aerogenes* AJ110637
SEQ ID NO: 22: Primer for deletion of ptsG
SEQ ID NO: 23: Primer for deletion of ptsG
SEQ ID NO: 24: Consensus sequence of PEPCK
SEQ ID NO: 25: Primer for amplification of cat gene
SEQ ID NO: 26: Primer for amplification of cat gene
SEQ ID NO: 27: Primer for amplification of sacB gene
SEQ ID NO: 28: Primer for amplification of sacB gene
SEQ ID NO: 29: Primer for amplification of DNA fragment containing $P_{lacUV5}$ promoter
SEQ ID NO: 30: Primer for amplification of DNA fragment containing $P_{lacUV5}$ promoter
SEQ ID NO: 31: Primer for amplification of DNA fragment containing λRedαβγ genes and tL3
SEQ ID NO: 32: Primer for amplification of DNA fragment containing λRedαβγ genes and tL3
SEQ ID NO: 33: Primer for amplification of DNA fragment containing $P_{lacUV5}$ promoter and TrrnB
SEQ ID NO: 34: Primer for amplification of DNA fragment containing $P_{lacUV5}$ promoter and TrrnB
SEQ ID NO: 35: Primer for amplification of attL
SEQ ID NO: 36: Primer for amplification of attL
SEQ ID NO: 37: Nucleotide sequence of attL
SEQ ID NO: 38: Primer for amplification of attR
SEQ ID NO: 39: Primer for amplification of attR
SEQ ID NO: 40: Nucleotide sequence of attR
SEQ ID NO: 41: Primer for amplification of DNA fragment containing bla gene
SEQ ID NO: 42: Primer for amplification of DNA fragment containing bla gene
SEQ ID NO: 43: Primer for amplification of DNA fragment containing ter_rrnB
SEQ ID NO: 44: Primer for amplification of DNA fragment containing ter_rrnB
SEQ ID NO: 45: Nucleotide sequence of DNA fragment containing ter_thrL terminator
SEQ ID NO: 46: Primer for amplification of DNA fragment containing ter_thrL terminator
SEQ ID NO: 47: Primer for amplification of DNA fragment containing ter_thrL terminator

INDUSTRIAL APPLICABILITY

According to the method of the present invention, an organic acid can be quickly and highly efficiently produced. When the organic acid is succinic acid, the obtained succinic acid can be used for food additives, pharmaceuticals, cosmetics, and the like. Moreover, succinic acid-containing polymers can also be produced by performing a polymerization reaction using the obtained succinic acid as a raw material.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an organic acid comprising: A) allowing a substance to act on an organic raw material in a reaction mixture containing carbonate ions, bicarbonate ions, or carbon dioxide gas, wherein the substance is selected from the group consisting of: (i) a bacterium belonging to the family Enterobacteriaceae which has an ability to produce an organic acid and has been modified so that the phosphoenolpyruvate carboxykinase (PckA) activity is enhanced, and the glucose phosphotransferase activity (PtsG) is decreased, (ii) a product obtained by processing the bacterium of (i), and (iii) combinations thereof; and (B) collecting the organic acid, wherein the bacterium belongs to a genus selected from the group consisting of *Escherichia, Enterobacter, Pantoea, Erwinia, Klebsiella*, and *Raoultella*; wherein the bacterium has been modified by a method selected from the group consisting of: (i) increasing the copy number of the pckA gene, (ii) modifying an expression control sequence of the pckA gene, and (iii) combinations thereof; wherein the pckA gene is selected from the group consisting of: (a) a DNA comprising a nucleotide sequence selected from the group consisting of SEQ ID NOS: 6, 8, 10, 12, 14, 16, and 18, and (b) a DNA which hybridizes with a nucleotide sequence complementary to a nucleotide sequence selected from the group consisting of SEQ ID NOS: 6, 8, 10, 12, 14, 16 and 18 under stringent conditions comprising washing at 60° C. at a salt concentration of 0.1×SSC and 0.1% SDS, and said DNA codes for a protein having phosphoenolpyruvate carboxykinase activity.

2. The method according to claim 1, wherein the pckA gene codes for a protein selected from the group consisting of:
  A) a protein comprising an amino acid sequence selected from the group consisting of SEQ ID NOS: 7, 9, 11, 13, 15, 17, 19 and 24, and
  B) a protein comprising an amino acid sequence having a homology of not less than 95% to the amino acid sequence selected from the group consisting of SEQ ID NOS: 7, 9, 11, 13, 15, 17, 19 and 24.

3. The method according to claim 1, wherein the glucose phosphotransferase activity is decreased by a method selected from the group consisting of:
  a) modifying the sequence of a gene coding for a protein of the glucose phosphotransferase system, and
  b) modifying a gene expression control region of the gene;
  wherein the gene is selected from the group consisting of ptsG, crr, ptsH and ptsI.

4. The method according to claim 1, wherein the glucose phosphotransferase activity is decreased by a method selected from the group consisting of:
  a) modifying the sequence of the ptsG gene, and
  b) modifying a gene expression control region of the ptsG gene;
  wherein the ptsG gene codes for a protein of the glucose phosphotransferase system (PTS).

5. The method according to claim 1, wherein the bacterium is *Enterobacter aerogenes*.

6. The method according to claim 1, wherein the organic acid is succinic acid.

7. A method for producing a succinic acid-containing polymer comprising:
  A) producing succinic acid by the method according to claim 6, and
  B) polymerizing the succinic acid.

* * * * *

SEQUENCE LISTING

<160> NUMBER OF SEQ ID NOS: 47

<210> SEQ ID NO 1
<211> LENGTH: 24
<212> TYPE: DNA
<213> ORGANISM: Artificial Sequence
<220> FEATURE:
<223> OTHER INFORMATION: primer for thrLABC

<400> SEQUENCE: 1
tggtcgactg gttacaacaa cgcc                                          24

<210> SEQ ID NO 2
<211> LENGTH: 35
<212> TYPE: DNA
<213> ORGANISM: Artificial Sequence
<220> FEATURE:
<223> OTHER INFORMATION: primer for thrLABC

<400> SEQUENCE: 2
acgtcattcc tccttgtcgc ctatattggt taaag                              35

<210> SEQ ID NO 3
<211> LENGTH: 290
<212> TYPE: DNA
<213> ORGANISM: Escherichia coli

<400> SEQUENCE: 3
tggtcgactg gttacaacaa cgcctggggc ttttagagca acgagacacg gcaatgttgc    60
accgtttgct gcatgatatt gaaaaaaata tcaccaaata aaaaacgcct tagtaagtat   120
ttttcagctt ttcattctga ctgcaacggg caatatgtct ctgtgtggat taaaaaaaga   180
gtgtctgata gcagcttctg aactggttac ctgccgtgag taaattaaaa ttttattgac   240
ttaggtcact aaatacttta accaatatag gcgacaagga ggaatgacgt              290

<210> SEQ ID NO 4
<211> LENGTH: 40
<212> TYPE: DNA
<213> ORGANISM: Artificial Sequence
<220> FEATURE:
<223> OTHER INFORMATION: primer for A. succinogenes pckA

<400> SEQUENCE: 4
gacaaggagg aatgacgtat gactgactta aacaaactcg                         40

<210> SEQ ID NO 5
<211> LENGTH: 28
<212> TYPE: DNA
<213> ORGANISM: Artificial Sequence
<220> FEATURE:
<223> OTHER INFORMATION: primer for A. succinogenes pckA

<400> SEQUENCE: 5
acgcgtcgac ctcagcctta tttttcag                                      28

<210> SEQ ID NO 6
<211> LENGTH: 1713
<212> TYPE: DNA
<213> ORGANISM: Actinobacillus succinogenes
<220> FEATURE:
<221> NAME/KEY: CDS
<222> LOCATION: (19)..(1635)

<400> SEQUENCE: 6

```
gacaaggagg aatgacgt atg act gac tta aac aaa ctc gtt aaa gaa ctt        51
                    Met Thr Asp Leu Asn Lys Leu Val Lys Glu Leu
                     1               5                  10 aat gac tta ggg ctt acc gat gtt aag gaa att gtg tat aac ccg agt        99
Asn Asp Leu Gly Leu Thr Asp Val Lys Glu Ile Val Tyr Asn Pro Ser
            15                  20                  25 tat gaa caa ctt ttc gag gaa gaa acc aaa ccg ggt ttg gag ggt ttc       147
Tyr Glu Gln Leu Phe Glu Glu Glu Thr Lys Pro Gly Leu Glu Gly Phe
        30                  35                  40 gat aaa ggg acg tta acc acg ctt ggc gcg gtt gcc gtc gat acg ggg       195
Asp Lys Gly Thr Leu Thr Thr Leu Gly Ala Val Ala Val Asp Thr Gly
        45                  50                  55 att ttt acc ggt cgt tca ccg aaa gat aaa tat atc gtt tgc gat gaa       243
Ile Phe Thr Gly Arg Ser Pro Lys Asp Lys Tyr Ile Val Cys Asp Glu
60              65                  70                  75 act acg aaa gac acc gtt tgg tgg aac agc gaa gcg gcg aaa aac gat       291
Thr Thr Lys Asp Thr Val Trp Trp Asn Ser Glu Ala Ala Lys Asn Asp
                80                  85                  90 aac aaa ccg atg acg caa gaa act tgg aaa agt ttg aga gaa tta gtg       339
Asn Lys Pro Met Thr Gln Glu Thr Trp Lys Ser Leu Arg Glu Leu Val
            95                 100                 105 gcg aaa caa ctt tcc ggt aaa cgt tta ttc gtg gta gaa ggt tac tgc       387
Ala Lys Gln Leu Ser Gly Lys Arg Leu Phe Val Val Glu Gly Tyr Cys
        110                 115                 120 ggc gcc agt gaa aaa cac cgt atc ggt gtg cgt atg gtt act gaa gtg       435
Gly Ala Ser Glu Lys His Arg Ile Gly Val Arg Met Val Thr Glu Val
        125                 130                 135 gca tgg cag gcg cat ttt gtg aaa aac atg ttt atc cga ccg acc gat       483
Ala Trp Gln Ala His Phe Val Lys Asn Met Phe Ile Arg Pro Thr Asp
140             145                 150                 155 gaa gag ttg aaa aat ttc aaa gcg gat ttt acc gtt tta aac ggt gct       531
Glu Glu Leu Lys Asn Phe Lys Ala Asp Phe Thr Val Leu Asn Gly Ala
                160                 165                 170 aaa tgt act aat ccg aac tgg aaa gaa caa ggt ttg aac agt gaa aac       579
Lys Cys Thr Asn Pro Asn Trp Lys Glu Gln Gly Leu Asn Ser Glu Asn
            175                 180                 185 ttt gtc gct ttc aat att acc gaa ggt att cag ctt atc ggc ggt act       627
Phe Val Ala Phe Asn Ile Thr Glu Gly Ile Gln Leu Ile Gly Gly Thr
        190                 195                 200 tgg tac ggc ggt gaa atg aaa aaa ggt atg ttc tca atg atg aac tac       675
Trp Tyr Gly Gly Glu Met Lys Lys Gly Met Phe Ser Met Met Asn Tyr
        205                 210                 215 ttc ctg ccg tta aaa ggt gtg gct tcc atg cac tgt tcc gcc aac gta       723
Phe Leu Pro Leu Lys Gly Val Ala Ser Met His Cys Ser Ala Asn Val
220             225                 230                 235 ggt aaa gac ggt gac gtg gct att ttc ttc ggt tta tcc ggt acg ggt       771
Gly Lys Asp Gly Asp Val Ala Ile Phe Phe Gly Leu Ser Gly Thr Gly
                240                 245                 250 aaa aca acg ctt tcg acc gat cct aaa cgc caa tta atc ggt gat gac       819
Lys Thr Thr Leu Ser Thr Asp Pro Lys Arg Gln Leu Ile Gly Asp Asp
            255                 260                 265 gaa cac ggt tgg gat gaa tcc ggc gta ttt aac ttt gaa ggc ggt tgt       867
Glu His Gly Trp Asp Glu Ser Gly Val Phe Asn Phe Glu Gly Gly Cys
        270                 275                 280 tac gcg aaa acc att aac tta tct caa gaa aac gaa ccg gat att tac       915
Tyr Ala Lys Thr Ile Asn Leu Ser Gln Glu Asn Glu Pro Asp Ile Tyr
        285                 290                 295 ggc gca atc cgt cgt gac gca tta tta gaa aac gtc gtg gtt cgt gca       963
Gly Ala Ile Arg Arg Asp Ala Leu Leu Glu Asn Val Val Val Arg Ala
300             305                 310                 315
```

```
gac ggt tcc gtt gac ttt gac gac ggt tca aaa aca gaa aat acc cgt    1011
Asp Gly Ser Val Asp Phe Asp Asp Gly Ser Lys Thr Glu Asn Thr Arg
            320                 325                 330 gtt tca tat ccg att tac cac atc gac aac atc gtt cgt ccg gta tcg    1059
Val Ser Tyr Pro Ile Tyr His Ile Asp Asn Ile Val Arg Pro Val Ser
        335                 340                 345 aaa gcc ggt cat gca acc aaa gtg att ttc tta acc gcg gac gca ttc    1107
Lys Ala Gly His Ala Thr Lys Val Ile Phe Leu Thr Ala Asp Ala Phe
    350                 355                 360 ggc gta ttg ccg ccg gtt tca aaa ctg act ccg gaa caa acc gaa tac    1155
Gly Val Leu Pro Pro Val Ser Lys Leu Thr Pro Glu Gln Thr Glu Tyr
365                 370                 375 tac ttc tta tcc ggc ttt act gca aaa tta gcg ggt acg gaa cgc ggc    1203
Tyr Phe Leu Ser Gly Phe Thr Ala Lys Leu Ala Gly Thr Glu Arg Gly
380                 385                 390                 395 gta acc gaa ccg act ccg aca ttc tcg gcc tgt ttc ggt gcg gca ttc    1251
Val Thr Glu Pro Thr Pro Thr Phe Ser Ala Cys Phe Gly Ala Ala Phe
            400                 405                 410 tta agc ctg cat ccg att caa tat gcg gac gtg ttg gtc gaa cgc atg    1299
Leu Ser Leu His Pro Ile Gln Tyr Ala Asp Val Leu Val Glu Arg Met
        415                 420                 425 aaa gcc tcc ggt gcg gaa gct tat ttg gtg aac acc ggt tgg aac ggc    1347
Lys Ala Ser Gly Ala Glu Ala Tyr Leu Val Asn Thr Gly Trp Asn Gly
    430                 435                 440 acg ggt aaa cgt att tca atc aaa gat acc cgc ggt att atc gat gcg    1395
Thr Gly Lys Arg Ile Ser Ile Lys Asp Thr Arg Gly Ile Ile Asp Ala
445                 450                 455 att ttg gac ggt tca atc gaa aaa gcg gaa atg ggc gaa ttg cca atc    1443
Ile Leu Asp Gly Ser Ile Glu Lys Ala Glu Met Gly Glu Leu Pro Ile
460                 465                 470                 475 ttt aat tta gcg att cct aaa gca tta ccg ggt gtt gat cct gct att    1491
Phe Asn Leu Ala Ile Pro Lys Ala Leu Pro Gly Val Asp Pro Ala Ile
            480                 485                 490 ttg gat ccg cgc gat act tac gca gac aaa gcg caa tgg caa gtt aaa    1539
Leu Asp Pro Arg Asp Thr Tyr Ala Asp Lys Ala Gln Trp Gln Val Lys
        495                 500                 505 gcg gaa gat ttg gca aac cgt ttc gtg aaa aac ttt gtg aaa tat acg    1587
Ala Glu Asp Leu Ala Asn Arg Phe Val Lys Asn Phe Val Lys Tyr Thr
    510                 515                 520 gcg aat ccg gaa gcg gct aaa tta gtt ggc gcc ggt cca aaa gca taa    1635
Ala Asn Pro Glu Ala Ala Lys Leu Val Gly Ala Gly Pro Lys Ala
525                 530                 535 aactgtaaaa gcatagtatg tgcatgattc ggtaaactac cgaataaaat ctgaaaaata   1695
aggctgaggt cgacgcgt                                                 1713

<210> SEQ ID NO 7
<211> LENGTH: 538
<212> TYPE: PRT
<213> ORGANISM: Actinobacillus succinogenes

<400> SEQUENCE: 7

Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60
```

```
Ser Pro Lys Asp Lys Tyr Ile Val Cys Asp Glu Thr Thr Lys Asp Thr
 65                  70                  75                  80

Val Trp Trp Asn Ser Glu Ala Ala Lys Asn Asp Asn Lys Pro Met Thr
                 85                  90                  95

Gln Glu Thr Trp Lys Ser Leu Arg Glu Leu Val Ala Lys Gln Leu Ser
            100                 105                 110

Gly Lys Arg Leu Phe Val Val Glu Gly Tyr Cys Gly Ala Ser Glu Lys
        115                 120                 125

His Arg Ile Gly Val Arg Met Val Thr Glu Val Ala Trp Gln Ala His
    130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Glu Ser Gly Val Phe Asn Phe Glu Gly Gly Cys Tyr Ala Lys Thr Ile
        275                 280                 285

Asn Leu Ser Gln Glu Asn Glu Pro Asp Ile Tyr Gly Ala Ile Arg Arg
    290                 295                 300

Asp Ala Leu Leu Glu Asn Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
            340                 345                 350

Thr Lys Val Ile Phe Leu Thr Ala Asp Ala Phe Gly Val Leu Pro Pro
        355                 360                 365

Val Ser Lys Leu Thr Pro Glu Gln Thr Glu Tyr Tyr Phe Leu Ser Gly
370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
```

```
                         485                 490                 495
Thr Tyr Ala Asp Lys Ala Gln Trp Gln Val Lys Ala Glu Asp Leu Ala
                500                 505                 510

Asn Arg Phe Val Lys Asn Phe Val Lys Tyr Thr Ala Asn Pro Glu Ala
            515                 520                 525

Ala Lys Leu Val Gly Ala Gly Pro Lys Ala
        530                 535

<210> SEQ ID NO 8
<211> LENGTH: 1617
<212> TYPE: DNA
<213> ORGANISM: Haemophilus influenzae
<220> FEATURE:
<221> NAME/KEY: CDS
<222> LOCATION: (1)..(1617)

<400> SEQUENCE: 8 atg aca gac tta aat aaa gtg gta aaa gaa ctt gaa gct ctt ggc att      48
Met Thr Asp Leu Asn Lys Val Val Lys Glu Leu Glu Ala Leu Gly Ile
1               5                   10                  15 tat gac gta aaa gaa gtt gtt tac aat cca agc tac gag caa ttg ttc      96
Tyr Asp Val Lys Glu Val Val Tyr Asn Pro Ser Tyr Glu Gln Leu Phe
            20                  25                  30 gaa gaa gaa act aaa cca ggc tta gaa ggc ttt gaa aaa ggt act tta     144
Glu Glu Glu Thr Lys Pro Gly Leu Glu Gly Phe Glu Lys Gly Thr Leu
        35                  40                  45 act acg act ggt gca gtg gca gta gat aca ggt atc ttc aca ggt cgt     192
Thr Thr Thr Gly Ala Val Ala Val Asp Thr Gly Ile Phe Thr Gly Arg
    50                  55                  60 tct cca aaa gat aaa tat atc gtg tta gat gaa aaa acc aaa gat act     240
Ser Pro Lys Asp Lys Tyr Ile Val Leu Asp Glu Lys Thr Lys Asp Thr
65                  70                  75                  80 gtt tgg tgg aca tct gaa aca gca aaa aac gac aac aag cca atg aac     288
Val Trp Trp Thr Ser Glu Thr Ala Lys Asn Asp Asn Lys Pro Met Asn
                85                  90                  95 caa gct aca tgg caa agc tta aaa gac ttg gta acc aac caa ctt tct     336
Gln Ala Thr Trp Gln Ser Leu Lys Asp Leu Val Thr Asn Gln Leu Ser
            100                 105                 110 cgt aaa cgc tta ttt gta gtt gat ggt ttc tgt ggt gcg agc gaa cac     384
Arg Lys Arg Leu Phe Val Val Asp Gly Phe Cys Gly Ala Ser Glu His
        115                 120                 125 gac cgt att gca gta cgt att gtc act gaa gta gcg tgg caa gca cat     432
Asp Arg Ile Ala Val Arg Ile Val Thr Glu Val Ala Trp Gln Ala His
    130                 135                 140 ttt gta aaa aat atg ttt att cgc cca act gaa gaa caa ctc aaa aat     480
Phe Val Lys Asn Met Phe Ile Arg Pro Thr Glu Glu Gln Leu Lys Asn
145                 150                 155                 160 ttt gaa cca gat ttc gtt gta atg aac ggt tct aaa gta acc aat cca     528
Phe Glu Pro Asp Phe Val Val Met Asn Gly Ser Lys Val Thr Asn Pro
                165                 170                 175 aac tgg aaa gaa caa ggt tta aat tca gaa aac ttt gtt gct ttc aac     576
Asn Trp Lys Glu Gln Gly Leu Asn Ser Glu Asn Phe Val Ala Phe Asn
            180                 185                 190 ttg act gaa cgc att caa tta atc ggc ggt act tgg tac ggc ggc gaa     624
Leu Thr Glu Arg Ile Gln Leu Ile Gly Gly Thr Trp Tyr Gly Gly Glu
        195                 200                 205 atg aaa aaa ggt atg ttc tca atg atg aac tac ttc cta cct ctc aaa     672
Met Lys Lys Gly Met Phe Ser Met Met Asn Tyr Phe Leu Pro Leu Lys
    210                 215                 220 ggt gtt ggt gca atg cac tgc tca gct aac gtt ggt aaa gat ggt gat     720
Gly Val Gly Ala Met His Cys Ser Ala Asn Val Gly Lys Asp Gly Asp
```

```
                225                 230                 235                 240
gta gca atc ttc ttc ggc tta tct ggc aca ggt aaa aca acc ctt tca         768
Val Ala Ile Phe Phe Gly Leu Ser Gly Thr Gly Lys Thr Thr Leu Ser
                    245                 250                 255 acg gat cca aaa cgt gaa tta atc ggt gac gat gaa cac ggt tgg gat         816
Thr Asp Pro Lys Arg Glu Leu Ile Gly Asp Asp Glu His Gly Trp Asp
            260                 265                 270 gat gtt ggt atc ttt aac ttt gaa ggt ggt tgt tat gcg aaa acc att         864
Asp Val Gly Ile Phe Asn Phe Glu Gly Gly Cys Tyr Ala Lys Thr Ile
        275                 280                 285 cat ctt tca gaa gaa aat gaa cca gat att tac cac gct atc cgt cgc         912
His Leu Ser Glu Glu Asn Glu Pro Asp Ile Tyr His Ala Ile Arg Arg
    290                 295                 300 gac gca tta tta gaa aac gtg gtt gtt cgt tca gat ggt tct gtt gat         960
Asp Ala Leu Leu Glu Asn Val Val Val Arg Ser Asp Gly Ser Val Asp
305                 310                 315                 320 ttc gat gat ggt tca aaa aca gaa aat act cgc gtg tct tac cca att        1008
Phe Asp Asp Gly Ser Lys Thr Glu Asn Thr Arg Val Ser Tyr Pro Ile
                325                 330                 335 tat cac atc gat aac att gta aaa cca gtt tct cgt gca ggt cac gca        1056
Tyr His Ile Asp Asn Ile Val Lys Pro Val Ser Arg Ala Gly His Ala
            340                 345                 350 act aaa gtg att ttc tta act gca gat gcg ttt ggt gta tta cct cca        1104
Thr Lys Val Ile Phe Leu Thr Ala Asp Ala Phe Gly Val Leu Pro Pro
        355                 360                 365 gta tct aaa ttg aca cca gaa caa act aaa tac tac ttc tta tct ggt        1152
Val Ser Lys Leu Thr Pro Glu Gln Thr Lys Tyr Tyr Phe Leu Ser Gly
    370                 375                 380 ttc aca gcg aaa tta gca ggg act gaa cgt ggt att act gaa cca acg        1200
Phe Thr Ala Lys Leu Ala Gly Thr Glu Arg Gly Ile Thr Glu Pro Thr
385                 390                 395                 400 cca act ttc tca gca tgt ttc ggt gca gca ttt tta acg ctt cat cca        1248
Pro Thr Phe Ser Ala Cys Phe Gly Ala Ala Phe Leu Thr Leu His Pro
                405                 410                 415 act caa tat gca gaa gtg tta gta aaa cgt atg caa gca gca ggt gct        1296
Thr Gln Tyr Ala Glu Val Leu Val Lys Arg Met Gln Ala Ala Gly Ala
            420                 425                 430 gaa gct tac tta gtg aat act ggt tgg aat ggc aca ggc aaa cgt atc        1344
Glu Ala Tyr Leu Val Asn Thr Gly Trp Asn Gly Thr Gly Lys Arg Ile
        435                 440                 445 tca atc aaa gat act cgc gga atc att gat gca atc tta gat ggc tca        1392
Ser Ile Lys Asp Thr Arg Gly Ile Ile Asp Ala Ile Leu Asp Gly Ser
    450                 455                 460 att gaa aaa gct gaa atg ggc gaa ttg cca atc ttc aac tta gca att        1440
Ile Glu Lys Ala Glu Met Gly Glu Leu Pro Ile Phe Asn Leu Ala Ile
465                 470                 475                 480 cct aaa gca tta cca ggt gta gat tct gca atc tta gat cct cgc gat        1488
Pro Lys Ala Leu Pro Gly Val Asp Ser Ala Ile Leu Asp Pro Arg Asp
                485                 490                 495 act tac gca gat aaa gca caa tgg caa tca aaa gct gaa gac tta gca        1536
Thr Tyr Ala Asp Lys Ala Gln Trp Gln Ser Lys Ala Glu Asp Leu Ala
            500                 505                 510 ggt cgt ttt gtg aaa aac ttt gtt aaa tat gca act aac gaa gaa ggc        1584
Gly Arg Phe Val Lys Asn Phe Val Lys Tyr Ala Thr Asn Glu Glu Gly
        515                 520                 525 aaa gct tta att gca gct ggt cct aaa gct taa                            1617
Lys Ala Leu Ile Ala Ala Gly Pro Lys Ala
    530                 535

<210> SEQ ID NO 9
```

<211> LENGTH: 538
<212> TYPE: PRT
<213> ORGANISM: Haemophilus influenzae

<400> SEQUENCE: 9

```
Met Thr Asp Leu Asn Lys Val Val Lys Glu Leu Glu Ala Leu Gly Ile
1               5                   10                  15

Tyr Asp Val Lys Glu Val Val Tyr Asn Pro Ser Tyr Glu Gln Leu Phe
            20                  25                  30

Glu Glu Glu Thr Lys Pro Gly Leu Glu Gly Phe Glu Lys Gly Thr Leu
        35                  40                  45

Thr Thr Thr Gly Ala Val Ala Val Asp Thr Gly Ile Phe Thr Gly Arg
50                  55                  60

Ser Pro Lys Asp Lys Tyr Ile Val Leu Asp Glu Lys Thr Lys Asp Thr
65                  70                  75                  80

Val Trp Trp Thr Ser Glu Thr Ala Lys Asn Asp Asn Lys Pro Met Asn
                85                  90                  95

Gln Ala Thr Trp Gln Ser Leu Lys Asp Leu Val Thr Asn Gln Leu Ser
            100                 105                 110

Arg Lys Arg Leu Phe Val Val Asp Gly Phe Cys Gly Ala Ser Glu His
        115                 120                 125

Asp Arg Ile Ala Val Arg Ile Val Thr Glu Val Ala Trp Gln Ala His
130                 135                 140

Phe Val Lys Asn Met Phe Ile Arg Pro Thr Glu Glu Gln Leu Lys Asn
145                 150                 155                 160

Phe Glu Pro Asp Phe Val Val Met Asn Gly Ser Lys Val Thr Asn Pro
                165                 170                 175

Asn Trp Lys Glu Gln Gly Leu Asn Ser Glu Asn Phe Val Ala Phe Asn
            180                 185                 190

Leu Thr Glu Arg Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
210                 215                 220

Gly Val Gly Ala Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Glu Leu Ile Gly Asp Asp Glu His Gly Trp Asp
            260                 265                 270

Asp Val Gly Ile Phe Asn Phe Glu Gly Gly Cys Tyr Ala Lys Thr Ile
        275                 280                 285

His Leu Ser Glu Glu Asn Glu Pro Asp Ile Tyr His Ala Ile Arg Arg
290                 295                 300

Asp Ala Leu Leu Glu Asn Val Val Val Arg Ser Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Lys Pro Val Ser Arg Ala Gly His Ala
            340                 345                 350

Thr Lys Val Ile Phe Leu Thr Ala Asp Ala Phe Gly Val Leu Pro Pro
        355                 360                 365

Val Ser Lys Leu Thr Pro Glu Gln Thr Lys Tyr Tyr Phe Leu Ser Gly
370                 375                 380

Phe Thr Ala Lys Leu Ala Gly Thr Glu Arg Gly Ile Thr Glu Pro Thr
385                 390                 395                 400
```

```
Pro Thr Phe Ser Ala Cys Phe Gly Ala Ala Phe Leu Thr Leu His Pro
                405                 410                 415
Thr Gln Tyr Ala Glu Val Leu Val Lys Arg Met Gln Ala Ala Gly Ala
            420                 425                 430
Glu Ala Tyr Leu Val Asn Thr Gly Trp Asn Gly Thr Gly Lys Arg Ile
        435                 440                 445
Ser Ile Lys Asp Thr Arg Gly Ile Ile Asp Ala Ile Leu Asp Gly Ser
    450                 455                 460
Ile Glu Lys Ala Glu Met Gly Glu Leu Pro Ile Phe Asn Leu Ala Ile
465                 470                 475                 480
Pro Lys Ala Leu Pro Gly Val Asp Ser Ala Ile Leu Asp Pro Arg Asp
                485                 490                 495
Thr Tyr Ala Asp Lys Ala Gln Trp Gln Ser Lys Ala Glu Asp Leu Ala
            500                 505                 510
Gly Arg Phe Val Lys Asn Phe Val Lys Tyr Ala Thr Asn Glu Glu Gly
        515                 520                 525
Lys Ala Leu Ile Ala Ala Gly Pro Lys Ala
    530                 535

<210> SEQ ID NO 10
<211> LENGTH: 1617
<212> TYPE: DNA
<213> ORGANISM: Pasteurella multocida
<220> FEATURE:
<221> NAME/KEY: CDS
<222> LOCATION: (1)..(1617)

<400> SEQUENCE: 10 atg act gac tta aat aaa gta atc aat gaa ctt ggt gca ctt ggt att      48
Met Thr Asp Leu Asn Lys Val Ile Asn Glu Leu Gly Ala Leu Gly

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Phe | Lys | Pro | Asp | Phe | Val | Val | Met | Asn | Gly | Ser | Lys | Val | Thr | Asn | Pro | |
|     |     |     |     | 165 |     |     |     | 170 |     |     |     | 175 |     |     |     | |

```
aac tgg aaa gaa caa ggt cta aat tct gaa aac ttt gtg gca ttt aac      576
Asn Trp Lys Glu Gln Gly Leu Asn Ser Glu Asn Phe Val Ala Phe Asn
        180                 185                 190 tta act gaa ggc gtg caa tta atc ggt ggt act tgg tac ggc ggt gaa      624
Leu Thr Glu Gly Val Gln Leu Ile Gly Gly Thr Trp Tyr Gly Gly Glu
            195                 200                 205 atg aaa aaa ggt atg ttc tca atg atg aac tac ttc tta cca tta aaa      672
Met Lys Lys Gly Met Phe Ser Met Met Asn Tyr Phe Leu Pro Leu Lys
    210                 215                 220 ggc atc gca tct atg cac tgt tca gcc aac gtg ggt gaa aaa ggc gac      720
Gly Ile Ala Ser Met His Cys Ser Ala Asn Val Gly Glu Lys Gly Asp
225                 230                 235                 240 gtt gct gtg ttc ttc ggt tta tca ggt aca ggt aaa acc acc ctt tca      768
Val Ala Val Phe Phe Gly Leu Ser Gly Thr Gly Lys Thr Thr Leu Ser
                245                 250                 255 aca gat cca aaa cgt caa tta atc ggt gac gat gag cac ggt tgg gat      816
Thr Asp Pro Lys Arg Gln Leu Ile Gly Asp Asp Glu His Gly Trp Asp
            260                 265                 270 gat gat ggc gta ttc aac tac gaa ggt ggt tgc tat gcg aaa acg atc      864
Asp Asp Gly Val Phe Asn Tyr Glu Gly Gly Cys Tyr Ala Lys Thr Ile
        275                 280                 285 aaa ctg tct cca gaa aac gaa cca gat atc tat aaa gcc atc aaa cgt      912
Lys Leu Ser Pro Glu Asn Glu Pro Asp Ile Tyr Lys Ala Ile Lys Arg
290                 295                 300 gat gcc tta tta gaa aac gtt gta gta cgt gca gat ggt tca gtg gat      960
Asp Ala Leu Leu Glu Asn Val Val Val Arg Ala Asp Gly Ser Val Asp
305                 310                 315                 320 tac gat gat ggt tca aaa aca gaa aac acc cgt gtt tct tac cca att     1008
Tyr Asp Asp Gly Ser Lys Thr Glu Asn Thr Arg Val Ser Tyr Pro Ile
                325                 330                 335 tac cac atc gac aac atc gta aca ccg gta tca aaa gca ggt cat gcg     1056
Tyr His Ile Asp Asn Ile Val Thr Pro Val Ser Lys Ala Gly His Ala
            340                 345                 350 aaa aaa gtg atc ttc tta act gcg gac gca ttc ggt gtg tta cca cca     1104
Lys Lys Val Ile Phe Leu Thr Ala Asp Ala Phe Gly Val Leu Pro Pro
        355                 360                 365 gta tct aaa tta acg cca gaa caa act aaa tac tac ttc tta tct ggt     1152
Val Ser Lys Leu Thr Pro Glu Gln Thr Lys Tyr Tyr Phe Leu Ser Gly
370                 375                 380 ttc acc gcg aaa tta gcc ggt act gag cgt ggt atc aca gaa cca aca     1200
Phe Thr Ala Lys Leu Ala Gly Thr Glu Arg Gly Ile Thr Glu Pro Thr
385                 390                 395                 400 cca acg ttc tct gca tgt ttc ggt gca gcg ttc tta tca ctt cac cca     1248
Pro Thr Phe Ser Ala Cys Phe Gly Ala Ala Phe Leu Ser Leu His Pro
                405                 410                 415 aca caa tat gcg gaa gtg tta gtg aaa cgt atg gaa gca gcg ggt gcg     1296
Thr Gln Tyr Ala Glu Val Leu Val Lys Arg Met Glu Ala Ala Gly Ala
            420                 425                 430 gaa gct tac tta gtg aac aca ggt tgg aac ggt aca ggt aaa cgt atc     1344
Glu Ala Tyr Leu Val Asn Thr Gly Trp Asn Gly Thr Gly Lys Arg Ile
        435                 440                 445 tca atc aaa gat acg cgc ggt atc atc gat gca atc tta gac ggt tca     1392
Ser Ile Lys Asp Thr Arg Gly Ile Ile Asp Ala Ile Leu Asp Gly Ser
450                 455                 460 atc gaa aaa gca gaa atg ggc aaa tta cca atc ttt gat tta gcg atc     1440
Ile Glu Lys Ala Glu Met Gly Lys Leu Pro Ile Phe Asp Leu Ala Ile
465                 470                 475                 480 cca act gca tta cca ggt gtt gac cct gca atc tta gat cca cgt gat     1488
```

```
Pro Thr Ala Leu Pro Gly Val Asp Pro Ala Ile Leu Asp Pro Arg Asp
            485                 490                 495 act tat gca gac aaa gca caa tgg caa gcg aaa gca gaa gac tta gct    1536
Thr Tyr Ala Asp Lys Ala Gln Trp Gln Ala Lys Ala Glu Asp Leu Ala
            500                 505                 510 ggt cgt ttc gtg aaa aac ttc gaa aaa tac acc act aac gat gaa ggt    1584
Gly Arg Phe Val Lys Asn Phe Glu Lys Tyr Thr Thr Asn Asp Glu Gly
            515                 520                 525 aaa gca tta gtg gca gca ggt cca aaa gcg taa                        1617
Lys Ala Leu Val Ala Ala Gly Pro Lys Ala
            530                 535

<210> SEQ ID NO 11
<211> LENGTH: 538
<212> TYPE: PRT
<213> ORGANISM: Pasteurella multocida

<400> SEQUENCE: 11

Met Thr Asp Leu Asn Lys Val Ile Asn Glu Leu Gly Ala Leu Gly Ile
  1               5                  10                  15

His Asp Val Lys Glu Ile Val Tyr Asn Pro Ser Tyr Glu Gln Leu Phe
               20                  25                  30

Glu Glu Glu Thr Lys Pro Gly Leu Glu Gly Tyr Glu Lys Gly Ile Val
           35                  40                  45

Thr Gln Ser Gly Ala Val Ala Val Asp Thr Gly Ile Phe Thr Gly Arg
       50                  55                  60

Ser Pro Lys Asp Lys Tyr Ile Val Leu Asp Lys Thr Lys Asp Thr
 65                  70                  75                  80

Val Trp Trp Thr Ser Asp Ala Ala Lys Asn Asp Asn Lys Pro Met Thr
                 85                  90                  95

Gln Asp Thr Trp Lys Ser Leu Lys Gly Leu Val Thr Glu Gln Leu Ser
            100                 105                 110

Gly Lys Arg Leu Phe Val Ile Asp Ala Phe Cys Gly Ala Asn Ala Asp
        115                 120                 125

Thr Arg Leu Ser Val Arg Ile Val Thr Glu Val Ala Trp Gln Ala His
    130                 135                 140

Phe Val Lys Asn Met Phe Ile Arg Pro Thr Glu Ala Glu Leu Val Gly
145                 150                 155                 160

Phe Lys Pro Asp Phe Val Val Met Asn Gly Ser Lys Val Thr Asn Pro
                165                 170                 175

Asn Trp Lys Glu Gln Gly Leu Asn Ser Glu Asn Phe Val Ala Phe Asn
            180                 185                 190

Leu Thr Glu Gly Val Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
    210                 215                 220

Gly Ile Ala Ser Met His Cys Ser Ala Asn Val Gly Glu Lys Gly Asp
225                 230                 235                 240

Val Ala Val Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Asp Asp Gly Val Phe Asn Tyr Glu Gly Gly Cys Tyr Ala Lys Thr Ile
        275                 280                 285

Lys Leu Ser Pro Glu Asn Glu Pro Asp Ile Tyr Lys Ala Ile Lys Arg
    290                 295                 300
```

```
Asp Ala Leu Leu Glu Asn Val Val Arg Ala Asp Gly Ser Val Asp
305                 310                 315                 320

Tyr Asp Asp Gly Ser Lys Thr Glu Asn Thr Arg Val Ser Tyr Pro Ile
            325                 330                 335

Tyr His Ile Asp Asn Ile Val Thr Pro Val Ser Lys Ala Gly His Ala
        340                 345                 350

Lys Lys Val Ile Phe Leu Thr Ala Asp Ala Phe Gly Val Leu Pro Pro
    355                 360                 365

Val Ser Lys Leu Thr Pro Glu Gln Thr Lys Tyr Tyr Phe Leu Ser Gly
370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Ala Ala Phe Leu Ser Leu His Pro
            405                 410                 415

Thr Gln Tyr Ala Glu Val Leu Val Lys Arg Met Glu Ala Ala Gly Ala
        420                 425                 430

Glu Ala Tyr Leu Val Asn Thr Gly Trp Asn Gly Thr Gly Lys Arg Ile
    435                 440                 445

Ser Ile Lys Asp Thr Arg Gly Ile Ile Asp Ala Ile Leu Asp Gly Ser
450                 455                 460

Ile Glu Lys Ala Glu Met Gly Lys Leu Pro Ile Phe Asp Leu Ala Ile
465                 470                 475                 480

Pro Thr Ala Leu Pro Gly Val Asp Pro Ala Ile Leu Asp Pro Arg Asp
            485                 490                 495

Thr Tyr Ala Asp Lys Ala Gln Trp Gln Ala Lys Ala Glu Asp Leu Ala
        500                 505                 510

Gly Arg Phe Val Lys Asn Phe Glu Lys Tyr Thr Thr Asn Asp Glu Gly
    515                 520                 525

Lys Ala Leu Val Ala Ala Gly Pro Lys Ala
530                 535

<210> SEQ ID NO 12
<211> LENGTH: 1617
<212> TYPE: DNA
<213> ORGANISM: Mannheimia succiniciproducens
<220> FEATURE:
<221> NAME/KEY: CDS
<222> LOCATION: (1)..(1617)

<400> SEQUENCE: 12 atg aca gat ctt aat caa tta act caa gaa ctt ggt gct tta ggt att      48
Met Thr Asp Leu Asn Gln Leu Thr Gln Glu Leu Gly Ala Leu Gly Ile
1               5                   10                  15 cat gat gta caa gaa gtt gtg tat aac ccg agc tat gaa ctt ctt ttt      96
His Asp Val Gln Glu Val Val Tyr Asn Pro Ser Tyr Glu Leu Leu Phe
                20                  25                  30 gcg gaa gaa acc aaa cca ggt tta gaa ggt tat gaa aaa ggt act gtg     144
Ala Glu Glu Thr Lys Pro Gly Leu Glu Gly Tyr Glu Lys Gly Thr Val
            35                  40                  45 act aat caa gga gcg gtt gct gta aat acc ggt att ttc acc ggt cgt     192
Thr Asn Gln Gly Ala Val Ala Val Asn Thr Gly Ile Phe Thr Gly Arg
        50                  55                  60 tct ccg aaa gat aaa tat atc gtt tta gac gac aaa act aaa gat acc     240
Ser Pro Lys Asp Lys Tyr Ile Val Leu Asp Asp Lys Thr Lys Asp Thr
65                  70                  75                  80 gta tgg tgg acc agc gaa aaa gtt aaa aac gat aac aaa cca atg agc     288
Val Trp Trp Thr Ser Glu Lys Val Lys Asn Asp Asn Lys Pro Met Ser
                85                  90                  95
```

```
caa gat acc tgg aac agt ttg aaa ggt tta gtt gcc gat caa ctt tcc      336
Gln Asp Thr Trp Asn Ser Leu Lys Gly Leu Val Ala Asp Gln Leu Ser
            100                 105                 110 ggt aaa cgt tta ttt gtt gtt gac gca ttc tgc ggc gcg aat aaa gat      384
Gly Lys Arg Leu Phe Val Val Asp Ala Phe Cys Gly Ala Asn Lys Asp
        115                 120                 125 acg cgt tta gct gtt cgt gtg gtt act gaa gtt gca tgg cag gcg cat      432
Thr Arg Leu Ala Val Arg Val Val Thr Glu Val Ala Trp Gln Ala His
    130                 135                 140 ttt gta aca aat atg ttt atc cgc cct tca gcg gaa gaa tta aaa ggt      480
Phe Val Thr Asn Met Phe Ile Arg Pro Ser Ala Glu Glu Leu Lys Gly
145                 150                 155                 160 ttc aaa cct gat ttc gtg gta atg aac ggt gca aaa tgt aca aat cct      528
Phe Lys Pro Asp Phe Val Val Met Asn Gly Ala Lys Cys Thr Asn Pro
                165                 170                 175 aac tgg aaa gaa caa ggg tta aat tcc gaa aac ttc gtt gcg ttc aac      576
Asn Trp Lys Glu Gln Gly Leu Asn Ser Glu Asn Phe Val Ala Phe Asn
            180                 185                 190 att aca gaa ggc gtt caa tta atc ggc ggt act tgg tac ggt ggt gaa      624
Ile Thr Glu Gly Val Gln Leu Ile Gly Gly Thr Trp Tyr Gly Gly Glu
        195                 200                 205 atg aaa aaa ggt atg ttc tca atg atg aac tac ttc tta ccg ctt cgt      672
Met Lys Lys Gly Met Phe Ser Met Met Asn Tyr Phe Leu Pro Leu Arg
    210                 215                 220 ggt att gca tca atg cac tgt tcc gca aac gtt ggt aaa gac ggc gat      720
Gly Ile Ala Ser Met His Cys Ser Ala Asn Val Gly Lys Asp Gly Asp
225                 230                 235                 240 acc gca att ttc ttc ggt ttg tca ggc aca ggt aaa acg aca tta tca      768
Thr Ala Ile Phe Phe Gly Leu Ser Gly Thr Gly Lys Thr Thr Leu Ser
                245                 250                 255 aca gat cct aaa cgt caa cta atc ggt gat gac gaa cac ggt tgg gac      816
Thr Asp Pro Lys Arg Gln Leu Ile Gly Asp Asp Glu His Gly Trp Asp
            260                 265                 270 gat gaa ggc gta ttt aac ttc gaa ggt ggt tgc tac gcg aaa acc att      864
Asp Glu Gly Val Phe Asn Phe Glu Gly Gly Cys Tyr Ala Lys Thr Ile
        275                 280                 285 aac tta tcc gct gaa aac gag ccg gat atc tat ggc gct atc aaa cgt      912
Asn Leu Ser Ala Glu Asn Glu Pro Asp Ile Tyr Gly Ala Ile Lys Arg
    290                 295                 300 gac gca tta ttg gaa aac gtg gtt gtt tta gat aac ggt gac gtt gac      960
Asp Ala Leu Leu Glu Asn Val Val Val Leu Asp Asn Gly Asp Val Asp
305                 310                 315                 320 tat gca gac ggt tcc aaa aca gaa aat aca cgt gtt tct tat ccg att     1008
Tyr Ala Asp Gly Ser Lys Thr Glu Asn Thr Arg Val Ser Tyr Pro Ile
                325                 330                 335 tat cac att caa aat atc gtt aaa cct gtt tct aaa gct ggt ccg gca     1056
Tyr His Ile Gln Asn Ile Val Lys Pro Val Ser Lys Ala Gly Pro Ala
            340                 345                 350 act aaa gtt atc ttc ttg tct gcc gat gca ttc ggt gta tta ccg ccg     1104
Thr Lys Val Ile Phe Leu Ser Ala Asp Ala Phe Gly Val Leu Pro Pro
        355                 360                 365 gtg tct aaa tta act ccg gaa caa acc aaa tac tat ttc tta tcc ggt     1152
Val Ser Lys Leu Thr Pro Glu Gln Thr Lys Tyr Tyr Phe Leu Ser Gly
    370                 375                 380 ttc act gcg aaa tta gcg ggt acg gaa cgc ggt att aca gag cct aca     1200
Phe Thr Ala Lys Leu Ala Gly Thr Glu Arg Gly Ile Thr Glu Pro Thr
385                 390                 395                 400 cca aca ttc tct gca tgt ttt ggt gcg gct ttt tta agc ttg cat ccg     1248
Pro Thr Phe Ser Ala Cys Phe Gly Ala Ala Phe Leu Ser Leu His Pro
                405                 410                 415
```

```
aca caa tat gcc gaa gtg tta gta aaa cgt atg caa gaa tca ggt gcg    1296
Thr Gln Tyr Ala Glu Val Leu Val Lys Arg Met Gln Glu Ser Gly Ala
            420                 425                 430 gaa gcg tat ctt gtt aat aca ggt tgg aac ggt acc ggc aaa cgt atc    1344
Glu Ala Tyr Leu Val Asn Thr Gly Trp Asn Gly Thr Gly Lys Arg Ile
        435                 440                 445 tca att aaa gat acc cgt ggt att att gat gca att tta gac ggc tca    1392
Ser Ile Lys Asp Thr Arg Gly Ile Ile Asp Ala Ile Leu Asp Gly Ser
    450                 455                 460 att gat aaa gcg gaa atg ggc tca tta cca atc ttc gat ttc tca att    1440
Ile Asp Lys Ala Glu Met Gly Ser Leu Pro Ile Phe Asp Phe Ser Ile
465                 470                 475                 480 cct aaa gca tta cct ggt gtt aac cct gca atc tta gat ccg cgc gat    1488
Pro Lys Ala Leu Pro Gly Val Asn Pro Ala Ile Leu Asp Pro Arg Asp
            485                 490                 495 act tat gcg gat aaa gcg caa tgg gaa gaa aaa gct caa gat ctt gca    1536
Thr Tyr Ala Asp Lys Ala Gln Trp Glu Glu Lys Ala Gln Asp Leu Ala
        500                 505                 510 ggt cgc ttt gtg aaa aac ttt gaa aaa tat acc ggt acg gcg gaa ggt    1584
Gly Arg Phe Val Lys Asn Phe Glu Lys Tyr Thr Gly Thr Ala Glu Gly
    515                 520                 525 cag gca tta gtt gct gcc ggt cct aaa gca taa                        1617
Gln Ala Leu Val Ala Ala Gly Pro Lys Ala
530                 535

<210> SEQ ID NO 13
<211> LENGTH: 538
<212> TYPE: PRT
<213> ORGANISM: Mannheimia succiniciproducens

<400> SEQUENCE: 13

Met Thr Asp Leu Asn Gln Leu Thr Gln Glu Leu Gly Ala Leu Gly Ile
1               5                   10                  15

His Asp Val Gln Glu Val Val Tyr Asn Pro Ser Tyr Glu Leu Leu Phe
            20                  25                  30

Ala Glu Glu Thr Lys Pro Gly Leu Glu Gly Tyr Glu Lys Gly Thr Val
        35                  40                  45

Thr Asn Gln Gly Ala Val Ala Val Asn Thr Gly Ile Phe Thr Gly Arg
    50                  55                  60

Ser Pro Lys Asp Lys Tyr Ile Val Leu Asp Asp Lys Thr Lys Asp Thr
65                  70                  75                  80

Val Trp Trp Thr Ser Glu Lys Val Lys Asn Asp Asn Lys Pro Met Ser
                85                  90                  95

Gln Asp Thr Trp Asn Ser Leu Lys Gly Leu Val Ala Asp Gln Leu Ser
            100                 105                 110

Gly Lys Arg Leu Phe Val Val Asp Ala Phe Cys Gly Ala Asn Lys Asp
        115                 120                 125

Thr Arg Leu Ala Val Arg Val Val Thr Glu Val Ala Trp Gln Ala His
    130                 135                 140

Phe Val Thr Asn Met Phe Ile Arg Pro Ser Ala Glu Glu Leu Lys Gly
145                 150                 155                 160

Phe Lys Pro Asp Phe Val Val Met Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Val Gln Leu Ile Gly Gly Thr Trp Tyr Gly Gly Glu
        195                 200                 205

Met Lys Lys Gly Met Phe Ser Met Met Asn Tyr Phe Leu Pro Leu Arg
```

```
                210                 215                 220
Gly Ile Ala Ser Met His Cys Ser Ala Asn Val Gly Lys Asp Gly Asp
225                 230                 235                 240

Thr Ala Ile Phe Phe Gly Leu Ser Gly Thr Gly Lys Thr Thr Leu Ser
            245                 250                 255

Thr Asp Pro Lys Arg Gln Leu Ile Gly Asp Glu His Gly Trp Asp
        260                 265                 270

Asp Glu Gly Val Phe Asn Phe Gly Gly Cys Tyr Ala Lys Thr Ile
            275                 280                 285

Asn Leu Ser Ala Glu Asn Glu Pro Asp Ile Tyr Gly Ala Ile Lys Arg
290                 295                 300

Asp Ala Leu Leu Glu Asn Val Val Leu Asp Asn Gly Asp Val Asp
305                 310                 315                 320

Tyr Ala Asp Gly Ser Lys Thr Glu Asn Thr Arg Val Ser Tyr Pro Ile
            325                 330                 335

Tyr His Ile Gln Asn Ile Val Lys Pro Val Ser Lys Ala Gly Pro Ala
            340                 345                 350

Thr Lys Val Ile Phe Leu Ser Ala Asp Ala Phe Gly Val Leu Pro Pro
        355                 360                 365

Val Ser Lys Leu Thr Pro Glu Gln Thr Lys Tyr Tyr Phe Leu Ser Gly
370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Ala Ala Phe Leu Ser Leu His Pro
            405                 410                 415

Thr Gln Tyr Ala Glu Val Leu Val Lys Arg Met Gln Glu Ser Gly Ala
        420                 425                 430

Glu Ala Tyr Leu Val Asn Thr Gly Trp Asn Gly Thr Gly Lys Arg Ile
            435                 440                 445

Ser Ile Lys Asp Thr Arg Gly Ile Ile Asp Ala Ile Leu Asp Gly Ser
450                 455                 460

Ile Asp Lys Ala Glu Met Gly Ser Leu Pro Ile Phe Asp Phe Ser Ile
465                 470                 475                 480

Pro Lys Ala Leu Pro Gly Val Asn Pro Ala Ile Leu Asp Pro Arg Asp
            485                 490                 495

Thr Tyr Ala Asp Lys Ala Gln Trp Glu Lys Ala Gln Asp Leu Ala
        500                 505                 510

Gly Arg Phe Val Lys Asn Phe Glu Lys Tyr Thr Gly Thr Ala Glu Gly
            515                 520                 525

Gln Ala Leu Val Ala Ala Gly Pro Lys Ala
530                 535

<210> SEQ ID NO 14
<211> LENGTH: 1620
<212> TYPE: DNA
<213> ORGANISM: Yersinia pseudotuberculosis
<220> FEATURE:
<221> NAME/KEY: CDS
<222> LOCATION: (1)..(1620)

<400> SEQUENCE: 14 atg agt gtt aaa gga att acc ccg cag gag ctc gcc gcc tat ggc atc      48
Met Ser Val Lys Gly Ile Thr Pro Gln Glu Leu Ala Ala Tyr Gly Ile
1               5                   10                  15 cat aac gtc agc gag att gtt tac aac cca agc tat gat tta ctg ttt      96
His Asn Val Ser Glu Ile Val Tyr Asn Pro Ser Tyr Asp Leu Leu Phe
            20                  25                  30
```

```
gaa gaa gag acc aaa ccc acg ttg gaa gga tac gaa cgt ggc aca ctg      144
Glu Glu Glu Thr Lys Pro Thr Leu Glu Gly Tyr Glu Arg Gly Thr Leu
         35                  40                  45 acg act acc ggc gca ata gcg gta gat acc ggt att ttt acc ggg cgt      192
Thr Thr Thr Gly Ala Ile Ala Val Asp Thr Gly Ile Phe Thr Gly Arg
 50                  55                  60 tca ccc aaa gat aaa tat att gtc cgc gat gct atc act cag gat acc      240
Ser Pro Lys Asp Lys Tyr Ile Val Arg Asp Ala Ile Thr Gln Asp Thr
65                  70                  75                  80 gtg tgg tgg gcc gat cag ggc aaa ggt aaa aat gat aat aag cct ctg      288
Val Trp Trp Ala Asp Gln Gly Lys Gly Lys Asn Asp Asn Lys Pro Leu
                 85                  90                  95 agc caa gag atc tgg agc cat ttg aaa ggt ctg gtg acg gaa caa ctc      336
Ser Gln Glu Ile Trp Ser His Leu Lys Gly Leu Val Thr Glu Gln Leu
            100                 105                 110 tct ggc aaa cgc ctc ttt gtt gtc gat aca ttc tgc ggt gct aat gcg      384
Ser Gly Lys Arg Leu Phe Val Val Asp Thr Phe Cys Gly Ala Asn Ala
        115                 120                 125 gat acc cgc ctg caa gtc cgc ttt atc aca gaa gtc gct tgg cag gca      432
Asp Thr Arg Leu Gln Val Arg Phe Ile Thr Glu Val Ala Trp Gln Ala
130                 135                 140 cac ttc gtc aaa aat atg ttt atc cgt cca tca gat gaa gaa ctg gct      480
His Phe Val Lys Asn Met Phe Ile Arg Pro Ser Asp Glu Glu Leu Ala
145                 150                 155                 160 cgg ttt gaa cct gac ttt atc gtg atg aac ggt gcc aaa tgc act aac      528
Arg Phe Glu Pro Asp Phe Ile Val Met Asn Gly Ala Lys Cys Thr Asn
                165                 170                 175 cca caa tgg aaa gag cag ggc ctg aat tca gaa aac ttt gtc gcc ttt      576
Pro Gln Trp Lys Glu Gln Gly Leu Asn Ser Glu Asn Phe Val Ala Phe
            180                 185                 190 aat ctg aca gaa cgt atg cag ttg att ggt ggc acg tgg tat ggc ggc      624
Asn Leu Thr Glu Arg Met Gln Leu Ile Gly Gly Thr Trp Tyr Gly Gly
        195                 200                 205 gaa atg aag aaa ggg atg ttc tca atg atg aac tac ctg ctg cca ctg      672
Glu Met Lys Lys Gly Met Phe Ser Met Met Asn Tyr Leu Leu Pro Leu
210                 215                 220 aaa ggc att gct tca atg cat tgt tca gct aac gtc ggc gaa aaa ggc      720
Lys Gly Ile Ala Ser Met His Cys Ser Ala Asn Val Gly Glu Lys Gly
225                 230                 235                 240 gat gtt gcc atc ttc ttc ggt ctg tcg ggt acc ggt aaa acc act tta      768
Asp Val Ala Ile Phe Phe Gly Leu Ser Gly Thr Gly Lys Thr Thr Leu
                245                 250                 255 tct acc gat cca aaa cgc aag ttg atc ggt gat gat gaa cat ggc tgg      816
Ser Thr Asp Pro Lys Arg Lys Leu Ile Gly Asp Asp Glu His Gly Trp
            260                 265                 270 gat gat gat ggc gtc ttt aac ttc gag ggg ggg tgc tac gct aaa acc      864
Asp Asp Asp Gly Val Phe Asn Phe Glu Gly Gly Cys Tyr Ala Lys Thr
        275                 280                 285 atc aag tta tct gaa gaa gca gag cca gat att tac cac gcc att aaa      912
Ile Lys Leu Ser Glu Glu Ala Glu Pro Asp Ile Tyr His Ala Ile Lys
290                 295                 300 cgc gac gcc ttg ctg gaa aac gtg gtg gtg cta gca gac ggt acc gtt      960
Arg Asp Ala Leu Leu Glu Asn Val Val Val Leu Ala Asp Gly Thr Val
305                 310                 315                 320 gat ttt aat gac ggt tct aaa act gaa aac acc cgt gtc tct tat ccg     1008
Asp Phe Asn Asp Gly Ser Lys Thr Glu Asn Thr Arg Val Ser Tyr Pro
                325                 330                 335 att tac cac att gat aac att gtt aaa ccg gtg tcc aaa gca ggc cat     1056
Ile Tyr His Ile Asp Asn Ile Val Lys Pro Val Ser Lys Ala Gly His
            340                 345                 350
```

-continued

```
gcg acc aag gtt atc ttc ctg act gcc gat gcc ttt ggt gtg ctc ccc    1104
Ala Thr Lys Val Ile Phe Leu Thr Ala Asp Ala Phe Gly Val Leu Pro
        355                 360                 365 cca gta tct cgt ctg acc gca aac cag acg caa tat cac ttc ctc tct    1152
Pro Val Ser Arg Leu Thr Ala Asn Gln Thr Gln Tyr His Phe Leu Ser
    370                 375                 380 ggc ttt act gcc aaa ctg gca ggg aca gag cgt ggc gtc acg gag cca    1200
Gly Phe Thr Ala Lys Leu Ala Gly Thr Glu Arg Gly Val Thr Glu Pro
385                 390                 395                 400 aca cca acc ttc tct gct tgc ttt ggt gcg gcc ttc ctg tct ctg cac    1248
Thr Pro Thr Phe Ser Ala Cys Phe Gly Ala Ala Phe Leu Ser Leu His
                405                 410                 415 cca acg cag tac gct gaa gtg ctg gtt aag cgt atg caa gcg gtt ggc    1296
Pro Thr Gln Tyr Ala Glu Val Leu Val Lys Arg Met Gln Ala Val Gly
            420                 425                 430 gca caa gcc tat ctg gtc aat acc ggt tgg aac ggg aca ggt aag cgt    1344
Ala Gln Ala Tyr Leu Val Asn Thr Gly Trp Asn Gly Thr Gly Lys Arg
        435                 440                 445 att tcc atc aag gat acc cgc gcc att att gac gca atc cta aac ggg    1392
Ile Ser Ile Lys Asp Thr Arg Ala Ile Ile Asp Ala Ile Leu Asn Gly
    450                 455                 460 gag att gat aag gca gaa acc ttt acg ctg cca atc ttt gat ctg gca    1440
Glu Ile Asp Lys Ala Glu Thr Phe Thr Leu Pro Ile Phe Asp Leu Ala
465                 470                 475                 480 gtc cct atg gcg tta ccc ggt gtg aat ccc gat atc ctc gat cct cgc    1488
Val Pro Met Ala Leu Pro Gly Val Asn Pro Asp Ile Leu Asp Pro Arg
                485                 490                 495 gac acc tac gcc gat aaa gcg caa tgg caa gag aaa gcc gaa gat ttg    1536
Asp Thr Tyr Ala Asp Lys Ala Gln Trp Gln Glu Lys Ala Glu Asp Leu
            500                 505                 510 gcg aaa cgc ttt gcg act aac ttt gat aaa tac act gat acc cct gcg    1584
Ala Lys Arg Phe Ala Thr Asn Phe Asp Lys Tyr Thr Asp Thr Pro Ala
        515                 520                 525 ggg gcc gcg ttg gtt agc gcg ggg cca aag atc taa                    1620
Gly Ala Ala Leu Val Ser Ala Gly Pro Lys Ile
    530                 535
```

<210> SEQ ID NO 15
<211> LENGTH: 539
<212> TYPE: PRT
<213> ORGANISM: Yersinia pseudotuberculosis

<400> SEQUENCE: 15

```
Met Ser Val Lys Gly Ile Thr Pro Gln Glu Leu Ala Ala Tyr Gly Ile
1               5                   10                  15

His Asn Val Ser Glu Ile Val Tyr Asn Pro Ser Tyr Asp Leu Leu Phe
            20                  25                  30

Glu Glu Glu Thr Lys Pro Thr Leu Glu Gly Tyr Glu Arg Gly Thr Leu
        35                  40                  45

Thr Thr Thr Gly Ala Ile Ala Val Asp Thr Gly Ile Phe Thr Gly Arg
    50                  55                  60

Ser Pro Lys Asp Lys Tyr Ile Val Arg Asp Ala Ile Thr Gln Asp Thr
65                  70                  75                  80

Val Trp Trp Ala Asp Gln Gly Lys Gly Lys Asn Asp Asn Lys Pro Leu
                85                  90                  95

Ser Gln Glu Ile Trp Ser His Leu Lys Gly Leu Val Thr Glu Gln Leu
            100                 105                 110

Ser Gly Lys Arg Leu Phe Val Val Asp Thr Phe Cys Gly Ala Asn Ala
        115                 120                 125
```

-continued

Asp Thr Arg Leu Gln Val Arg Phe Ile Thr Glu Val Ala Trp Gln Ala
130                 135                 140

His Phe Val Lys Asn Met Phe Ile Arg Pro Ser Asp Glu Glu Leu Ala
145                 150                 155                 160

Arg Phe Glu Pro Asp Phe Ile Val Met Asn Gly Ala Lys Cys Thr Asn
                165                 170                 175

Pro Gln Trp Lys Glu Gln Gly Leu Asn Ser Glu Asn Phe Val Ala Phe
            180                 185                 190

Asn Leu Thr Glu Arg Met Gln Leu Ile Gly Gly Thr Trp Tyr Gly Gly
        195                 200                 205

Glu Met Lys Lys Gly Met Phe Ser Met Met Asn Tyr Leu Leu Pro Leu
    210                 215                 220

Lys Gly Ile Ala Ser Met His Cys Ser Ala Asn Val Gly Glu Lys Gly
225                 230                 235                 240

Asp Val Ala Ile Phe Phe Gly Leu Ser Gly Thr Gly Lys Thr Thr Leu
                245                 250                 255

Ser Thr Asp Pro Lys Arg Lys Leu Ile Gly Asp Asp Glu His Gly Trp
            260                 265                 270

Asp Asp Asp Gly Val Phe Asn Phe Glu Gly Gly Cys Tyr Ala Lys Thr
        275                 280                 285

Ile Lys Leu Ser Glu Glu Ala Glu Pro Asp Ile Tyr His Ala Ile Lys
    290                 295                 300

Arg Asp Ala Leu Leu Glu Asn Val Val Val Leu Ala Asp Gly Thr Val
305                 310                 315                 320

Asp Phe Asn Asp Gly Ser Lys Thr Glu Asn Thr Arg Val Ser Tyr Pro
                325                 330                 335

Ile Tyr His Ile Asp Asn Ile Val Lys Pro Val Ser Lys Ala Gly His
            340                 345                 350

Ala Thr Lys Val Ile Phe Leu Thr Ala Asp Ala Phe Gly Val Leu Pro
        355                 360                 365

Pro Val Ser Arg Leu Thr Ala Asn Gln Thr Gln Tyr His Phe Leu Ser
    370                 375                 380

Gly Phe Thr Ala Lys Leu Ala Gly Thr Glu Arg Gly Val Thr Glu Pro
385                 390                 395                 400

Thr Pro Thr Phe Ser Ala Cys Phe Gly Ala Ala Phe Leu Ser Leu His
                405                 410                 415

Pro Thr Gln Tyr Ala Glu Val Leu Val Lys Arg Met Gln Ala Val Gly
            420                 425                 430

Ala Gln Ala Tyr Leu Val Asn Thr Gly Trp Asn Gly Thr Gly Lys Arg
        435                 440                 445

Ile Ser Ile Lys Asp Thr Arg Ala Ile Asp Ala Ile Leu Asn Gly
    450                 455                 460

Glu Ile Asp Lys Ala Glu Thr Phe Thr Leu Pro Ile Phe Asp Leu Ala
465                 470                 475                 480

Val Pro Met Ala Leu Pro Gly Val Asn Pro Asp Ile Leu Asp Pro Arg
                485                 490                 495

Asp Thr Tyr Ala Asp Lys Ala Gln Trp Gln Glu Lys Ala Glu Asp Leu
            500                 505                 510

Ala Lys Arg Phe Ala Thr Asn Phe Asp Lys Tyr Thr Asp Thr Pro Ala
        515                 520                 525

Gly Ala Ala Leu Val Ser Ala Gly Pro Lys Ile
    530                 535

<210> SEQ ID NO 16
<211> LENGTH: 1629
<212> TYPE: DNA
<213> ORGANISM: Vibrio cholerae
<220> FEATURE:
<221> NAME/KEY: CDS
<222> LOCATION: (1)..(1629)

<400> SEQUENCE: 16

| | | | | | | | | | | | | | | | | |
|---|---|---|---|---|---|---|---|---|---|---|---|---|---|---|---|---|
| atg | acc | gtt | atg | gaa | cat | act | aag | gct | gca | caa | atc | gac | cta | gcc | caa | 48 |
| Met | Thr | Val | Met | Glu | His | Thr | Lys | Ala | Ala | Gln | Ile | Asp | Leu | Ala | Gln | |
| 1 | | | | 5 | | | | | 10 | | | | | 15 | | |
| tat | ggg | atc | acc | ggc | gta | act | gaa | ctg | gtt | cgt | aac | ccg | agc | tat | gaa | 96 |
| Tyr | Gly | Ile | Thr | Gly | Val | Thr | Glu | Leu | Val | Arg | Asn | Pro | Ser | Tyr | Glu | |
| | | | 20 | | | | | 25 | | | | | 30 | | | |
| atg | tta | ttt | gcc | gaa | gaa | acc | cgt | tca | gat | ctc | gaa | ggt | tat | gaa | cgt | 144 |
| Met | Leu | Phe | Ala | Glu | Glu | Thr | Arg | Ser | Asp | Leu | Glu | Gly | Tyr | Glu | Arg | |
| | 35 | | | | | 40 | | | | | 45 | | | | | |
| ggt | gtg | gtg | act | gaa | ttg | ggt | gct | gtt | gcg | gtt | gat | act | ggc | atc | ttc | 192 |
| Gly | Val | Val | Thr | Glu | Leu | Gly | Ala | Val | Ala | Val | Asp | Thr | Gly | Ile | Phe | |
| 50 | | | | | 55 | | | | | 60 | | | | | | |
| act | ggc | cgc | tca | cca | aaa | gat | aag | ttt | atc | gtt | aaa | gat | gat | acc | act | 240 |
| Thr | Gly | Arg | Ser | Pro | Lys | Asp | Lys | Phe | Ile | Val | Lys | Asp | Asp | Thr | Thr | |
| 65 | | | | 70 | | | | | 75 | | | | | 80 | | |
| cgc | gat | acg | ctg | tgg | tgg | acg | tca | gac | aaa | gcg | aaa | aac | gac | aac | aaa | 288 |
| Arg | Asp | Thr | Leu | Trp | Trp | Thr | Ser | Asp | Lys | Ala | Lys | Asn | Asp | Asn | Lys | |
| | | | | 85 | | | | | 90 | | | | | 95 | | |
| ccg | atc | aat | caa | gaa | gtg | tgg | aat | gac | ctg | aaa | gcc | ttg | gtg | acc | aag | 336 |
| Pro | Ile | Asn | Gln | Glu | Val | Trp | Asn | Asp | Leu | Lys | Ala | Leu | Val | Thr | Lys | |
| | | | 100 | | | | | 105 | | | | | 110 | | | |
| cag | ctt | tct | ggt | aaa | cgc | gta | ttt | gtg | ctc | gat | ggc | tac | tgt | ggt | gcc | 384 |
| Gln | Leu | Ser | Gly | Lys | Arg | Val | Phe | Val | Leu | Asp | Gly | Tyr | Cys | Gly | Ala | |
| | | 115 | | | | | 120 | | | | | 125 | | | | |
| aac | gcc | gat | act | cgc | tta | agt | gtt | cgc | ttc | atc | acc | gaa | gta | gca | tgg | 432 |
| Asn | Ala | Asp | Thr | Arg | Leu | Ser | Val | Arg | Phe | Ile | Thr | Glu | Val | Ala | Trp | |
| | 130 | | | | | 135 | | | | | 140 | | | | | |
| caa | gca | cac | ttt | gtg | aaa | aac | atg | ttc | att | cgt | cca | agc | gaa | gaa | gag | 480 |
| Gln | Ala | His | Phe | Val | Lys | Asn | Met | Phe | Ile | Arg | Pro | Ser | Glu | Glu | Glu | |
| 145 | | | | | 150 | | | | | 155 | | | | | 160 | |
| ctg | gca | cac | ttt | aaa | cca | gac | ttt | gtc | gta | atg | aac | ggc | gca | aaa | tgt | 528 |
| Leu | Ala | His | Phe | Lys | Pro | Asp | Phe | Val | Val | Met | Asn | Gly | Ala | Lys | Cys | |
| | | | | 165 | | | | | 170 | | | | | 175 | | |
| acc | aat | gcg | aag | tgg | aaa | gag | cac | ggt | ctg | aac | tca | gaa | aac | ttc | act | 576 |
| Thr | Asn | Ala | Lys | Trp | Lys | Glu | His | Gly | Leu | Asn | Ser | Glu | Asn | Phe | Thr | |
| | | | 180 | | | | | 185 | | | | | 190 | | | |
| gtg | ttt | aac | ctg | acc | gag | cgc | atg | cag | ctc | atc | ggc | ggt | act | tgg | tac | 624 |
| Val | Phe | Asn | Leu | Thr | Glu | Arg | Met | Gln | Leu | Ile | Gly | Gly | Thr | Trp | Tyr | |
| | | 195 | | | | | 200 | | | | | 205 | | | | |
| ggc | ggt | gag | atg | aaa | aaa | ggt | atg | ttc | gcg | atg | atg | aac | tac | ttc | ctg | 672 |
| Gly | Gly | Glu | Met | Lys | Lys | Gly | Met | Phe | Ala | Met | Met | Asn | Tyr | Phe | Leu | |
| | 210 | | | | | 215 | | | | | 220 | | | | | |
| ccg | cta | caa | ggc | att | gcc | tct | atg | cac | tgc | tct | gcc | aac | atg | ggt | aaa | 720 |
| Pro | Leu | Gln | Gly | Ile | Ala | Ser | Met | His | Cys | Ser | Ala | Asn | Met | Gly | Lys | |
| 225 | | | | | 230 | | | | | 235 | | | | | 240 | |
| gcg | ggc | gat | gtc | gcc | atc | ttc | ttc | ggt | ctt | tct | ggt | acg | ggt | aaa | acc | 768 |
| Ala | Gly | Asp | Val | Ala | Ile | Phe | Phe | Gly | Leu | Ser | Gly | Thr | Gly | Lys | Thr | |
| | | | | 245 | | | | | 250 | | | | | 255 | | |
| acc | cta | tcc | acc | gat | cca | aaa | cgt | gcg | tta | att | ggt | gac | gat | gag | cac | 816 |
| Thr | Leu | Ser | Thr | Asp | Pro | Lys | Arg | Ala | Leu | Ile | Gly | Asp | Asp | Glu | His | |
| | | | 260 | | | | | 265 | | | | | 270 | | | |
| ggc | tgg | gat | gat | gat | ggc | gtg | ttc | aac | ttt | gaa | ggc | ggc | tgc | tac | gcg | 864 |
| Gly | Trp | Asp | Asp | Asp | Gly | Val | Phe | Asn | Phe | Glu | Gly | Gly | Cys | Tyr | Ala | |

```
aaa acc atc aag ctg tct aaa gaa gca gag ccg gat atc tat aac gcg     912
Lys Thr Ile Lys Leu Ser Lys Glu Ala Glu Pro Asp Ile Tyr Asn Ala
290                 295                 300 atc cgc cgt gat gct cta ctg gaa aac gtc acg gtt cgt agt gat ggt     960
Ile Arg Arg Asp Ala Leu Leu Glu Asn Val Thr Val Arg Ser Asp Gly
305                 310                 315                 320 tcg att gat ttt gat gat ggt tca aaa acc gag aac acc cgt gtt tct    1008
Ser Ile Asp Phe Asp Asp Gly Ser Lys Thr Glu Asn Thr Arg Val Ser
            325                 330                 335 tac cct att tat cac atc gac aac atc gta aaa ccc gtt tcc aaa ggc    1056
Tyr Pro Ile Tyr His Ile Asp Asn Ile Val Lys Pro Val Ser Lys Gly
340                 345                 350 ggt cat gcg act aag gtg atc ttc ctg tct gcc gat gcg ttt ggc gta    1104
Gly His Ala Thr Lys Val Ile Phe Leu Ser Ala Asp Ala Phe Gly Val
        355                 360                 365 ttg cct cca gtt tca aaa ctg acg cca gag caa acc aag tac cac ttc    1152
Leu Pro Pro Val Ser Lys Leu Thr Pro Glu Gln Thr Lys Tyr His Phe
370                 375                 380 ttg tct ggc ttt acg gct aaa ctg gca ggt act gag cgt ggc att act    1200
Leu Ser Gly Phe Thr Ala Lys Leu Ala Gly Thr Glu Arg Gly Ile Thr
385                 390                 395                 400 gaa cct acc cca acc ttc tcc gcc tgt ttt ggc gca gcg ttc ctc act    1248
Glu Pro Thr Pro Thr Phe Ser Ala Cys Phe Gly Ala Ala Phe Leu Thr
            405                 410                 415 ctg cac cca act cag tat gca gaa gtg ctg gta aaa cgt atg gaa gca    1296
Leu His Pro Thr Gln Tyr Ala Glu Val Leu Val Lys Arg Met Glu Ala
        420                 425                 430 gcg ggc gcc gaa gcc tat ctg gtt aac aca ggt tgg aac ggc agc ggt    1344
Ala Gly Ala Glu Ala Tyr Leu Val Asn Thr Gly Trp Asn Gly Ser Gly
435                 440                 445 aag cgc atc tca att aaa gat acg cgc ggt att atc gat gcg att ttg    1392
Lys Arg Ile Ser Ile Lys Asp Thr Arg Gly Ile Ile Asp Ala Ile Leu
450                 455                 460 gat ggt tcg atc gaa aaa gcg gaa acc aaa cag atc cca atc ttt aat    1440
Asp Gly Ser Ile Glu Lys Ala Glu Thr Lys Gln Ile Pro Ile Phe Asn
465                 470                 475                 480 ctg caa gtg ccc acc gca ctg ccc ggc gtc gat cct atg atc ctc gac    1488
Leu Gln Val Pro Thr Ala Leu Pro Gly Val Asp Pro Met Ile Leu Asp
            485                 490                 495 cca cgt gat act tat gtt gac cca ctg cag tgg gaa agc aaa gcc aaa    1536
Pro Arg Asp Thr Tyr Val Asp Pro Leu Gln Trp Glu Ser Lys Ala Lys
        500                 505                 510 gac ttg gca acg cgc ttc atc aac aac ttc gac aag tac acg gat aac    1584
Asp Leu Ala Thr Arg Phe Ile Asn Asn Phe Asp Lys Tyr Thr Asp Asn
515                 520                 525 gcc gaa ggt aaa gca ctg gtt gcc gcg ggt cca aag ctc gac taa        1629
Ala Glu Gly Lys Ala Leu Val Ala Ala Gly Pro Lys Leu Asp
530                 535                 540

<210> SEQ ID NO 17
<211> LENGTH: 542
<212> TYPE: PRT
<213> ORGANISM: Vibrio cholerae

<400> SEQUENCE: 17

Met Thr Val Met Glu His Thr Lys Ala Ala Gln Ile Asp Leu Ala Gln
1               5                   10                  15

Tyr Gly Ile Thr Gly Val Thr Glu Leu Val Arg Asn Pro Ser Tyr Glu
            20                  25                  30
```

-continued

Met Leu Phe Ala Glu Glu Thr Arg Ser Asp Leu Glu Gly Tyr Glu Arg
        35                  40                  45

Gly Val Val Thr Glu Leu Gly Ala Val Ala Val Asp Thr Gly Ile Phe
 50                  55                  60

Thr Gly Arg Ser Pro Lys Asp Lys Phe Ile Val Lys Asp Asp Thr Thr
 65                  70                  75                  80

Arg Asp Thr Leu Trp Trp Thr Ser Asp Lys Ala Lys Asn Asp Asn Lys
                 85                  90                  95

Pro Ile Asn Gln Glu Val Trp Asn Asp Leu Lys Ala Leu Val Thr Lys
                100                 105                 110

Gln Leu Ser Gly Lys Arg Val Phe Val Leu Asp Gly Tyr Cys Gly Ala
        115                 120                 125

Asn Ala Asp Thr Arg Leu Ser Val Arg Phe Ile Thr Glu Val Ala Trp
130                 135                 140

Gln Ala His Phe Val Lys Asn Met Phe Ile Arg Pro Ser Glu Glu Glu
145                 150                 155                 160

Leu Ala His Phe Lys Pro Asp Phe Val Met Asn Gly Ala Lys Cys
                165                 170                 175

Thr Asn Ala Lys Trp Lys Glu His Gly Leu Asn Ser Gly Asn Phe Thr
                180                 185                 190

Val Phe Asn Leu Thr Glu Arg Met Gln Leu Ile Gly Gly Thr Trp Tyr
        195                 200                 205

Gly Gly Glu Met Lys Lys Gly Met Phe Ala Met Met Asn Tyr Phe Leu
210                 215                 220

Pro Leu Gln Gly Ile Ala Ser Met His Cys Ser Ala Asn Met Gly Lys
225                 230                 235                 240

Ala Gly Asp Val Ala Ile Phe Phe Gly Leu Ser Gly Thr Gly Lys Thr
                245                 250                 255

Thr Leu Ser Thr Asp Pro Lys Arg Ala Leu Ile Gly Asp Asp Glu His
                260                 265                 270

Gly Trp Asp Asp Asp Gly Val Phe Asn Phe Glu Gly Gly Cys Tyr Ala
        275                 280                 285

Lys Thr Ile Lys Leu Ser Lys Glu Ala Glu Pro Asp Ile Tyr Asn Ala
290                 295                 300

Ile Arg Arg Asp Ala Leu Leu Glu Asn Val Thr Val Arg Ser Asp Gly
305                 310                 315                 320

Ser Ile Asp Phe Asp Asp Gly Ser Lys Thr Glu Asn Thr Arg Val Ser
                325                 330                 335

Tyr Pro Ile Tyr His Ile Asp Asn Ile Val Lys Pro Val Ser Lys Gly
        340                 345                 350

Gly His Ala Thr Lys Val Ile Phe Leu Ser Ala Asp Ala Phe Gly Val
        355                 360                 365

Leu Pro Pro Val Ser Lys Leu Thr Pro Glu Gln Thr Lys Tyr His Phe
370                 375                 380

Leu Ser Gly Phe Thr Ala Lys Leu Ala Gly Thr Glu Arg Gly Ile Thr
385                 390                 395                 400

Glu Pro Thr Pro Thr Phe Ser Ala Cys Phe Gly Ala Ala Phe Leu Thr
                405                 410                 415

Leu His Pro Thr Gln Tyr Ala Glu Val Leu Val Lys Arg Met Glu Ala
                420                 425                 430

Ala Gly Ala Glu Ala Tyr Leu Val Asn Thr Gly Trp Asn Gly Ser Gly
        435                 440                 445

Lys Arg Ile Ser Ile Lys Asp Thr Arg Gly Ile Ile Asp Ala Ile Leu
450                 455                 460

```
Asp Gly Ser Ile Glu Lys Ala Glu Thr Lys Gln Ile Pro Ile Phe Asn
465                 470                 475                 480

Leu Gln Val Pro Thr Ala Leu Pro Gly Val Asp Pro Met Ile Leu Asp
            485                 490                 495

Pro Arg Asp Thr Tyr Val Asp Pro Leu Gln Trp Glu Ser Lys Ala Lys
        500                 505                 510

Asp Leu Ala Thr Arg Phe Ile Asn Asn Phe Asp Lys Tyr Thr Asp Asn
    515                 520                 525

Ala Glu Gly Lys Ala Leu Val Ala Ala Gly Pro Lys Leu Asp
530                 535                 540

<210> SEQ ID NO 18
<211> LENGTH: 1620
<212> TYPE: DNA
<213> ORGANISM: Selenomonas ruminantium
<220> FEATURE:
<221> NAME/KEY: CDS
<222> LOCATION: (1)..(1620)

<400> SEQUENCE: 18 atg gca aac atc gat ctt agc caa tat ggc atc act ggt act acc gga     48
Met Ala Asn Ile Asp Leu Ser Gln Tyr Gly Ile Thr Gly Thr Thr Gly
1               5                   10                  15 att ctc cac aat ccg tct tac aag acg ctt ttt gaa gaa gag act aaa     96
Ile Leu His Asn Pro Ser Tyr Lys Thr Leu Phe Glu Glu Glu Thr Lys
            20                  25                  30 gaa ggt tta aca ggc tac gaa cag ggt cag gtt tcc gaa ctg ggc gct    144
Glu Gly Leu Thr Gly Tyr Glu Gln Gly Gln Val Ser Glu Leu Gly Ala
        35                  40                  45 gtt aac gta aag act ggt att ttc acc ggc cgt tct cct aaa gat aaa    192
Val Asn Val Lys Thr Gly Ile Phe Thr Gly Arg Ser Pro Lys Asp Lys
    50                  55                  60 ttc atc gtg gat gat gaa act tcc cat gac act gta tgg tgg gat tcc    240
Phe Ile Val Asp Asp Glu Thr Ser His Asp Thr Val Trp Trp Asp Ser
65                  70                  75                  80 gaa gat tat cac aac gat aac cac aga gct acg ccg gaa acc tgg aac    288
Glu Asp Tyr His Asn Asp Asn His Arg Ala Thr Pro Glu Thr Trp Asn
                85                  90                  95 gct ctg aaa gaa atc gct aaa aag gaa ctg tcc aac aag aaa ctc tac    336
Ala Leu Lys Glu Ile Ala Lys Lys Glu Leu Ser Asn Lys Lys Leu Tyr
            100                 105                 110 gtt gta gat gct ttc tgc ggt gcc aac aaa gac acc cgc atg gct gtc    384
Val Val Asp Ala Phe Cys Gly Ala Asn Lys Asp Thr Arg Met Ala Val
        115                 120                 125 cgc ttc atc gta gaa gtt gct tgg cag gca cat ttc gta acg aat atg    432
Arg Phe Ile Val Glu Val Ala Trp Gln Ala His Phe Val Thr Asn Met
    130                 135                 140 ttc atc cag ccg acg gaa gaa gag ctg gct aac ttc aag ccg gac ttc    480
Phe Ile Gln Pro Thr Glu Glu Glu Leu Ala Asn Phe Lys Pro Asp Phe
145                 150                 155                 160 gta gtt tac aac gct tcc aag gct aaa gtt gaa aac tac aag gaa ctt    528
Val Val Tyr Asn Ala Ser Lys Ala Lys Val Glu Asn Tyr Lys Glu Leu
                165                 170                 175 ggt ctc cat tcc gaa acg gca gta gta ttt aac ctc acg agc cgc gaa    576
Gly Leu His Ser Glu Thr Ala Val Val Phe Asn Leu Thr Ser Arg Glu
            180                 185                 190 cag gtt atc atc aac acc tgg tac ggc ggt gaa atg aag aag ggt atg    624
Gln Val Ile Ile Asn Thr Trp Tyr Gly Gly Glu Met Lys Lys Gly Met
        195                 200                 205 ttt tcc atg atg aac tac ttc ctg ccg ctc aag ggg att gct gct atg    672
```

```
        Phe Ser Met Met Asn Tyr Phe Leu Pro Leu Lys Gly Ile Ala Ala Met
            210             215                 220 cat tgc tcc gct aat acg gac aag cag ggc cag aac acg gct atc ttc          720
His Cys Ser Ala Asn Thr Asp Lys Gln Gly Gln Asn Thr Ala Ile Phe
225                 230                 235                 240 ttc ggc ctc tcc ggc acg ggt aaa acc acc ctg tcc acg gac ccg aaa          768
Phe Gly Leu Ser Gly Thr Gly Lys Thr Thr Leu Ser Thr Asp Pro Lys
                245                 250                 255 cgt ctc ctg att ggt gat gat gaa cac ggc tgg gat gat gaa ggc gta          816
Arg Leu Leu Ile Gly Asp Asp Glu His Gly Trp Asp Asp Glu Gly Val
                    260                 265                 270 ttc aac ttc gaa ggc ggc tgc tat gct aag gtt atc aac ctc gac atg          864
Phe Asn Phe Glu Gly Gly Cys Tyr Ala Lys Val Ile Asn Leu Asp Met
                275                 280                 285 gaa tcc gaa ccg gac atc tat ggc gcc atc aaa cgt aac gct ctg ctc          912
Glu Ser Glu Pro Asp Ile Tyr Gly Ala Ile Lys Arg Asn Ala Leu Leu
290                 295                 300 gaa aac gtt acc ctc gac gac aag ggc aac atc gac ttt gcc gat aag          960
Glu Asn Val Thr Leu Asp Asp Lys Gly Asn Ile Asp Phe Ala Asp Lys
305                 310                 315                 320 acc atc acg gaa aac acc cgt gta tcc tat cct atc gac cac atc aaa         1008
Thr Ile Thr Glu Asn Thr Arg Val Ser Tyr Pro Ile Asp His Ile Lys
                325                 330                 335 ggc acc gtt aag ggc ttt gtt aac gac aag agc gca gct ccg gca gct         1056
Gly Thr Val Lys Gly Phe Val Asn Asp Lys Ser Ala Ala Pro Ala Ala
                340                 345                 350 aag agt gtt atc ttc ctg tcc gct gat gct ttc ggc gta ctg ccc ccg         1104
Lys Ser Val Ile Phe Leu Ser Ala Asp Ala Phe Gly Val Leu Pro Pro
                355                 360                 365 gtt tcc atc ctg act ccg gaa cag acg aag tat tac ttc ctc tcc ggc         1152
Val Ser Ile Leu Thr Pro Glu Gln Thr Lys Tyr Tyr Phe Leu Ser Gly
370                 375                 380 ttc acg gct aaa ctg gct ggt acg gaa cgc ggc atc acc gaa ccg aca         1200
Phe Thr Ala Lys Leu Ala Gly Thr Glu Arg Gly Ile Thr Glu Pro Thr
385                 390                 395                 400 ccg acc ttc tcc gct tgc ttc ggt cag gca ttc ctc gaa ctg cat ccg         1248
Pro Thr Phe Ser Ala Cys Phe Gly Gln Ala Phe Leu Glu Leu His Pro
                405                 410                 415 acc aag tac gca gaa gaa ctc gtt aag aag atg gag gct aac ggc acg         1296
Thr Lys Tyr Ala Glu Glu Leu Val Lys Lys Met Glu Ala Asn Gly Thr
                420                 425                 430 aag gca tac ctc gtg aac acg ggc tgg aat ggt tcc ggc aag cgt atc         1344
Lys Ala Tyr Leu Val Asn Thr Gly Trp Asn Gly Ser Gly Lys Arg Ile
                435                 440                 445 tcc atc aaa gat acc cgt ggc atc atc gat gct atc cat agc ggc gct         1392
Ser Ile Lys Asp Thr Arg Gly Ile Ile Asp Ala Ile His Ser Gly Ala
450                 455                 460 atc aaa aaa gct ccg acc aag aag att ccg ttc ttc aac ctc gaa gta         1440
Ile Lys Lys Ala Pro Thr Lys Lys Ile Pro Phe Phe Asn Leu Glu Val
465                 470                 475                 480 ccg acg gaa ctt gag ggc gtt gac acc aac atc ctc gac ccg aag gat         1488
Pro Thr Glu Leu Glu Gly Val Asp Thr Asn Ile Leu Asp Pro Lys Asp
                485                 490                 495 acc tat gct aac ccg gct gat tgg gaa gca aaa gca aaa gac ctc gct         1536
Thr Tyr Ala Asn Pro Ala Asp Trp Glu Ala Lys Ala Lys Asp Leu Ala
                500                 505                 510 cag cgc ttc atc aag aac ttc gac aaa tac acg aag aac aat gaa gct         1584
Gln Arg Phe Ile Lys Asn Phe Asp Lys Tyr Thr Lys Asn Asn Glu Ala
                515                 520                 525 ggt aag gct ctc gtt gcc gct ggt ccg cag ctc taa                         1620
Gly Lys Ala Leu Val Ala Ala Gly Pro Gln Leu
```

```
Gly Lys Ala Leu Val Ala Ala Gly Pro Gln Leu
            530                 535

<210> SEQ ID NO 19
<211> LENGTH: 539
<212> TYPE: PRT
<213> ORGANISM: Selenomonas ruminantium

<400> SEQUENCE: 19

Met Ala Asn Ile Asp Leu Ser Gln Tyr Gly Ile Thr Gly Thr Thr Gly
  1               5                  10                  15

Ile Leu His Asn Pro Ser Tyr Lys Thr Leu Phe Glu Glu Thr Lys
             20                  25                  30

Glu Gly Leu Thr Gly Tyr Glu Gln Gly Gln Val Ser Glu Leu Gly Ala
             35                  40                  45

Val Asn Val Lys Thr Gly Ile Phe Thr Gly Arg Ser Pro Lys Asp Lys
 50                  55                  60

Phe Ile Val Asp Asp Glu Thr Ser His Asp Thr Val Trp Trp Asp Ser
 65                  70                  75                  80

Glu Asp Tyr His Asn Asp Asn His Arg Ala Thr Pro Glu Thr Trp Asn
                 85                  90                  95

Ala Leu Lys Glu Ile Ala Lys Lys Glu Leu Ser Asn Lys Lys Leu Tyr
            100                 105                 110

Val Val Asp Ala Phe Cys Gly Ala Asn Lys Asp Thr Arg Met Ala Val
            115                 120                 125

Arg Phe Ile Val Glu Val Ala Trp Gln Ala His Phe Val Thr Asn Met
        130                 135                 140

Phe Ile Gln Pro Thr Glu Glu Leu Ala Asn Phe Lys Pro Asp Phe
145                 150                 155                 160

Val Val Tyr Asn Ala Ser Lys Ala Lys Val Glu Asn Tyr Lys Glu Leu
                165                 170                 175

Gly Leu His Ser Glu Thr Ala Val Val Phe Asn Leu Thr Ser Arg Glu
            180                 185                 190

Gln Val Ile Ile Asn Thr Trp Tyr Gly Gly Glu Met Lys Lys Gly Met
        195                 200                 205

Phe Ser Met Met Asn Tyr Phe Leu Pro Leu Lys Gly Ile Ala Ala Met
210                 215                 220

His Cys Ser Ala Asn Thr Asp Lys Gln Gly Gln Asn Thr Ala Ile Phe
225                 230                 235                 240

Phe Gly Leu Ser Gly Thr Gly Lys Thr Thr Leu Ser Thr Asp Pro Lys
                245                 250                 255

Arg Leu Leu Ile Gly Asp Asp Glu His Gly Trp Asp Asp Glu Gly Val
            260                 265                 270

Phe Asn Phe Glu Gly Gly Cys Tyr Ala Lys Val Ile Asn Leu Asp Met
        275                 280                 285

Glu Ser Glu Pro Asp Ile Tyr Gly Ala Ile Lys Arg Asn Ala Leu Leu
290                 295                 300

Glu Asn Val Thr Leu Asp Asp Lys Gly Asn Ile Asp Phe Ala Asp Lys
305                 310                 315                 320

Thr Ile Thr Glu Asn Thr Arg Val Ser Tyr Pro Ile Asp His Ile Lys
                325                 330                 335

Gly Thr Val Lys Gly Phe Val Asn Asp Lys Ser Ala Ala Pro Ala Ala
            340                 345                 350

Lys Ser Val Ile Phe Leu Ser Ala Asp Ala Phe Gly Val Leu Pro Pro
        355                 360                 365
```

```
Val Ser Ile Leu Thr Pro Glu Gln Thr Lys Tyr Tyr Phe Leu Ser Gly
        370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Gln Ala Phe Leu Glu Leu His Pro
                405                 410                 415

Thr Lys Tyr Ala Glu Glu Leu Val Lys Lys Met Glu Ala Asn Gly Thr
            420                 425                 430

Lys Ala Tyr Leu Val Asn Thr Gly Trp Asn Gly Ser Gly Lys Arg Ile
        435                 440                 445

Ser Ile Lys Asp Thr Arg Gly Ile Ile Asp Ala Ile His Ser Gly Ala
    450                 455                 460

Ile Lys Lys Ala Pro Thr Lys Lys Ile Pro Phe Phe Asn Leu Glu Val
465                 470                 475                 480

Pro Thr Glu Leu Glu Gly Val Asp Thr Asn Ile Leu Asp Pro Lys Asp
                485                 490                 495

Thr Tyr Ala Asn Pro Ala Asp Trp Glu Ala Lys Ala Lys Asp Leu Ala
            500                 505                 510

Gln Arg Phe Ile Lys Asn Phe Asp Lys Tyr Thr Lys Asn Asn Glu Ala
        515                 520                 525

Gly Lys Ala Leu Val Ala Ala Gly Pro Gln Leu
    530                 535

<210> SEQ ID NO 20
<211> LENGTH: 1674
<212> TYPE: DNA
<213> ORGANISM: Enterobacter aerogenes
<220> FEATURE:
<221> NAME/KEY: CDS
<222> LOCATION: (121)..(1554)

<400> SEQUENCE: 20
tattttactc tgtgtaataa ataaagggcg cttagatgtc ctgtccacgg cacggttctc      60
cccccgggcc aatgcgtgaa agcgtaaaaa agtaccaaat actcaggagc actctcaatt    120 atg ttt aag aat gca ttt gct aac ctg cag aag gtc ggt aaa tcg ctg    168
Met Phe Lys Asn Ala Phe Ala Asn Leu Gln Lys Val Gly Lys Ser Leu
1               5                   10                  15 atg ctg cca gta tcc gta ctg cct att gca ggt atc ctg ctg ggc gtc    216
Met Leu Pro Val Ser Val Leu Pro Ile Ala Gly Ile Leu Leu Gly Val
                20                  25                  30 ggt tct gcc aac ttc agc tgg ctg cca gcc gtg gtc tcc cac gtc atg    264
Gly Ser Ala Asn Phe Ser Trp Leu Pro Ala Val Val Ser His Val Met
            35                  40                  45 gcg gaa gca ggc ggt tca gtt ttc gcc aat atg ccg ctg atc ttc gca    312
Ala Glu Ala Gly Gly Ser Val Phe Ala Asn Met Pro Leu Ile Phe Ala
        50                  55                  60 atc ggt gtt gcg ctt ggc ttc acc aat aac gac ggt gta tcc gca ctg    360
Ile Gly Val Ala Leu Gly Phe Thr Asn Asn Asp Gly Val Ser Ala Leu
65                  70                  75                  80 gct gca gtc gta gct tac ggc atc atg gtg aaa acc atg gcg gta gtc    408
Ala Ala Val Val Ala Tyr Gly Ile Met Val Lys Thr Met Ala Val Val
                85                  90                  95 gcg ccg ctg gtt ctg cat tta cct gct gag gaa atc gca gcc aaa cac    456
Ala Pro Leu Val Leu His Leu Pro Ala Glu Glu Ile Ala Ala Lys His
                100                 105                 110 ctg gct gat acc ggc gtg ctt ggc ggt att atc tcc ggt gcg att gca    504
Leu Ala Asp Thr Gly Val Leu Gly Gly Ile Ile Ser Gly Ala Ile Ala
            115                 120                 125
```

```
gcc tac atg ttc aac cgc ttc tac cgt atc aag ctg cct gaa tat ctg    552
Ala Tyr Met Phe Asn Arg Phe Tyr Arg Ile Lys Leu Pro Glu Tyr Leu
130                 135                 140 ggc ttc ttc gcg ggc aag cgt ttt gtg ccg atc atc tct ggt ctc gcc    600
Gly Phe Phe Ala Gly Lys Arg Phe Val Pro Ile Ile Ser Gly Leu Ala
145                 150                 155                 160 gct atc ttc acc ggc gtg atc ctg tcc ttc atc tgg ccg ccg att ggt    648
Ala Ile Phe Thr Gly Val Ile Leu Ser Phe Ile Trp Pro Pro Ile Gly
                165                 170                 175 tcc gcc atc cag acc ttc tct cag tgg gct gct tac cag aac ccg gtt    696
Ser Ala Ile Gln Thr Phe Ser Gln Trp Ala Ala Tyr Gln Asn Pro Val
            180                 185                 190 gtg gcg ttc ggt atc tac ggt ttc atc gag cgt tgc ctg gta ccg ttt    744
Val Ala Phe Gly Ile Tyr Gly Phe Ile Glu Arg Cys Leu Val Pro Phe
        195                 200                 205 ggt ctg cac cat atc tgg aac gta cct ttc cag atg caa att ggt gaa    792
Gly Leu His His Ile Trp Asn Val Pro Phe Gln Met Gln Ile Gly Glu
    210                 215                 220 tac acc aac gct gca ggt cag gtg ttc cat ggc gac atc cct cgt tac    840
Tyr Thr Asn Ala Ala Gly Gln Val Phe His Gly Asp Ile Pro Arg Tyr
225                 230                 235                 240 atg gca ggc gac ccg act gct ggt aaa ctg tct ggc ggc ttc ctg ttc    888
Met Ala Gly Asp Pro Thr Ala Gly Lys Leu Ser Gly Gly Phe Leu Phe
                245                 250                 255 aaa atg tac ggc ctg ccg gct gca gct atc gcg att tgg cac tct gct    936
Lys Met Tyr Gly Leu Pro Ala Ala Ala Ile Ala Ile Trp His Ser Ala
            260                 265                 270 aaa cca gaa aac cgt gcc aaa gtc ggc ggt att atg atc tcc gcg gcg    984
Lys Pro Glu Asn Arg Ala Lys Val Gly Gly Ile Met Ile Ser Ala Ala
        275                 280                 285 ctg acc tcg ttc ctg acc ggt att acc gag ccg atc gag ttc tcc ttc   1032
Leu Thr Ser Phe Leu Thr Gly Ile Thr Glu Pro Ile Glu Phe Ser Phe
    290                 295                 300 atg ttc gtt gcg ccg atc ctg tat atc atc cac gcg att ctt gca ggc   1080
Met Phe Val Ala Pro Ile Leu Tyr Ile Ile His Ala Ile Leu Ala Gly
305                 310                 315                 320 ctg gca ttc ccg atc tgt atc ctg ttg ggt atg cgt gac ggg acg tcg   1128
Leu Ala Phe Pro Ile Cys Ile Leu Leu Gly Met Arg Asp Gly Thr Ser
                325                 330                 335 ttc tct cac ggt ctg atc gac ttt atc gtt ctt tcc ggc aac agc agc   1176
Phe Ser His Gly Leu Ile Asp Phe Ile Val Leu Ser Gly Asn Ser Ser
            340                 345                 350 aag ctg tgg ctg ttc ccg att gtc ggt att tgc tat gcg atc gtg tac   1224
Lys Leu Trp Leu Phe Pro Ile Val Gly Ile Cys Tyr Ala Ile Val Tyr
        355                 360                 365 tac gtg gtc ttc cgc gtg ctg att aaa gcg ctg aac ctg aaa act cca   1272
Tyr Val Val Phe Arg Val Leu Ile Lys Ala Leu Asn Leu Lys Thr Pro
    370                 375                 380 ggc cgt gaa gat gca act gaa gac agc aaa tcc gct gcg acc agt gaa   1320
Gly Arg Glu Asp Ala Thr Glu Asp Ser Lys Ser Ala Ala Thr Ser Glu
385                 390                 395                 400 atg gcg ccg gcg ctg att gcc gcc ttc ggt ggt aaa gag aac atc aca   1368
Met Ala Pro Ala Leu Ile Ala Ala Phe Gly Gly Lys Glu Asn Ile Thr
                405                 410                 415 aac ctc gac gca tgt att act cgt ctg cgc gta agc gtg gct gac gta   1416
Asn Leu Asp Ala Cys Ile Thr Arg Leu Arg Val Ser Val Ala Asp Val
            420                 425                 430 gcg aaa gtt gat cag gct ggc ctg aaa aaa ctg ggt gct gct ggc gta   1464
Ala Lys Val Asp Gln Ala Gly Leu Lys Lys Leu Gly Ala Ala Gly Val
        435                 440                 445
```

```
gtt gtt gca ggt tcc ggc gtt cag gct att ttc ggc acc aag tcc gat    1512
Val Val Ala Gly Ser Gly Val Gln Ala Ile Phe Gly Thr Lys Ser Asp
    450                 455                 460 aac ctg aaa acc gag atg gat gag tac atc cgc aat agc taa            1554
Asn Leu Lys Thr Glu Met Asp Glu Tyr Ile Arg Asn Ser
465                 470                 475 gacgtagtgt ggggagacta aggcagccaa atggctgcct tttttacgtt ggtattctgg  1614
tcattgtttg gcaatacccg gaaaatgggg gaaatgctta ttccctcagc agctaagtct  1674

<210> SEQ ID NO 21
<211> LENGTH: 477
<212> TYPE: PRT
<213> ORGANISM: Enterobacter aerogenes

<400> SEQUENCE: 21

Met Phe Lys Asn Ala Phe Ala Asn Leu Gln Lys Val Gly Lys Ser Leu
1               5                   10                  15

Met Leu Pro Val Ser Val Leu Pro Ile Ala Gly Ile Leu Leu Gly Val
            20                  25                  30

Gly Ser Ala Asn Phe Ser Trp Leu Pro Ala Val Val Ser His Val Met
        35                  40                  45

Ala Glu Ala Gly Gly Ser Val Phe Ala Asn Met Pro Leu Ile Phe Ala
    50                  55                  60

Ile Gly Val Ala Leu Gly Phe Thr Asn Asn Asp Gly Val Ser Ala Leu
65                  70                  75                  80

Ala Ala Val Val Ala Tyr Gly Ile Met Val Lys Thr Met Ala Val Val
                85                  90                  95

Ala Pro Leu Val Leu His Leu Pro Ala Glu Glu Ile Ala Ala Lys His
            100                 105                 110

Leu Ala Asp Thr Gly Val Leu Gly Gly Ile Ile Ser Gly Ala Ile Ala
        115                 120                 125

Ala Tyr Met Phe Asn Arg Phe Tyr Arg Ile Lys Leu Pro Glu Tyr Leu
    130                 135                 140

Gly Phe Phe Ala Gly Lys Arg Phe Val Pro Ile Ile Ser Gly Leu Ala
145                 150                 155                 160

Ala Ile Phe Thr Gly Val Ile Leu Ser Phe Ile Trp Pro Pro Ile Gly
                165                 170                 175

Ser Ala Ile Gln Thr Phe Ser Gln Trp Ala Ala Tyr Gln Asn Pro Val
            180                 185                 190

Val Ala Phe Gly Ile Tyr Gly Phe Ile Glu Arg Cys Leu Val Pro Phe
        195                 200                 205

Gly Leu His His Ile Trp Asn Val Pro Phe Gln Met Gln Ile Gly Glu
    210                 215                 220

Tyr Thr Asn Ala Ala Gly Gln Val Phe His Gly Asp Ile Pro Arg Tyr
225                 230                 235                 240

Met Ala Gly Asp Pro Thr Ala Gly Lys Leu Ser Gly Gly Phe Leu Phe
                245                 250                 255

Lys Met Tyr Gly Leu Pro Ala Ala Ala Ile Ala Ile Trp His Ser Ala
            260                 265                 270

Lys Pro Glu Asn Arg Ala Lys Val Gly Gly Ile Met Ile Ser Ala Ala
        275                 280                 285

Leu Thr Ser Phe Leu Thr Gly Ile Thr Glu Pro Ile Glu Phe Ser Phe
    290                 295                 300

Met Phe Val Ala Pro Ile Leu Tyr Ile Ile His Ala Ile Leu Ala Gly
305                 310                 315                 320
```

```
Leu Ala Phe Pro Ile Cys Ile Leu Gly Met Arg Asp Gly Thr Ser
            325                 330                 335

Phe Ser His Gly Leu Ile Asp Phe Ile Val Leu Ser Gly Asn Ser Ser
        340                 345                 350

Lys Leu Trp Leu Phe Pro Ile Val Gly Ile Cys Tyr Ala Ile Val Tyr
    355                 360                 365

Tyr Val Val Phe Arg Val Leu Ile Lys Ala Leu Asn Leu Lys Thr Pro
370                 375                 380

Gly Arg Glu Asp Ala Thr Glu Asp Ser Lys Ser Ala Ala Thr Ser Glu
385                 390                 395                 400

Met Ala Pro Ala Leu Ile Ala Ala Phe Gly Gly Lys Glu Asn Ile Thr
                405                 410                 415

Asn Leu Asp Ala Cys Ile Thr Arg Leu Arg Val Ser Val Ala Asp Val
            420                 425                 430

Ala Lys Val Asp Gln Ala Gly Leu Lys Lys Leu Gly Ala Ala Gly Val
        435                 440                 445

Val Val Ala Gly Ser Gly Val Gln Ala Ile Phe Gly Thr Lys Ser Asp
    450                 455                 460

Asn Leu Lys Thr Glu Met Asp Glu Tyr Ile Arg Asn Ser
465                 470                 475

<210> SEQ ID NO 22
<211> LENGTH: 89
<212> TYPE: DNA
<213> ORGANISM: Artificial Sequence
<220> FEATURE:
<223> OTHER INFORMATION: primer

<400> SEQUENCE: 22
tattttactc tgtgtaataa ataaagggcg cttagatgtc ctgtccacgg cacggttctc      60
tgaagcctgc ttttttatac taagttggc                                        89

<210> SEQ ID NO 23
<211> LENGTH: 90
<212> TYPE: DNA
<213> ORGANISM: Artificial Sequence
<220> FEATURE:
<223> OTHER INFORMATION: primer

<400> SEQUENCE: 23
agacttagct gctgagggaa taagcatttc ccccattttc cgggtattgc caaacaatga      60
cgctcaagtt agtataaaaa agctgaacga                                       90

<210> SEQ ID NO 24
<211> LENGTH: 545
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(24)
<223> OTHER INFORMATION: Xaa can be any naturally occurring amino acid
<220> FEATURE:
<221> NAME/KEY: misc_feature
<222> LOCATION: (29)..(30)
```

```
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(45)
<223> OTHER INFORMATION: Xaa can be any naturally occurring amino acid
<220> FEATURE:
<221> NAME/KEY: misc_feature
<222> LOCATION: (47)..(51)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (84)..(90)
<223> OTHER INFORMATION: Xaa can be any naturally occurring amino acid
<220> FEATURE:
<221> NAME/KEY: misc_feature
<222> LOCATION: (94)..(100)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (105)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: misc_feature
<222> LOCATION: (120)..(123)
<223> OTHER INFORMATION: Xaa can be any naturally occurring amino acid
<220> FEATURE:
<221> NAME/KEY: misc_feature
<222> LOCATION: (127)..(130)
<223> OTHER INFORMATION: Xaa can be any naturally occurring amino acid
<220> FEATURE:
<221> NAME/KEY: misc_feature
<222> LOCATION: (132)..(133)
```

```
-continued

<223> OTHER INFORMATION: Xaa can be any naturally occurring amino acid
<220> FEATURE:
<221> NAME/KEY: misc_feature
<222> LOCATION: (136)..(138)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (155)..(158)
<223> OTHER INFORMATION: Xaa can be any naturally occurring amino acid
<220> FEATURE:
<221> NAME/KEY: misc_feature
<222> LOCATION: (160)..(161)
<223> OTHER INFORMATION: Xaa can be any naturally occurring amino acid
<220> FEATURE:
<221> NAME/KEY: misc_feature
<222> LOCATION: (163)..(164)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (171)..(172)
<223> OTHER INFORMATION: Xaa can be any naturally occurring amino acid
<220> FEATURE:
<221> NAME/KEY: misc_feature
<222> LOCATION: (174)..(179)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (188)..(191)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (196)..(198)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (202)..(203)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (225)..(225)
```

-continued

```
<223> OTHER INFORMATION: Xaa can be any naturally occurring amino acid
<220> FEATURE:
<221> NAME/KEY: misc_feature
<222> LOCATION: (227)..(229)
<223> OTHER INFORMATION: Xaa can be any naturally occurring amino acid
<220> FEATURE:
<221> NAME/KEY: misc_feature
<222> LOCATION: (236)..(239)
<223> OTHER INFORMATION: Xaa can be any naturally occurring amino acid
<220> FEATURE:
<221> NAME/KEY: misc_feature
<222> LOCATION: (241)..(243)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (275)..(276)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (293)..(294)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (314)..(318)
<223> OTHER INFORMATION: Xaa can be any naturally occurring amino acid
<220> FEATURE:
<221> NAME/KEY: misc_feature
<222> LOCATION: (320)..(321)
<223> OTHER INFORMATION: Xaa can be any naturally occurring amino acid
<220> FEATURE:
<221> NAME/KEY: misc_feature
<222> LOCATION: (323)..(324)
<223> OTHER INFORMATION: Xaa can be any naturally occurring amino acid
<220> FEATURE:
<221> NAME/KEY: misc_feature
<222> LOCATION: (326)..(328)
<223> OTHER INFORMATION: Xaa can be any naturally occurring amino acid
<220> FEATURE:
<221> NAME/KEY: misc_feature
<222> LOCATION: (339)..(339)
```

-continued

```
<223> OTHER INFORMATION: Xaa can be any naturally occurring amino acid
<220> FEATURE:
<221> NAME/KEY: misc_feature
<222> LOCATION: (342)..(344)
<223> OTHER INFORMATION: Xaa can be any naturally occurring amino acid
<220> FEATURE:
<221> NAME/KEY: misc_feature
<222> LOCATION: (346)..(352)
<223> OTHER INFORMATION: Xaa can be any naturally occurring amino acid
<220> FEATURE:
<221> NAME/KEY: misc_feature
<222> LOCATION: (354)..(357)
<223> OTHER INFORMATION: Xaa can be any naturally occurring amino acid
<220> FEATURE:
<221> NAME/KEY: misc_feature
<222> LOCATION: (359)..(360)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (380)..(381)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (386)..(386)
<223> OTHER INFORMATION: Xaa can be any naturally occurring amino acid
<220> FEATURE:
<221> NAME/KEY: misc_feature
<222> LOCATION: (402)..(402)
<223> OTHER INFORMATION: Xaa can be any naturally occurring amino acid
<220> FEATURE:
<221> NAME/KEY: misc_feature
<222> LOCATION: (415)..(415)
<223> OTHER INFORMATION: Xaa can be any naturally occurring amino acid
<220> FEATURE:
<221> NAME/KEY: misc_feature
<222> LOCATION: (419)..(419)
<223> OTHER INFORMATION: Xaa can be any naturally occurring amino acid
<220> FEATURE:
<221> NAME/KEY: misc_feature
<222> LOCATION: (423)..(424)
<223> OTHER INFORMATION: Xaa can be any naturally occurring amino acid
<220> FEATURE:
<221> NAME/KEY: misc_feature
<222> LOCATION: (427)..(428)
<223> OTHER INFORMATION: Xaa can be any naturally occurring amino acid
<220> FEATURE:
<221> NAME/KEY: misc_feature
<222> LOCATION: (431)..(432)
<223> OTHER INFORMATION: Xaa can be any naturally occurring amino acid
<220> FEATURE:
<221> NAME/KEY: misc_feature
<222> LOCATION: (434)..(436)
<223> OTHER INFORMATION: Xaa can be any naturally occurring amino acid
<220> FEATURE:
<221> NAME/KEY: misc_feature
<222> LOCATION: (438)..(439)
<223> OTHER INFORMATION: Xaa can be any naturally occurring amino acid
<220> FEATURE:
<221> NAME/KEY: misc_feature
<222> LOCATION: (450)..(450)
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (467)..(468)
```

```
<223> OTHER INFORMATION: Xaa can be any naturally occurring amino acid
<220> FEATURE:
<221> NAME/KEY: misc_feature
<222> LOCATION: (470)..(470)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (475)..(479)
<223> OTHER INFORMATION: Xaa can be any naturally occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (483)..(486)
<223> OTHER INFORMATION: Xaa can be any naturally occurring amino acid
<220> FEATURE:
<221> NAME/KEY: misc_feature
<222> LOCATION: (488)..(489)
<223> OTHER INFORMATION: Xaa can be any naturally occurring amino acid
<220> FEATURE:
<221> NAME/KEY: misc_feature
<222> LOCATION: (491)..(491)
<223> OTHER INFORMATION: Xaa can be any naturally occurring amino acid
<220> FEATURE:
<221> NAME/KEY: misc_feature
<222> LOCATION: (494)..(496)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid
<220> FEATURE:
<221> NAME/KEY: misc_feature
<222> LOCATION: (505)..(509)
<223> OTHER INFORMATION: Xaa can be any naturally occurring amino acid
<220> FEATURE:
<221> NAME/KEY: misc_feature
<222> LOCATION: (511)..(512)
<223> OTHER INFORMATION: Xaa can be any naturally occurring amino acid
<220> FEATURE:
<221> NAME/KEY: misc_feature
<222> LOCATION: (515)..(515)
<223> OTHER INFORMATION: Xaa can be any naturally occurring amino acid
<220> FEATURE:
<221> NAME/KEY: misc_feature
<222> LOCATION: (519)..(519)
<223> OTHER INFORMATION: Xaa can be any naturally occurring amino acid
<220> FEATURE:
<221> NAME/KEY: misc_feature
<222> LOCATION: (522)..(523)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid
<220> FEATURE:
<221> NAME/KEY: misc_feature
<222> LOCATION: (529)..(537)
<223> OTHER INFORMATION: Xaa can be any naturally occurring amino acid
<220> FEATURE:
<221> NAME/KEY: misc_feature
<222> LOCATION: (539)..(540)
<223> OTHER INFORMATION: Xaa can be any naturally occurring amino acid
<220> FEATURE:
<221> NAME/KEY: misc_feature
<222> LOCATION: (544)..(545)
<223> OTHER INFORMATION: Xaa can be any naturally occurring amino acid

<400> SEQUENCE: 24

Xaa Xaa Xaa Xaa Xaa Xaa Xaa Xaa Xaa Xaa Leu Xaa Xaa Xaa Gly Xaa
1               5                   10                  15

Xaa Xaa Xaa Xaa Xaa Xaa Xaa Xaa Asn Pro Ser Tyr Xaa Xaa Leu Glu
```

```
                   20                  25                  30
Xaa Glu Glu Thr Xaa Xaa Xaa Leu Xaa Gly Xaa Xaa Gly Xaa Xaa
            35                  40                  45

Xaa Xaa Xaa Gly Ala Xaa Xaa Val Xaa Thr Gly Ile Phe Thr Gly Arg
        50                  55                  60

Ser Pro Lys Asp Lys Xaa Ile Val Xaa Asp Xaa Xaa Xaa Asp Thr
65                  70                  75                  80

Xaa Trp Trp Xaa Xaa Xaa Xaa Xaa Asn Asp Asn Xaa Xaa Xaa
                85                  90                  95

Xaa Xaa Xaa Xaa Trp Xaa Xaa Leu Xaa Xaa Xaa Xaa Xaa Xaa Leu
            100                 105                 110

Ser Xaa Lys Xaa Xaa Xaa Val Xaa Xaa Xaa Xaa Cys Gly Ala Xaa Xaa
        115                 120                 125

Xaa Xaa Arg Xaa Xaa Val Arg Xaa Xaa Xaa Glu Val Ala Trp Gln Ala
        130                 135                 140

His Phe Val Xaa Asn Met Phe Ile Xaa Pro Xaa Xaa Xaa Xaa Leu Xaa
145                 150                 155                 160

Xaa Phe Xaa Xaa Asp Phe Xaa Val Xaa Asn Xaa Xaa Lys Xaa Xaa Xaa
            165                 170                 175

Xaa Xaa Xaa Lys Glu Xaa Gly Leu Xaa Ser Glu Xaa Xaa Xaa Xaa Phe
        180                 185                 190

Asn Xaa Thr Xaa Xaa Xaa Gln Xaa Ile Xaa Xaa Thr Trp Tyr Gly Gly
        195                 200                 205

Glu Met Lys Lys Gly Met Phe Xaa Met Met Asn Tyr Xaa Leu Pro Leu
        210                 215                 220

Xaa Gly Xaa Xaa Xaa Met His Cys Ser Ala Asn Xaa Xaa Xaa Xaa Gly
225                 230                 235                 240

Xaa Xaa Xaa Ala Xaa Phe Phe Gly Leu Ser Gly Thr Gly Lys Thr Thr
            245                 250                 255

Leu Ser Thr Asp Pro Lys Arg Xaa Leu Ile Gly Asp Asp Glu His Gly
        260                 265                 270

Trp Asp Xaa Xaa Gly Xaa Phe Asn Xaa Glu Gly Gly Cys Tyr Ala Lys
        275                 280                 285

Xaa Ile Xaa Leu Xaa Xaa Glu Xaa Glu Pro Asp Ile Tyr Xaa Ala Ile
        290                 295                 300

Xaa Arg Xaa Ala Leu Leu Glu Asn Val Xaa Xaa Xaa Xaa Xaa Gly Xaa
305                 310                 315                 320

Xaa Asp Xaa Xaa Asp Xaa Xaa Xaa Thr Glu Asn Thr Arg Val Ser Tyr
        325                 330                 335

Pro Ile Xaa His Ile Xaa Xaa Val Xaa Xaa Xaa Xaa Xaa Xaa
        340                 345                 350

Ser Xaa Xaa Xaa Xaa Ala Xaa Xaa Val Ile Phe Leu Xaa Ala Asp Ala
        355                 360                 365

Phe Gly Val Leu Pro Pro Val Ser Xaa Leu Thr Xaa Xaa Gln Thr Xaa
        370                 375                 380

Tyr Xaa Phe Leu Ser Gly Phe Thr Ala Lys Leu Ala Gly Thr Glu Arg
385                 390                 395                 400

Gly Xaa Thr Glu Pro Thr Pro Thr Phe Ser Ala Cys Phe Gly Xaa Ala
        405                 410                 415

Phe Leu Xaa Leu His Pro Xaa Xaa Tyr Ala Xaa Xaa Leu Val Xaa Xaa
            420                 425                 430

Met Xaa Xaa Xaa Gly Xaa Xaa Ala Tyr Leu Val Asn Thr Gly Trp Asn
        435                 440                 445
```

```
Gly Xaa Gly Lys Arg Ile Ser Ile Lys Asp Thr Arg Xaa Ile Ile Asp
    450                 455                 460

Ala Ile Xaa Xaa Gly Xaa Ile Xaa Lys Ala Xaa Xaa Xaa Xaa Xaa Pro
465                 470                 475                 480

Xaa Phe Xaa Xaa Xaa Xaa Pro Xaa Xaa Leu Xaa Gly Val Xaa Xaa Xaa
                485                 490                 495

Ile Leu Asp Pro Xaa Asp Thr Tyr Xaa Xaa Xaa Xaa Trp Xaa Xaa
            500                 505                 510

Lys Ala Xaa Asp Leu Ala Xaa Arg Phe Xaa Xaa Asn Phe Xaa Lys Tyr
        515                 520                 525

Xaa Xaa Xaa Xaa Xaa Xaa Xaa Xaa Leu Xaa Xaa Ala Gly Pro Xaa
    530                 535                 540

Xaa
545
```

<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
tagcgagatc tctgatgtcc ggcggtgctt ttg     33

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
aaaaagagct cttacgcccc gccctgccac tc     32

<210> SEQ ID NO 27
<211> LENGTH: 34
<212> TYPE: DNA
<213> ORGANISM: Artificial Sequence
<220> FEATURE:
<223> OTHER INFORMATION: primer

<400> SEQUENCE: 27
caggatctag aaggagacat gaacgatgaa catc     34

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28
gataaggatc cgaaataaaa gaaaatgcca atagga     36

<210> SEQ ID NO 29
<211> LENGTH: 31
<212> TYPE: DNA
<213> ORGANISM: Artificial Sequence
<220> FEATURE:
<223> OTHER INFORMATION: primer

<400> SEQUENCE: 29
cctttgagct cgcgggcagt gagcgcaacg c     31

-continued

<210> SEQ ID NO 30
<211> LENGTH: 48
<212> TYPE: DNA
<213> ORGANISM: Artificial Sequence
<220> FEATURE:
<223> OTHER INFORMATION: primer

<400> SEQUENCE: 30
ctagagcggc cgccgatcgg gatcctcctg tgtgaaattg ttatccgc                48

<210> SEQ ID NO 31
<211> LENGTH: 42
<212> TYPE: DNA
<213> ORGANISM: Artificial Sequence
<220> FEATURE:
<223> OTHER INFORMATION: primer

<400> SEQUENCE: 31
ctctacgatc gaggaggtta taaaaaatgg atattaatac tg                      42

<210> SEQ ID NO 32
<211> LENGTH: 36
<212> TYPE: DNA
<213> ORGANISM: Artificial Sequence
<220> FEATURE:
<223> OTHER INFORMATION: primer

<400> SEQUENCE: 32
tcaaagcggc cgcttcttcg tctgtttcta ctggta                             36

<210> SEQ ID NO 33
<211> LENGTH: 31
<212> TYPE: DNA
<213> ORGANISM: Artificial Sequence
<220> FEATURE:
<223> OTHER INFORMATION: primer

<400> SEQUENCE: 33
cctttggtac cgcgggcagt gagcgcaacg c                                  31

<210> SEQ ID NO 34
<211> LENGTH: 34
<212> TYPE: DNA
<213> ORGANISM: Artificial Sequence
<220> FEATURE:
<223> OTHER INFORMATION: primer

<400> SEQUENCE: 34
aacaggaatt ctttgcctgg cggcagtagc gcgg                               34

<210> SEQ ID NO 35
<211> LENGTH: 40
<212> TYPE: DNA
<213> ORGANISM: Artificial Sequence
<220> FEATURE:
<223> OTHER INFORMATION: primer P1

<400> SEQUENCE: 35
ctagtaagat cttgaagcct gcttttttat actaagttgg                         40

<210> SEQ ID NO 36
<211> LENGTH: 41
<212> TYPE: DNA
<213> ORGANISM: Artificial Sequence
<220> FEATURE:
<223> OTHER INFORMATION: primer P2

```
<400> SEQUENCE: 36
atgatcgaat tcgaaatcaa ataatgattt tattttgact g                              41

<210> SEQ ID NO 37
<211> LENGTH: 120
<212> TYPE: DNA
<213> ORGANISM: Artificial Sequence
<220> FEATURE:
<223> OTHER INFORMATION: DNA fragment containing attL

<400> SEQUENCE: 37
agatcttgaa gcctgctttt ttatactaag ttggcattat aaaaaagcat tgcttatcaa          60
tttgttgcaa cgaacaggtc actatcagtc aaaataaaat cattatttga tttcgaattc         120

<210> SEQ ID NO 38
<211> LENGTH: 41
<212> TYPE: DNA
<213> ORGANISM: Artificial Sequence
<220> FEATURE:
<223> OTHER INFORMATION: primer P3

<400> SEQUENCE: 38
atgccactgc agtctgttac aggtcactaa taccatctaa g                              41

<210> SEQ ID NO 39
<211> LENGTH: 46
<212> TYPE: DNA
<213> ORGANISM: Artificial Sequence
<220> FEATURE:
<223> OTHER INFORMATION: primer P4

<400> SEQUENCE: 39
accgttaagc tttctagacg ctcaagttag tataaaaaag ctgaac                         46

<210> SEQ ID NO 40
<211> LENGTH: 184
<212> TYPE: DNA
<213> ORGANISM: Artificial Sequence
<220> FEATURE:
<223> OTHER INFORMATION: DNA fragment containing attR

<400> SEQUENCE: 40
ctgcagtctg ttacaggtca ctaataccat ctaagtagtt gattcatagt gactgcatat          60
gttgtgtttt acagtattat gtagtctgtt tttatgcaa aatctaattt aatatattga         120
tatttatatc attttacgtt tctcgttcag cttttttata ctaacttgag cgtctagaaa         180
gctt                                                                      184

<210> SEQ ID NO 41
<211> LENGTH: 38
<212> TYPE: DNA
<213> ORGANISM: Artificial Sequence
<220> FEATURE:
<223> OTHER INFORMATION: primer P5

<400> SEQUENCE: 41
ttcttagacg tcaggtggca cttttcgggg aaatgtgc                                  38

<210> SEQ ID NO 42
<211> LENGTH: 37
<212> TYPE: DNA
<213> ORGANISM: Artificial Sequence
<220> FEATURE:
<223> OTHER INFORMATION: primer P6
```

<400> SEQUENCE: 42
taacagagat ctcgcgcaga aaaaaaggat ctcaaga                           37

<210> SEQ ID NO 43
<211> LENGTH: 46
<212> TYPE: DNA
<213> ORGANISM: Artificial Sequence
<220> FEATURE:
<223> OTHER INFORMATION: primer P7

<400> SEQUENCE: 43
aacagagatc taagcttaga tcctttgcct ggcggcagta gcgcgg                 46

<210> SEQ ID NO 44
<211> LENGTH: 35
<212> TYPE: DNA
<213> ORGANISM: Artificial Sequence
<220> FEATURE:
<223> OTHER INFORMATION: primer P8

<400> SEQUENCE: 44
ataaactgca gcaaaaagag tttgtagaaa cgcaa                             35

<210> SEQ ID NO 45
<211> LENGTH: 1388
<212> TYPE: DNA
<213> ORGANISM: Artificial Sequence
<220> FEATURE:
<223> OTHER INFORMATION: DNA fragment containing Tc gene and ter_thrL

<400> SEQUENCE: 45
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120
cggcaccgtc accctggatg ctgtaggcat aggcttggtt atgccggtac tgccgggcct   180
cttgcgggat atcgtccatt ccgacagcat cgccagtcac tatggcgtgc tgctagcgct   240
atatgcgttg atgcaatttc tatgcgcacc cgttctcgga gcactgtccg accgctttgg   300
ccgccgccca gtcctgctcg cttcgctact tggagccact atcgactacg cgatcatggc   360
gaccacaccc gtcctgtgga tcctctacgc cggacgcatc gtggccggca tcaccggcgc   420
cacaggtgcg gttgctggcg cctatatcgc cgacatcacc gatggggaag atcgggctcg   480
ccacttcggg ctcatgagcg cttgtttcgg cgtgggtatg gtggcaggcc ccgtggccgg   540
gggactgttg ggcgccatct ccttgcatgc accattcctt gcggcggcgg tgctcaacgg   600
cctcaaccta ctactgggct gcttcctaat gcaggagtcg cataagggag agcgtcgacc   660
gatgcccttg agagccttca acccagtcag ctccttccgg tgggcgcggg gcatgactat   720
cgtcgccgca cttatgactg tcttctttat catgcaactc gtaggacagg tgccggcagc   780
gctctgggtc attttcggcg aggaccgctt tcgctggagc gcgacgatga tcggcctgtc   840
gcttgcggta ttcggaatct tgcacgccct cgctcaagcc ttcgtcactg gtcccgccac   900
caaacgtttc ggcgagaagc aggccattat cgccggcatg gcggccgacg cgctgggcta   960
cgtcttgctg gcgttcgcga cgcgaggctg atggccttc cccattatga ttcttctcgc  1020
ttccggcggc atcgggatgc ccgcgttgca ggccatgctg tccaggcagg tagatgacga  1080
ccatcaggga cagcttcaag gatcgctcgc ggctcttacc agcctaactt cgatcactgg  1140
accgctgatc gtcacggcga tttatgccgc ctcggcgagc acatggaacg ggttggcatg  1200
gattgtaggc gccgccctat accttgtctg cctccccgcg ttgcgtcgcg gtgcatggag  1260

```
ccgggccacc tcgacctgaa tggaagccgg cggcacctcg ctaacggatt caccactcca    1320
actagaaagc ttaacacaga aaaagcccg cacctgacag tgcgggcttt tttttcgac     1380 cactgcag                                                             1388
```

<210> SEQ ID NO 46
<211> LENGTH: 36
<212> TYPE: DNA
<213> ORGANISM: Artificial Sequence
<220> FEATURE:
<223> OTHER INFORMATION: primer P9

<400> SEQUENCE: 46

```
agtaattcta gaaagcttaa cacagaaaaa agcccg                              36
```

<210> SEQ ID NO 47
<211> LENGTH: 43
<212> TYPE: DNA
<213> ORGANISM: Artificial Sequence
<220> FEATURE:
<223> OTHER INFORMATION: primer P10

<400> SEQUENCE: 47

```
ctagtaggat ccctgcagtg gtcgaaaaaa aaagcccgca ctg                      43
```